(12) United States Patent
Showmaker et al.

(10) Patent No.: US 11,236,316 B2
(45) Date of Patent: *Feb. 1, 2022

(54) PROCESS FOR DEGRADING MANNAN-CONTAINING CELLULOSIC MATERIALS

(71) Applicant: Novozymes A/S, Bagsvaerd (DK)

(72) Inventors: Harry Showmaker, Raleigh, NC (US); Laerke Tvedebrink Haahr, Bagsvaerd (DK); Kristian Bertel Romer M. Krogh, Bagsvaerd (DK); Johan Belfrage, Cupar (GB); Lone Baekgaard, Frederiksberg (DK); Armindo Ribiero Gaspar, Rolesville, NC (US); Claudia Geddes, Raleigh, NC (US)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/368,785

(22) Filed: Mar. 28, 2019

(65) Prior Publication Data

US 2019/0218537 A1  Jul. 18, 2019

Related U.S. Application Data

(62) Division of application No. 15/109,696, filed as application No. PCT/US2015/010423 on Jan. 7, 2015.

(60) Provisional application No. 61/924,491, filed on Jan. 7, 2014.

(51) Int. Cl.
| | |
|---|---|
| *C12P 7/00* | (2006.01) |
| *C12P 19/02* | (2006.01) |
| *C12P 19/14* | (2006.01) |
| *C12N 9/24* | (2006.01) |
| *C12N 9/42* | (2006.01) |

(52) U.S. Cl.
CPC ......... *C12N 9/2488* (2013.01); *C12N 9/2434* (2013.01); *C12N 9/2445* (2013.01); *C12P 7/00* (2013.01); *C12P 19/02* (2013.01); *C12P 19/14* (2013.01); *C12P 2203/00* (2013.01)

(58) Field of Classification Search
None
See application file for complete search history.

(56) References Cited

U.S. PATENT DOCUMENTS

2016/0333333 A1* 11/2016 Showmaker ............ C12P 19/02

FOREIGN PATENT DOCUMENTS

| | | |
|---|---|---|
| CN | 103525792 B | 1/2014 |
| CN | 102978187 B | 9/2014 |
| WO | 2009/074685 A1 | 6/2009 |
| WO | 2013/016115 A1 | 1/2013 |

OTHER PUBLICATIONS

Alsarrani et al., Journal of Taibah University for Sciecne, vol. 5, pp. 1-6 (2011).
Chauhan et al., Appl. Microbiol. Biotechnol., vol. 93, No. 5, pp. 1817-1830 (2012).
Clarke et al., Appl. Microbiol. Biotechnol., vol. 53, pp. 661-667 (2000).
Couturier et al., PLOS ONE, vol. 8, Issue 11, article No. e79800, pp. 1-9 (2013).
Sae-Lee, Walailak J. Sci. & Tech., vol. 4, No. 1, pp. 67-82 (2007).
Varnai et al., Bioresource Technology, vol. 102, pp. 9096-9104 (2011).
Wang et al., Current Biotechnology, vol. 4, No. 5, pp. 340-345 (2014).
Wang et al., Appl. Microbiol. Biotechnol., vol. 99, pp. 1217-1228 (2015).
Nierman et al., UNIPROT Accession No. B8M6W7_TALSN, published Mar. 30, 2009.
Bai et al, GENESEQ Accession No. BBE08613, Published Jun. 5, 2014.
Fedorova et al, GENBANK Accession No. XP_002480621.1 Published Jul. 2, 2009.
Brink et al, 2011, Appl Microbiol Biotechnol, vol. 91, pp. 1477-1492.
Luo et al, 2013, Acta Cryst Section F69, pp. 1100-1102.

* cited by examiner

*Primary Examiner* — Richard C Ekstrom
(74) *Attorney, Agent, or Firm* — David Fazzolare

(57) ABSTRACT

The present invention relates to processes comprising enzymatic degradation of mannan-containing cellulosic materials for producing a hydrolyzate. The invention also relates to processes of producing a fermentation product from mannan-containing cellulosic materials.

12 Claims, No Drawings

Specification includes a Sequence Listing.

SEQUENCE LISTING

<160> NUMBER OF SEQ ID NOS: 35

<210> SEQ ID NO 1
<211> LENGTH: 228
<212> TYPE: PRT
<213> ORGANISM: Thermoascus aurantiacus

<400> SEQUENCE: 1

```
Gly Phe Val Gln Asn Ile Val Ile Asp Gly Lys Lys Tyr Tyr Gly Gly
1               5                   10                  15

Tyr Leu Val Asn Gln Tyr Pro Tyr Met Ser Asn Pro Pro Glu Val Ile
            20                  25                  30

Ala Trp Ser Thr Thr Ala Thr Asp Leu Gly Phe Val Asp Gly Thr Gly
        35                  40                  45

Tyr Gln Thr Pro Asp Ile Ile Cys His Arg Gly Ala Lys Pro Gly Ala
    50                  55                  60

Leu Thr Ala Pro Val Ser Pro Gly Gly Thr Val Glu Leu Gln Trp Thr
65                  70                  75                  80

Pro Trp Pro Asp Ser His His Gly Pro Val Ile Asn Tyr Leu Ala Pro
                85                  90                  95

Cys Asn Gly Asp Cys Ser Thr Val Asp Lys Thr Gln Leu Glu Phe Phe
            100                 105                 110

Lys Ile Ala Glu Ser Gly Leu Ile Asn Asp Asp Asn Pro Pro Gly Ile
        115                 120                 125

Trp Ala Ser Asp Asn Leu Ile Ala Ala Asn Asn Ser Trp Thr Val Thr
    130                 135                 140

Ile Pro Thr Thr Ile Ala Pro Gly Asn Tyr Val Leu Arg His Glu Ile
145                 150                 155                 160

Ile Ala Leu His Ser Ala Gln Asn Gln Asp Gly Ala Gln Asn Tyr Pro
                165                 170                 175

Gln Cys Ile Asn Leu Gln Val Thr Gly Gly Gly Ser Asp Asn Pro Ala
            180                 185                 190

Gly Thr Leu Gly Thr Ala Leu Tyr His Asp Thr Asp Pro Gly Ile Leu
        195                 200                 205

Ile Asn Ile Tyr Gln Lys Leu Ser Ser Tyr Ile Ile Pro Gly Pro Pro
    210                 215                 220

Leu Tyr Thr Gly
225
```

<210> SEQ ID NO 2
<211> LENGTH: 323
<212> TYPE: PRT
<213> ORGANISM: Trichoderma reesei

<400> SEQUENCE: 2

-continued

```
His Gly His Ile Asn Asp Ile Val Ile Asn Gly Val Trp Tyr Gln Ala
1               5                   10                  15

Tyr Asp Pro Thr Thr Phe Pro Tyr Glu Ser Asn Pro Ile Val Val
            20                  25                  30

Gly Trp Thr Ala Ala Asp Leu Asp Asn Gly Phe Val Ser Pro Asp Ala
            35                  40                  45

Tyr Gln Asn Pro Asp Ile Ile Cys His Lys Asn Ala Thr Asn Ala Lys
50                  55                  60

Gly His Ala Ser Val Lys Ala Gly Asp Thr Ile Leu Phe Gln Trp Val
65                  70                  75                  80

Pro Val Pro Trp Pro His Pro Gly Pro Ile Val Asp Tyr Leu Ala Asn
                85                  90                  95

Cys Asn Gly Asp Cys Glu Thr Val Asp Lys Thr Thr Leu Glu Phe Phe
            100                 105                 110

Lys Ile Asp Gly Val Gly Leu Leu Ser Gly Gly Asp Pro Gly Thr Trp
            115                 120                 125

Ala Ser Asp Val Leu Ile Ser Asn Asn Thr Trp Val Val Lys Ile
130                 135                 140

Pro Asp Asn Leu Ala Pro Gly Asn Tyr Val Leu Arg His Glu Ile Ile
145                 150                 155                 160

Ala Leu His Ser Ala Gly Gln Ala Asn Gly Ala Gln Asn Tyr Pro Gln
                165                 170                 175

Cys Phe Asn Ile Ala Val Ser Gly Ser Gly Ser Leu Gln Pro Ser Gly
            180                 185                 190

Val Leu Gly Thr Asp Leu Tyr His Ala Thr Asp Pro Gly Val Leu Ile
            195                 200                 205

Asn Ile Tyr Thr Ser Pro Leu Asn Tyr Ile Ile Pro Gly Pro Thr Val
210                 215                 220

Val Ser Gly Leu Pro Thr Ser Val Ala Gln Gly Ser Ser Ala Ala Thr
225                 230                 235                 240

Ala Thr Ala Ser Ala Thr Val Pro Gly Gly Gly Ser Gly Pro Thr Ser
                245                 250                 255

Arg Thr Thr Thr Thr Ala Arg Thr Thr Gln Ala Ser Ser Arg Pro Ser
            260                 265                 270

Ser Thr Pro Pro Ala Thr Thr Ser Ala Pro Ala Gly Gly Pro Thr Gln
            275                 280                 285

Thr Leu Tyr Gly Gln Cys Gly Gly Ser Gly Tyr Ser Gly Pro Thr Arg
            290                 295                 300

Cys Ala Pro Pro Ala Thr Cys Ser Thr Leu Asn Pro Tyr Tyr Ala Gln
305                 310                 315                 320

Cys Leu Asn
```

<210> SEQ ID NO 3
<211> LENGTH: 323
<212> TYPE: PRT
<213> ORGANISM: Myceliophthora thermophila

<400> SEQUENCE: 3

```
His Gly His Val Ser His Ile Ile Val Asn Gly Val Tyr Tyr Arg Asn
1               5                   10                  15

Tyr Asp Pro Thr Thr Asp Trp Tyr Gln Pro Asn Pro Thr Val Ile
            20                  25                  30

Gly Trp Thr Ala Ala Asp Gln Asp Asn Gly Phe Val Glu Pro Asn Ser
            35                  40                  45
```

```
Phe Gly Thr Pro Asp Ile Ile Cys His Lys Ser Ala Thr Pro Gly Gly
     50                  55                  60

Gly His Ala Thr Val Ala Ala Gly Asp Lys Ile Asn Ile Val Trp Thr
 65                  70                  75                  80

Pro Glu Trp Pro Glu Ser His Ile Gly Pro Val Ile Asp Tyr Leu Ala
                 85                  90                  95

Ala Cys Asn Gly Asp Cys Glu Thr Val Asp Lys Ser Ser Leu Arg Trp
                100                 105                 110

Phe Lys Ile Asp Gly Ala Gly Tyr Asp Lys Ala Ala Gly Arg Trp Ala
            115                 120                 125

Ala Asp Ala Leu Arg Ala Asn Gly Asn Ser Trp Leu Val Gln Ile Pro
130                 135                 140

Ser Asp Leu Lys Ala Gly Asn Tyr Val Leu Arg His Glu Ile Ile Ala
145                 150                 155                 160

Leu His Gly Ala Gln Ser Pro Asn Gly Ala Gln Ala Tyr Pro Gln Cys
                165                 170                 175

Ile Asn Leu Arg Val Thr Gly Gly Gly Ser Asn Leu Pro Ser Gly Val
            180                 185                 190

Ala Gly Thr Ser Leu Tyr Lys Ala Thr Asp Pro Gly Ile Leu Phe Asn
        195                 200                 205

Pro Tyr Val Ser Ser Pro Asp Tyr Thr Val Pro Gly Pro Ala Leu Ile
210                 215                 220

Ala Gly Ala Ala Ser Ser Ile Ala Gln Ser Thr Ser Val Ala Thr Ala
225                 230                 235                 240

Thr Gly Thr Ala Thr Leu Pro Gly Gly Gly Ala Asn Pro Thr Thr Ala
                245                 250                 255

Thr Thr Thr Ala Ala Thr Ser Ala Ala Pro Ser Thr Thr Leu Arg Thr
            260                 265                 270

Thr Thr Thr Ser Ala Ala Gln Thr Thr Ala Pro Pro Ser Gly Asp Val
        275                 280                 285

Gln Thr Lys Tyr Gly Gln Cys Gly Gly Asn Gly Trp Thr Gly Pro Thr
290                 295                 300

Val Cys Ala Pro Gly Ser Ser Cys Ser Val Leu Asn Glu Trp Tyr Ser
305                 310                 315                 320

Gln Cys Leu

<210> SEQ ID NO 4
<211> LENGTH: 229
<212> TYPE: PRT
<213> ORGANISM: Aspergillus fumigatus

<400> SEQUENCE: 4

His Gly Phe Val Ser Gly Ile Val Ala Asp Gly Lys Tyr Tyr Gly Gly
 1               5                  10                  15

Tyr Leu Val Asn Gln Tyr Pro Tyr Met Ser Asn Pro Pro Asp Thr Ile
            20                  25                  30

Ala Trp Ser Thr Thr Ala Thr Asp Leu Gly Phe Val Asp Gly Thr Gly
        35                  40                  45

Tyr Gln Ser Pro Asp Ile Ile Cys His Arg Asp Ala Lys Asn Gly Lys
50                  55                  60

Leu Thr Ala Thr Val Ala Ala Gly Ser Gln Ile Glu Phe Gln Trp Thr
 65                  70                  75                  80

Thr Trp Pro Glu Ser His His Gly Pro Leu Ile Thr Tyr Leu Ala Pro
                85                  90                  95
```

```
Cys Asn Gly Asp Cys Ala Thr Val Asp Lys Thr Leu Lys Phe Val
            100                 105                 110

Lys Ile Ala Ala Gln Gly Leu Ile Asp Gly Ser Asn Pro Pro Gly Val
        115                 120                 125

Trp Ala Asp Asp Glu Met Ile Ala Asn Asn Asn Thr Ala Thr Val Thr
130                 135                 140

Ile Pro Ala Ser Tyr Ala Pro Gly Asn Tyr Val Leu Arg His Glu Ile
145                 150                 155                 160

Ile Ala Leu His Ser Ala Gly Asn Leu Asn Gly Ala Gln Asn Tyr Pro
                165                 170                 175

Gln Cys Phe Asn Ile Gln Ile Thr Gly Gly Gly Ser Ala Gln Gly Ser
            180                 185                 190

Gly Thr Ala Gly Thr Ser Leu Tyr Lys Asn Thr Asp Pro Gly Ile Lys
        195                 200                 205

Phe Asp Ile Tyr Ser Asp Leu Ser Gly Gly Tyr Pro Ile Pro Gly Pro
210                 215                 220

Ala Leu Phe Asn Ala
225

<210> SEQ ID NO 5
<211> LENGTH: 228
<212> TYPE: PRT
<213> ORGANISM: Penicillium emersonii

<400> SEQUENCE: 5

His Gly Phe Val Gln Gly Ile Val Ile Gly Asp Gln Phe Tyr Ser Gly
1               5                   10                  15

Tyr Ile Val Asn Ser Phe Pro Tyr Glu Ser Asn Pro Pro Val Ile
            20                  25                  30

Gly Trp Ala Thr Thr Ala Thr Asp Leu Gly Phe Val Asp Gly Thr Gly
        35                  40                  45

Tyr Gln Gly Pro Asp Ile Ile Cys His Arg Asn Ala Thr Pro Ala Pro
    50                  55                  60

Leu Thr Ala Pro Val Ala Ala Gly Gly Thr Val Glu Leu Gln Trp Thr
65                  70                  75                  80

Pro Trp Pro Asp Ser His His Gly Pro Val Ile Thr Tyr Leu Ala Pro
                85                  90                  95

Cys Asn Gly Asn Cys Ser Thr Val Asp Lys Thr Thr Leu Glu Phe Phe
            100                 105                 110

Lys Ile Asp Gln Gln Gly Leu Ile Asp Asp Thr Ser Pro Pro Gly Thr
        115                 120                 125

Trp Ala Ser Asp Asn Leu Ile Ala Asn Asn Asn Ser Trp Thr Val Thr
130                 135                 140

Ile Pro Asn Ser Val Ala Pro Gly Asn Tyr Val Leu Arg His Glu Ile
145                 150                 155                 160

Ile Ala Leu His Ser Ala Asn Asn Lys Asp Gly Ala Gln Asn Tyr Pro
                165                 170                 175

Gln Cys Ile Asn Ile Glu Val Thr Gly Gly Gly Ser Asp Ala Pro Glu
            180                 185                 190

Gly Thr Leu Gly Glu Asp Leu Tyr His Asp Thr Asp Pro Gly Ile Leu
        195                 200                 205

Val Asp Ile Tyr Glu Pro Ile Ala Thr Tyr Thr Ile Pro Gly Pro Pro
210                 215                 220

Glu Pro Thr Phe
225
```

<210> SEQ ID NO 6
<211> LENGTH: 250
<212> TYPE: PRT
<213> ORGANISM: Thermomyces lanuginosus

<400> SEQUENCE: 6

His Gly Tyr Val Ser Asn Leu Val Ile Asn Gly Val Tyr Tyr Arg Gly
1               5                   10                  15

Trp Leu Pro Gly Glu Asp Pro Tyr Asn Pro Asp Pro Ile Gly Val
            20                  25                  30

Gly Trp Glu Thr Pro Asn Leu Gly Asn Gly Phe Val Thr Pro Ser Glu
        35                  40                  45

Ala Ser Thr Asp Ala Val Ile Cys His Lys Glu Ala Thr Pro Ala Arg
    50                  55                  60

Gly His Val Ser Val Lys Ala Gly Asp Lys Ile Tyr Ile Gln Trp Gln
65                  70                  75                  80

Pro Asn Pro Trp Pro Asp Ser His His Gly Pro Val Leu Asp Tyr Leu
                85                  90                  95

Ala Pro Cys Asn Gly Pro Cys Glu Ser Val Asp Lys Thr Ser Leu Arg
            100                 105                 110

Phe Phe Lys Ile Asp Gly Val Gly Leu Ile Asp Gly Ser Ser Pro Pro
        115                 120                 125

Gly Tyr Trp Ala Asp Asp Glu Leu Ile Ala Asn Gly Asn Gly Trp Leu
    130                 135                 140

Val Gln Ile Pro Glu Asp Ile Lys Pro Gly Asn Tyr Val Leu Arg His
145                 150                 155                 160

Glu Ile Ile Ala Leu His Ser Ala Gly Asn Pro Asp Gly Ala Gln Leu
                165                 170                 175

Tyr Pro Gln Cys Phe Asn Leu Glu Ile Thr Gly Ser Gly Thr Val Glu
            180                 185                 190

Pro Glu Gly Val Pro Ala Thr Glu Phe Tyr Ser Pro Asp Asp Pro Gly
        195                 200                 205

Ile Leu Val Asn Ile Tyr Glu Pro Leu Ser Thr Tyr Glu Val Pro Gly
    210                 215                 220

Pro Ser Leu Ile Pro Gln Ala Val Gln Ile Glu Gln Ser Ser Ser Ala
225                 230                 235                 240

Ile Thr Ala Thr Gly Thr Pro Thr Pro Ala
                245                 250

<210> SEQ ID NO 7
<211> LENGTH: 343
<212> TYPE: PRT
<213> ORGANISM: Talaromyces leycettanus

<400> SEQUENCE: 7

His Gly His Val Ser Asn Ile Val Ile Asn Gly Val Pro Tyr Gln Gly
1               5                   10                  15

Trp Asp Ile Asp Ser Met Pro Tyr Glu Ser Asp Pro Val Val Val
            20                  25                  30

Ala Trp Glu Thr Pro Asn Thr Ser Asn Gly Phe Ile Thr Pro Asp Gln
        35                  40                  45

Tyr Gly Thr Ser Asp Ile Ile Cys His Leu Asn Ala Thr Asn Ala Lys
    50                  55                  60

Gly His Ala Val Val Ala Ala Gly Asp Lys Ile Ser Ile Gln Trp Thr
65                  70                  75                  80

```
Ala Trp Pro Ser Ser His His Gly Pro Val Ile Ser Tyr Leu Ala Asn
                85                  90                  95

Cys Gly Ala Ser Cys Glu Thr Val Asp Lys Thr Thr Leu Gln Phe Phe
            100                 105                 110

Lys Ile Asp Asn Ile Gly Phe Ile Asp Asp Ser Ser Pro Pro Gly Ile
        115                 120                 125

Trp Ala Ala Asp Gln Leu Glu Ala Asn Asn Asn Thr Trp Leu Val Glu
    130                 135                 140

Ile Pro Pro Thr Ile Ala Pro Gly Tyr Tyr Val Leu Arg Asn Glu Ile
145                 150                 155                 160

Ile Ala Leu His Gly Ala Glu Asn Gln Asp Gly Ala Gln Asn Tyr Pro
                165                 170                 175

Gln Cys Phe Asn Leu Gln Val Thr Gly Ser Gly Thr Asp Lys Pro Ala
            180                 185                 190

Gly Val Leu Gly Thr Gln Leu Tyr Ser Pro Thr Asp Pro Gly Ile Leu
        195                 200                 205

Val Asn Ile Tyr Thr Ser Leu Ser Thr Tyr Ile Val Pro Gly Pro Thr
    210                 215                 220

Pro Tyr Ser Gly Trp Val Ser Val Gln Ser Ser Ala Ile Thr
225                 230                 235                 240

Ala Ser Gly Thr Pro Val Thr Gly Thr Gly Val Ser Pro Thr Thr
                245                 250                 255

Ala Ala Thr Thr Thr Ser Ser His Ser Thr Thr Ser Thr Thr Thr
                260                 265                 270

Gly Pro Thr Val Thr Ser Thr Ser His Thr Thr Thr Thr Thr Pro
                275                 280                 285

Thr Thr Leu Arg Thr Thr Thr Thr Ala Ala Gly Gly Ala Thr
    290                 295                 300

Gln Thr Val Tyr Gly Gln Cys Gly Gly Ser Gly Trp Thr Gly Ala Thr
305                 310                 315                 320

Ala Cys Ala Ala Gly Ala Thr Cys Ser Thr Leu Asn Pro Tyr Tyr Ala
                325                 330                 335

Gln Cys Leu Pro Thr Gly Ala
            340

<210> SEQ ID NO 8
<211> LENGTH: 228
<212> TYPE: PRT
<213> ORGANISM: Talaromyces emersonii

<400> SEQUENCE: 8

His Gly Phe Val Gln Gly Ile Val Ile Gly Asp Gln Phe Tyr Ser Gly
1               5                   10                  15

Tyr Ile Val Asn Glu Phe Pro Tyr Glu Ser Asn Pro Pro Val Ile
                20                  25                  30

Gly Trp Ala Thr Thr Ala Thr Asp Leu Gly Phe Val Asp Gly Thr Glu
            35                  40                  45

Tyr Gln Gly Pro Asp Ile Ile Cys His Arg Asn Ala Thr Pro Ala Leu
        50                  55                  60

Leu Thr Ala Pro Val Ala Gly Gly Thr Val Glu Leu Gln Trp Thr
65                  70                  75                  80

Pro Trp Pro Ser Ser His His Gly Pro Val Ile Thr Tyr Leu Ala Asn
                85                  90                  95

Cys Asn Gly Asn Cys Ser Thr Val Asp Lys Thr Gln Leu Glu Phe Phe
```

```
            100             105             110
Lys Ile Asp Gln Ser Gly Leu Ile Asn Asp Thr Asp Pro Pro Gly Thr
        115                 120                 125

Trp Ala Ser Asp Asn Leu Ile Ala Asn Asn Ser Trp Thr Val Thr
130                 135                 140

Ile Pro Ser Thr Leu Glu Pro Gly Asn Tyr Val Leu Arg His Glu Ile
145                 150                 155                 160

Ile Ala Leu His Ser Ala Gly Asn Lys Asp Gly Ala Gln Asn Tyr Pro
                165                 170                 175

Gln Cys Ile Asn Ile Glu Val Thr Gly Gly Ser Val Glu Pro Thr
            180                 185                 190

Gly Thr Leu Gly Glu Asp Leu Tyr His Asp Thr Asp Pro Gly Ile Leu
        195                 200                 205

Ile Asp Ile Tyr Glu Pro Ile Ala Thr Tyr Thr Ile Pro Gly Pro Pro
210                 215                 220

Glu Pro Thr Phe
225

<210> SEQ ID NO 9
<211> LENGTH: 656
<212> TYPE: PRT
<213> ORGANISM: Aspergillus niger

<400> SEQUENCE: 9

Ala Pro Ala Thr Gly Ala Ser Asn Ser Gln Thr Ile Val Thr Asn Gly
1               5                   10                  15

Thr Ser Phe Ala Leu Asn Gly Asp Asn Val Ser Tyr Arg Phe His Val
            20                  25                  30

Asn Ser Thr Thr Gly Asp Leu Ile Ser Asp His Phe Gly Gly Val Val
        35                  40                  45

Ser Gly Thr Ile Pro Ser Pro Val Glu Pro Ala Val Asn Gly Trp Val
    50                  55                  60

Gly Met Pro Gly Arg Ile Arg Arg Glu Phe Pro Asp Gln Gly Arg Gly
65                  70                  75                  80

Asp Phe Arg Ile Pro Ala Val Arg Ile Arg Glu Ser Ala Gly Tyr Thr
                85                  90                  95

Ala Val Thr Thr Leu Val Val His Leu Tyr Asp Asn Tyr Ser Ser Val
            100                 105                 110

Ala Ala Asp Leu Ser Tyr Ser Ile Phe Pro Lys Tyr Asp Ala Ile Val
        115                 120                 125

Arg Ser Val Asn Val Ile Asn Gln Gly Pro Gly Asn Ile Thr Ile Glu
    130                 135                 140

Ala Leu Ala Ser Ile Ser Ile Asp Phe Pro Tyr Glu Asp Leu Asp Met
145                 150                 155                 160

Val Ser Leu Arg Gly Asp Trp Ala Arg Glu Ala Asn Val Gln Arg Ser
                165                 170                 175

Lys Val Gln Tyr Gly Val Gln Phe Gly Ser Ser Thr Gly Tyr Ser
            180                 185                 190

Ser His Leu His Asn Pro Phe Leu Ala Ile Val Asp Pro Ala Thr Thr
        195                 200                 205

Glu Ser Gln Gly Glu Ala Trp Gly Phe Asn Leu Val Tyr Thr Gly Ser
    210                 215                 220

Phe Ser Ala Gln Val Glu Lys Gly Ser Gln Gly Phe Thr Arg Ala Leu
225                 230                 235                 240
```

```
Leu Gly Phe Asn Pro Asp Gln Leu Ser Trp Asn Leu Gly Pro Gly Glu
                245                 250                 255

Thr Leu Thr Ser Pro Glu Cys Val Ala Val Tyr Ser Asp Lys Gly Leu
            260                 265                 270

Gly Ser Val Ser Arg Lys Phe His Arg Leu Tyr Arg Asn His Leu Met
        275                 280                 285

Lys Ser Lys Phe Ala Thr Ser Asp Arg Pro Val Leu Leu Asn Ser Trp
290                 295                 300

Glu Gly Val Tyr Phe Asp Tyr Asn Gln Ser Ile Glu Thr Leu Ala
305                 310                 315                 320

Glu Glu Ser Ala Ala Leu Gly Val His Leu Phe Val Met Asp Asp Gly
                325                 330                 335

Trp Phe Gly Asp Lys Tyr Pro Arg Val Ser Asp Asn Ala Gly Leu Gly
            340                 345                 350

Asp Trp Met Pro Asn Pro Ala Arg Phe Pro Asp Gly Leu Thr Pro Val
        355                 360                 365

Val Gln Asp Ile Thr Asn Leu Thr Val Asn Gly Thr Glu Ser Thr Lys
    370                 375                 380

Leu Arg Phe Gly Ile Trp Val Glu Pro Glu Met Val Asn Pro Asn Ser
385                 390                 395                 400

Thr Leu Tyr His Glu His Pro Glu Trp Ala Leu His Ala Gly Pro Tyr
                405                 410                 415

Pro Arg Thr Glu Arg Arg Asn Gln Leu Val Leu Asn Leu Ala Leu Pro
            420                 425                 430

Ala Val Gln Asp Phe Ile Ile Asp Phe Met Thr Asn Leu Leu Gln Asp
        435                 440                 445

Thr Gly Ile Ser Tyr Val Lys Trp Asp Asn Asn Arg Gly Ile His Glu
    450                 455                 460

Thr Pro Ser Pro Ser Thr Asp His Gln Tyr Met Leu Gly Leu Tyr Arg
465                 470                 475                 480

Val Phe Asp Thr Leu Thr Thr Arg Phe Pro Asp Val Leu Trp Glu Gly
                485                 490                 495

Cys Ala Ser Gly Gly Gly Arg Phe Asp Ala Gly Met Leu Gln Tyr Val
            500                 505                 510

Pro Gln Ile Trp Thr Ser Asp Asn Thr Asp Ala Ile Asp Arg Ile Thr
        515                 520                 525

Ile Gln Phe Gly Thr Ser Leu Ala Tyr Pro Pro Ser Ala Met Gly Ala
    530                 535                 540

His Leu Ser Ala Val Pro Asn Ala Gln Thr Gly Arg Thr Val Pro Ile
545                 550                 555                 560

Thr Phe Arg Ala His Val Ala Met Met Gly Gly Ser Phe Gly Leu Glu
                565                 570                 575

Leu Asp Pro Ala Thr Val Glu Gly Asp Glu Ile Val Pro Glu Leu Leu
            580                 585                 590

Ala Leu Ala Glu Lys Val Asn Pro Ile Ile Leu Asn Gly Asp Leu Tyr
        595                 600                 605

Arg Leu Arg Leu Pro Gln Asp Ser Gln Trp Pro Ala Ala Leu Phe Val
    610                 615                 620

Thr Gln Asp Gly Ala Gln Ala Val Leu Phe Tyr Phe Gln Val Pro Ala
625                 630                 635                 640

Glu Cys Gln Pro Cys Arg Ala Val Gly Gln Ala Ala Gly Val Gly Pro
                645                 650                 655
```

<210> SEQ ID NO 10
<211> LENGTH: 844
<212> TYPE: PRT
<213> ORGANISM: Aspergillus fumigatus

<400> SEQUENCE: 10

Gln Glu Leu Ala Phe Ser Pro Pro Phe Tyr Pro Ser Pro Trp Ala Asp
1               5                   10                  15

Gly Gln Gly Glu Trp Ala Asp Ala His Arg Arg Ala Val Glu Ile Val
                20                  25                  30

Ser Gln Met Thr Leu Ala Glu Lys Val Asn Leu Thr Thr Gly Thr Gly
            35                  40                  45

Trp Glu Met Asp Arg Cys Val Gly Gln Thr Gly Ser Val Pro Arg Leu
50                  55                  60

Gly Ile Asn Trp Gly Leu Cys Gly Gln Asp Ser Pro Leu Gly Ile Arg
65                  70                  75                  80

Phe Ser Asp Leu Asn Ser Ala Phe Pro Ala Gly Thr Asn Val Ala Ala
                85                  90                  95

Thr Trp Asp Lys Thr Leu Ala Tyr Leu Arg Gly Lys Ala Met Gly Glu
            100                 105                 110

Glu Phe Asn Asp Lys Gly Val Asp Ile Leu Leu Gly Pro Ala Ala Gly
        115                 120                 125

Pro Leu Gly Lys Tyr Pro Asp Gly Gly Arg Ile Trp Glu Gly Phe Ser
130                 135                 140

Pro Asp Pro Val Leu Thr Gly Val Leu Phe Ala Glu Thr Ile Lys Gly
145                 150                 155                 160

Ile Gln Asp Ala Gly Val Ile Ala Thr Ala Lys His Tyr Ile Leu Asn
                165                 170                 175

Glu Gln Glu His Phe Arg Gln Val Gly Glu Ala Gln Gly Tyr Gly Tyr
            180                 185                 190

Asn Ile Thr Glu Thr Ile Ser Ser Asn Val Asp Asp Lys Thr Met His
        195                 200                 205

Glu Leu Tyr Leu Trp Pro Phe Ala Asp Ala Val Arg Ala Gly Val Gly
210                 215                 220

Ala Val Met Cys Ser Tyr Asn Gln Ile Asn Asn Ser Tyr Gly Cys Gln
225                 230                 235                 240

Asn Ser Gln Thr Leu Asn Lys Leu Leu Lys Ala Glu Leu Gly Phe Gln
                245                 250                 255

Gly Phe Val Met Ser Asp Trp Ser Ala His His Ser Gly Val Gly Ala
            260                 265                 270

Ala Leu Ala Gly Leu Asp Met Ser Met Pro Gly Asp Ile Ser Phe Asp
        275                 280                 285

Asp Gly Leu Ser Phe Trp Gly Thr Asn Leu Thr Val Ser Val Leu Asn
290                 295                 300

Gly Thr Val Pro Ala Trp Arg Val Asp Asp Met Ala Val Arg Ile Met
305                 310                 315                 320

Thr Ala Tyr Tyr Lys Val Gly Arg Asp Arg Leu Arg Ile Pro Pro Asn
                325                 330                 335

Phe Ser Ser Trp Thr Arg Asp Glu Tyr Gly Trp Glu His Ser Ala Val
            340                 345                 350

Ser Glu Gly Ala Trp Thr Lys Val Asn Asp Phe Val Asn Val Gln Arg
        355                 360                 365

Ser His Ser Gln Ile Ile Arg Glu Ile Gly Ala Ala Ser Thr Val Leu
370                 375                 380

```
Leu Lys Asn Thr Gly Ala Leu Pro Leu Thr Gly Lys Glu Val Lys Val
385                 390                 395                 400

Gly Val Leu Gly Glu Asp Ala Gly Ser Asn Pro Trp Gly Ala Asn Gly
                405                 410                 415

Cys Pro Asp Arg Gly Cys Asp Asn Gly Thr Leu Ala Met Ala Trp Gly
                420                 425                 430

Ser Gly Thr Ala Asn Phe Pro Tyr Leu Val Thr Pro Glu Gln Ala Ile
            435                 440                 445

Gln Arg Glu Val Ile Ser Asn Gly Gly Asn Val Phe Ala Val Thr Asp
        450                 455                 460

Asn Gly Ala Leu Ser Gln Met Ala Asp Val Ala Ser Gln Ser Ser Val
465                 470                 475                 480

Ser Leu Val Phe Val Asn Ala Asp Ser Gly Glu Gly Phe Ile Ser Val
                485                 490                 495

Asp Gly Asn Glu Gly Asp Arg Lys Asn Leu Thr Leu Trp Lys Asn Gly
                500                 505                 510

Glu Ala Val Ile Asp Thr Val Val Ser His Cys Asn Asn Thr Ile Val
            515                 520                 525

Val Ile His Ser Val Gly Pro Val Leu Ile Asp Arg Trp Tyr Asp Asn
        530                 535                 540

Pro Asn Val Thr Ala Ile Ile Trp Ala Gly Leu Pro Gly Gln Glu Ser
545                 550                 555                 560

Gly Asn Ser Leu Val Asp Val Leu Tyr Gly Arg Val Asn Pro Ser Ala
                565                 570                 575

Lys Thr Pro Phe Thr Trp Gly Lys Thr Arg Glu Ser Tyr Gly Ala Pro
            580                 585                 590

Leu Leu Thr Glu Pro Asn Asn Gly Asn Gly Ala Pro Gln Asp Asp Phe
        595                 600                 605

Asn Glu Gly Val Phe Ile Asp Tyr Arg His Phe Asp Lys Arg Asn Glu
            610                 615                 620

Thr Pro Ile Tyr Glu Phe Gly His Gly Leu Ser Tyr Thr Thr Phe Gly
625                 630                 635                 640

Tyr Ser His Leu Arg Val Gln Ala Leu Asn Ser Ser Ser Ser Ala Tyr
                645                 650                 655

Val Pro Thr Ser Gly Glu Thr Lys Pro Ala Pro Thr Tyr Gly Glu Ile
            660                 665                 670

Gly Ser Ala Ala Asp Tyr Leu Tyr Pro Glu Gly Leu Lys Arg Ile Thr
        675                 680                 685

Lys Phe Ile Tyr Pro Trp Leu Asn Ser Thr Asp Leu Glu Asp Ser Ser
690                 695                 700

Asp Asp Pro Asn Tyr Gly Trp Glu Asp Ser Glu Tyr Ile Pro Glu Gly
                705                 710                 715                 720

Ala Arg Asp Gly Ser Pro Gln Pro Leu Leu Lys Ala Gly Gly Ala Pro
            725                 730                 735

Gly Gly Asn Pro Thr Leu Tyr Gln Asp Leu Val Arg Val Ser Ala Thr
        740                 745                 750

Ile Thr Asn Thr Gly Asn Val Ala Gly Tyr Glu Val Pro Gln Leu Tyr
        755                 760                 765

Val Ser Leu Gly Gly Pro Asn Glu Pro Arg Val Val Leu Arg Lys Phe
        770                 775                 780

Asp Arg Ile Phe Leu Ala Pro Gly Glu Gln Lys Val Trp Thr Thr Thr
785                 790                 795                 800

Leu Asn Arg Arg Asp Leu Ala Asn Trp Asp Val Glu Ala Gln Asp Trp
```

```
                    805                 810                 815
Val Ile Thr Lys Tyr Pro Lys Val His Val Gly Ser Ser Ser Arg
                820                 825                 830

Lys Leu Pro Leu Arg Ala Pro Leu Pro Arg Val Tyr
            835                 840

<210> SEQ ID NO 11
<211> LENGTH: 842
<212> TYPE: PRT
<213> ORGANISM: Penicillium brasilianum

<400> SEQUENCE: 11

Ala Ile Glu Ser Phe Ser Glu Pro Phe Tyr Pro Ser Pro Trp Met Asn
1               5                   10                  15

Pro His Ala Glu Gly Trp Glu Ala Ala Tyr Gln Lys Ala Gln Asp Phe
            20                  25                  30

Val Ser Gln Leu Thr Ile Leu Glu Lys Ile Asn Leu Thr Thr Gly Val
        35                  40                  45

Gly Trp Glu Asn Gly Pro Cys Val Gly Asn Thr Gly Ser Ile Pro Arg
    50                  55                  60

Leu Gly Phe Lys Gly Phe Cys Thr Gln Asp Ser Pro Gln Gly Val Arg
65                  70                  75                  80

Phe Ala Asp Tyr Ser Ser Ala Phe Thr Ser Gln Met Ala Ala Ala
                85                  90                  95

Thr Phe Asp Arg Ser Ile Leu Tyr Gln Arg Gly Gln Ala Met Ala Gln
            100                 105                 110

Glu His Lys Ala Lys Gly Ile Thr Ile Gln Leu Gly Pro Val Ala Gly
        115                 120                 125

Pro Leu Gly Arg Ile Pro Glu Gly Gly Arg Asn Trp Glu Gly Phe Ser
    130                 135                 140

Pro Asp Pro Val Leu Thr Gly Ile Ala Met Ala Glu Thr Ile Lys Gly
145                 150                 155                 160

Met Gln Asp Thr Gly Val Ile Ala Cys Ala Lys His Tyr Ile Gly Asn
                165                 170                 175

Glu Gln Glu His Phe Arg Gln Val Gly Glu Ala Ala Gly His Gly Tyr
            180                 185                 190

Thr Ile Ser Asp Thr Ile Ser Ser Asn Ile Asp Asp Arg Ala Met His
        195                 200                 205

Glu Leu Tyr Leu Trp Pro Phe Ala Asp Ala Val Arg Ala Gly Val Gly
    210                 215                 220

Ser Phe Met Cys Ser Tyr Ser Gln Ile Asn Asn Ser Tyr Gly Cys Gln
225                 230                 235                 240

Asn Ser Gln Thr Leu Asn Lys Leu Leu Lys Ser Glu Leu Gly Phe Gln
                245                 250                 255

Gly Phe Val Met Ser Asp Trp Gly Ala His His Ser Gly Val Ser Ser
            260                 265                 270

Ala Leu Ala Gly Leu Asp Met Ser Met Pro Gly Asp Thr Glu Phe Asp
        275                 280                 285

Ser Gly Leu Ser Phe Trp Gly Ser Asn Leu Thr Ile Ala Ile Leu Asn
    290                 295                 300

Gly Thr Val Pro Glu Trp Arg Leu Asp Asp Met Ala Met Arg Ile Met
305                 310                 315                 320

Ala Ala Tyr Phe Lys Val Gly Leu Thr Ile Glu Asp Gln Pro Asp Val
                325                 330                 335
```

-continued

```
Asn Phe Asn Ala Trp Thr His Asp Thr Tyr Gly Tyr Lys Tyr Ala Tyr
                340                 345                 350

Ser Lys Glu Asp Tyr Glu Gln Val Asn Trp His Val Asp Val Arg Ser
        355                 360                 365

Asp His Asn Lys Leu Ile Arg Glu Thr Ala Ala Lys Gly Thr Val Leu
    370                 375                 380

Leu Lys Asn Asn Phe His Ala Leu Pro Leu Lys Gln Pro Arg Phe Val
385                 390                 395                 400

Ala Val Val Gly Gln Asp Ala Gly Pro Asn Pro Lys Gly Pro Asn Gly
                405                 410                 415

Cys Ala Asp Arg Gly Cys Asp Gln Gly Thr Leu Ala Met Gly Trp Gly
                420                 425                 430

Ser Gly Ser Thr Glu Phe Pro Tyr Leu Val Thr Pro Asp Thr Ala Ile
        435                 440                 445

Gln Ser Lys Val Leu Glu Tyr Gly Gly Arg Tyr Glu Ser Ile Phe Asp
    450                 455                 460

Asn Tyr Asp Asp Asn Ala Ile Leu Ser Leu Val Ser Gln Pro Asp Ala
465                 470                 475                 480

Thr Cys Ile Val Phe Ala Asn Ala Asp Ser Gly Glu Gly Tyr Ile Thr
                485                 490                 495

Val Asp Asn Asn Trp Gly Asp Arg Asn Asn Leu Thr Leu Trp Gln Asn
            500                 505                 510

Ala Asp Gln Val Ile Ser Thr Val Ser Ser Arg Cys Asn Asn Thr Ile
        515                 520                 525

Val Val Leu His Ser Val Gly Pro Val Leu Leu Asn Gly Ile Tyr Glu
    530                 535                 540

His Pro Asn Ile Thr Ala Ile Val Trp Ala Gly Met Pro Gly Glu Glu
545                 550                 555                 560

Ser Gly Asn Ala Leu Val Asp Ile Leu Trp Gly Asn Val Asn Pro Ala
                565                 570                 575

Gly Arg Thr Pro Phe Thr Trp Ala Lys Ser Arg Glu Asp Tyr Gly Thr
            580                 585                 590

Asp Ile Met Tyr Glu Pro Asn Asn Gly Gln Arg Ala Pro Gln Gln Asp
        595                 600                 605

Phe Thr Glu Ser Ile Tyr Leu Asp Tyr Arg His Phe Asp Lys Ala Gly
    610                 615                 620

Ile Glu Pro Ile Tyr Glu Phe Gly Phe Gly Leu Ser Tyr Thr Thr Phe
625                 630                 635                 640

Glu Tyr Ser Asp Leu Arg Val Val Lys Lys Tyr Val Gln Pro Tyr Ser
                645                 650                 655

Pro Thr Thr Gly Thr Gly Ala Gln Ala Pro Ser Ile Gly Gln Pro Pro
            660                 665                 670

Ser Gln Asn Leu Asp Thr Tyr Lys Phe Pro Ala Thr Tyr Lys Tyr Ile
        675                 680                 685

Lys Thr Phe Ile Tyr Pro Tyr Leu Asn Ser Thr Val Ser Leu Arg Ala
    690                 695                 700

Ala Ser Lys Asp Pro Glu Tyr Gly Arg Thr Asp Phe Ile Pro His Ala
705                 710                 715                 720

Ala Arg Asp Gly Ser Pro Gln Pro Leu Asn Pro Ala Gly Asp Pro Val
                725                 730                 735

Ala Ser Gly Gly Asn Asn Met Leu Tyr Asp Glu Leu Tyr Glu Val Thr
            740                 745                 750

Ala Gln Ile Lys Asn Thr Gly Asp Val Ala Gly Asp Glu Val Val Gln
```

-continued

```
                755                 760                 765
Leu Tyr Val Asp Leu Gly Gly Asp Asn Pro Pro Arg Gln Leu Arg Asn
770                 775                 780

Phe Asp Arg Phe Tyr Leu Leu Pro Gly Gln Ser Ser Thr Phe Arg Ala
785                 790                 795                 800

Thr Leu Thr Arg Arg Asp Leu Ser Asn Trp Asp Ile Glu Ala Gln Asn
                805                 810                 815

Trp Arg Val Thr Glu Ser Pro Lys Arg Val Tyr Val Gly Arg Ser Ser
                820                 825                 830

Arg Asp Leu Pro Leu Ser Ser Gln Leu Glu
                835                 840

<210> SEQ ID NO 12
<211> LENGTH: 910
<212> TYPE: PRT
<213> ORGANISM: Aspergillus niger

<400> SEQUENCE: 12

Gln Tyr Ile Arg Asp Leu Ser Thr Glu Lys Trp Thr Leu Ser Ser Arg
1               5                   10                  15

Ala Leu Asn Arg Thr Val Pro Ala Gln Phe Pro Ser Gln Val His Leu
                20                  25                  30

Asp Leu Leu Arg Ala Gly Val Ile Gly Glu Tyr His Gly Leu Asn Asp
            35                  40                  45

Phe Asn Leu Arg Trp Ile Ala Ala Asn Trp Thr Tyr Thr Ser Gln
        50                  55                  60

Pro Ile Lys Gly Leu Leu Asp Asn Tyr Asp Ser Thr Trp Leu Val Phe
65                  70                  75                  80

Asp Gly Leu Asp Thr Phe Ala Thr Ile Ser Phe Cys Gly Gln Gln Ile
                85                  90                  95

Ala Ser Thr Asp Asn Gln Phe Arg Gln Tyr Ala Phe Asp Val Ser Thr
                100                 105                 110

Ala Leu Gly Ser Cys Lys Gly Asp Pro Val Leu Ser Ile Asn Phe Gly
            115                 120                 125

Ser Ala Pro Asn Ile Val Asp Ala Ile Ala Gln Asp Ser Asn Ser Gln
        130                 135                 140

Lys Trp Pro Asp Val Gln Leu Thr Tyr Glu Tyr Pro Asn Arg Trp
145                 150                 155                 160

Phe Met Arg Lys Glu Gln Ser Asp Phe Gly Trp Asp Trp Gly Pro Ala
                165                 170                 175

Phe Ala Pro Ala Gly Pro Trp Lys Pro Ala Tyr Ile Val Gln Leu Asp
                180                 185                 190

Lys Lys Glu Ser Val Tyr Val Leu Asn Thr Asp Leu Asp Ile Tyr Arg
            195                 200                 205

Lys Gly Gln Ile Asn Tyr Leu Pro Pro Asp Gln Ser Gln Pro Trp Val
        210                 215                 220

Val Asn Ala Ser Ile Asp Ile Leu Gly Pro Leu Pro Thr Lys Pro Thr
225                 230                 235                 240

Met Ser Ile Glu Val Arg Asp Thr His Ser Gly Thr Ile Leu Thr Ser
                245                 250                 255

Arg Thr Leu Asn Asn Val Ser Val Ala Gly Asn Ala Ile Thr Gly Val
                260                 265                 270

Thr Val Leu Asp Gly Leu Thr Pro Lys Leu Trp Pro Gln Gly Leu
            275                 280                 285
```

```
Gly Asp Gln Asn Leu Tyr Asn Val Ser Ile Thr Val Gln Ser Arg Gly
    290                 295                 300

Asn Gln Thr Val Ala Ser Val Asn Lys Arg Thr Gly Phe Arg Thr Ile
305                 310                 315                 320

Phe Leu Asn Gln Arg Asn Ile Thr Glu Ala Gln Arg Ala Gln Gly Ile
                325                 330                 335

Ala Pro Gly Ala Asn Trp His Phe Glu Val Asn Gly His Glu Phe Tyr
            340                 345                 350

Ala Lys Gly Ser Asn Leu Ile Pro Pro Asp Ser Phe Trp Thr Arg Val
        355                 360                 365

Thr Glu Glu Lys Met Ser Arg Leu Phe Asp Ala Val Val Gly Asn
370                 375                 380

Gln Asn Met Leu Arg Val Trp Ser Ser Gly Ala Tyr Leu His Asp Tyr
385                 390                 395                 400

Ile Tyr Asp Leu Ala Asp Glu Lys Gly Ile Leu Leu Trp Ser Glu Phe
                405                 410                 415

Glu Phe Ser Asp Ala Leu Tyr Pro Ser Asp Ala Phe Leu Glu Asn
            420                 425                 430

Val Ala Ala Glu Ile Val Tyr Asn Val Arg Arg Val Asn His His Pro
        435                 440                 445

Ser Leu Ala Leu Trp Ala Gly Gly Asn Glu Ile Glu Ser Leu Met Leu
450                 455                 460

Pro Arg Val Lys Asp Ala Ala Pro Ser Ser Tyr Ser Tyr Tyr Val Gly
465                 470                 475                 480

Glu Tyr Glu Lys Met Tyr Ile Ser Leu Phe Leu Pro Leu Val Tyr Glu
                485                 490                 495

Asn Thr Arg Ser Ile Ser Tyr Ser Pro Ser Ser Thr Thr Glu Gly Tyr
            500                 505                 510

Leu Tyr Ile Asp Leu Ser Ala Pro Val Pro Met Ala Glu Arg Tyr Asp
        515                 520                 525

Asn Thr Thr Ser Gly Ser Tyr Tyr Gly Asp Thr Asp His Tyr Asp Tyr
    530                 535                 540

Asp Thr Ser Val Ala Phe Asp Tyr Gly Ser Tyr Pro Val Gly Arg Phe
545                 550                 555                 560

Ala Asn Glu Phe Gly Phe His Ser Met Pro Ser Leu Gln Thr Trp Gln
                565                 570                 575

Gln Ala Val Asp Thr Glu Asp Leu Tyr Phe Asn Ser Ser Val Val Met
            580                 585                 590

Leu Arg Asn His His Asp Pro Ala Gly Gly Leu Met Thr Asp Asn Tyr
        595                 600                 605

Ala Asn Ser Ala Thr Gly Met Gly Glu Met Thr Met Gly Val Val Ser
610                 615                 620

Tyr Tyr Pro Ile Pro Ser Lys Ser Asp His Ile Ser Asn Phe Ser Ala
625                 630                 635                 640

Trp Cys His Ala Thr Gln Leu Phe Gln Ala Asp Met Tyr Lys Ser Gln
                645                 650                 655

Ile Gln Phe Tyr Arg Arg Gly Ser Gly Met Pro Glu Arg Gln Leu Gly
            660                 665                 670

Ser Leu Tyr Trp Gln Leu Glu Asp Ile Trp Gln Ala Pro Ser Trp Ala
        675                 680                 685

Gly Ile Glu Tyr Gly Gly Arg Trp Lys Val Leu His His Val Met Arg
    690                 695                 700

Asp Ile Tyr Gln Pro Val Ile Val Ser Pro Phe Trp Asn Tyr Thr Thr
```

```
                705                 710                 715                 720
Gly Ser Leu Asp Val Tyr Val Thr Ser Asp Leu Trp Ser Pro Ala Ala
                    725                 730                 735
Gly Thr Val Asp Leu Thr Trp Leu Asp Leu Ser Gly Arg Pro Ile Ala
                    740                 745                 750
Gly Asn Ala Gly Thr Pro Lys Ser Val Pro Phe Thr Val Gly Gly Leu
                    755                 760                 765
Asn Ser Thr Arg Ile Tyr Gly Thr Asn Val Ser Ser Leu Gly Leu Pro
                    770                 775                 780
Asp Thr Lys Asp Ala Val Leu Ile Leu Ser Leu Ser Ala His Gly Arg
785                 790                 795                 800
Leu Pro Asn Ser Asp Arg Thr Thr Asn Leu Thr His Glu Asn Tyr Ala
                    805                 810                 815
Thr Leu Ser Trp Pro Lys Asp Leu Lys Ile Val Asp Pro Gly Leu Lys
                    820                 825                 830
Ile Gly His Ser Ser Lys Lys Thr Thr Val Thr Val Glu Ala Thr Ser
                    835                 840                 845
Gly Val Ser Leu Tyr Thr Trp Leu Asp Tyr Pro Glu Gly Val Val Gly
                    850                 855                 860
Tyr Phe Glu Glu Asn Ala Phe Val Leu Ala Pro Gly Glu Lys Lys Glu
865                 870                 875                 880
Ile Ser Phe Thr Val Leu Glu Asp Thr Thr Asp Gly Ala Trp Val Arg
                    885                 890                 895
Asn Ile Thr Val Gln Ser Leu Trp Asp Gln Lys Val Arg Gly
                    900                 905                 910

<210> SEQ ID NO 13
<211> LENGTH: 772
<212> TYPE: PRT
<213> ORGANISM: Aspergillus fumigatus

<400> SEQUENCE: 13

Gln Ala Asn Thr Ser Tyr Val Asp Tyr Asn Val Glu Ala Asn Pro Asp
1                   5                   10                  15
Leu Thr Pro Gln Ser Val Ala Thr Ile Asp Leu Ser Phe Pro Asp Cys
                    20                  25                  30
Glu Asn Gly Pro Leu Ser Lys Thr Leu Val Cys Asp Thr Ser Ala Arg
                    35                  40                  45
Pro His Asp Arg Ala Ala Ala Leu Val Ser Met Phe Thr Phe Glu Glu
                    50                  55                  60
Leu Val Asn Asn Thr Gly Asn Thr Ser Pro Gly Val Pro Arg Leu Gly
65                  70                  75                  80
Leu Pro Pro Tyr Gln Val Trp Ser Glu Ala Leu His Gly Leu Asp Arg
                    85                  90                  95
Ala Asn Phe Thr Asn Glu Gly Glu Tyr Ser Trp Ala Thr Ser Phe Pro
                    100                 105                 110
Met Pro Ile Leu Thr Met Ser Ala Leu Asn Arg Thr Leu Ile Asn Gln
                    115                 120                 125
Ile Ala Thr Ile Ile Ala Thr Gln Gly Arg Ala Phe Asn Asn Val Gly
                    130                 135                 140
Arg Tyr Gly Leu Asp Val Tyr Ala Pro Asn Ile Asn Ala Phe Arg Ser
145                 150                 155                 160
Ala Met Trp Gly Arg Gly Gln Glu Thr Pro Gly Glu Asp Ala Tyr Cys
                    165                 170                 175
```

```
Leu Ala Ser Ala Tyr Ala Tyr Glu Tyr Ile Thr Gly Ile Gln Gly Gly
                180                 185                 190

Val Asp Pro Glu His Leu Lys Leu Val Ala Thr Ala Lys His Tyr Ala
            195                 200                 205

Gly Tyr Asp Leu Glu Asn Trp Asp Gly His Ser Arg Leu Gly Asn Asp
        210                 215                 220

Met Asn Ile Thr Gln Gln Glu Leu Ser Glu Tyr Tyr Thr Pro Gln Phe
225                 230                 235                 240

Leu Val Ala Ala Arg Asp Ala Lys Val His Ser Val Met Cys Ser Tyr
                245                 250                 255

Asn Ala Val Asn Gly Val Pro Ser Cys Ala Asn Ser Phe Phe Leu Gln
            260                 265                 270

Thr Leu Leu Arg Asp Thr Phe Gly Phe Val Glu Asp Gly Tyr Val Ser
        275                 280                 285

Ser Asp Cys Asp Ser Ala Tyr Asn Val Trp Asn Pro His Glu Phe Ala
290                 295                 300

Ala Asn Ile Thr Gly Ala Ala Asp Ser Ile Arg Ala Gly Thr Asp
305                 310                 315                 320

Ile Asp Cys Gly Thr Thr Tyr Gln Tyr Tyr Phe Gly Glu Ala Phe Asp
            325                 330                 335

Glu Gln Glu Val Thr Arg Ala Glu Ile Glu Arg Gly Val Ile Arg Leu
        340                 345                 350

Tyr Ser Asn Leu Val Arg Leu Gly Tyr Phe Asp Gly Asn Gly Ser Val
        355                 360                 365

Tyr Arg Asp Leu Thr Trp Asn Asp Val Val Thr Thr Asp Ala Trp Asn
370                 375                 380

Ile Ser Tyr Glu Ala Ala Val Glu Gly Ile Val Leu Leu Lys Asn Asp
385                 390                 395                 400

Gly Thr Leu Pro Leu Ala Lys Ser Val Arg Ser Val Ala Leu Ile Gly
            405                 410                 415

Pro Trp Met Asn Val Thr Thr Gln Leu Gln Gly Asn Tyr Phe Gly Pro
        420                 425                 430

Ala Pro Tyr Leu Ile Ser Pro Leu Asn Ala Phe Gln Asn Ser Asp Phe
        435                 440                 445

Asp Val Asn Tyr Ala Phe Gly Thr Asn Ile Ser Ser His Ser Thr Asp
450                 455                 460

Gly Phe Ser Glu Ala Leu Ser Ala Ala Lys Lys Ser Asp Val Ile Ile
465                 470                 475                 480

Phe Ala Gly Gly Ile Asp Asn Thr Leu Glu Ala Glu Ala Met Asp Arg
            485                 490                 495

Met Asn Ile Thr Trp Pro Gly Asn Gln Leu Gln Leu Ile Asp Gln Leu
        500                 505                 510

Ser Gln Leu Gly Lys Pro Leu Ile Val Leu Gln Met Gly Gly Gly Gln
        515                 520                 525

Val Asp Ser Ser Ser Leu Lys Ser Asn Lys Asn Val Asn Ser Leu Ile
        530                 535                 540

Trp Gly Gly Tyr Pro Gly Gln Ser Gly Gly Gln Ala Leu Leu Asp Ile
545                 550                 555                 560

Ile Thr Gly Lys Arg Ala Pro Ala Gly Arg Leu Val Val Thr Gln Tyr
            565                 570                 575

Pro Ala Glu Tyr Ala Thr Gln Phe Pro Ala Thr Asp Met Ser Leu Arg
        580                 585                 590

Pro His Gly Asn Asn Pro Gly Gln Thr Tyr Met Trp Tyr Thr Gly Thr
```

```
                    595                 600                 605
Pro Val Tyr Glu Phe Gly His Gly Leu Phe Tyr Thr Thr Phe His Ala
    610                 615                 620

Ser Leu Pro Gly Thr Gly Lys Asp Lys Thr Ser Phe Asn Ile Gln Asp
625                 630                 635                 640

Leu Leu Thr Gln Pro His Pro Gly Phe Ala Asn Val Glu Gln Met Pro
                645                 650                 655

Leu Leu Asn Phe Thr Val Thr Ile Thr Asn Thr Gly Lys Val Ala Ser
                660                 665                 670

Asp Tyr Thr Ala Met Leu Phe Ala Asn Thr Thr Ala Gly Pro Ala Pro
                675                 680                 685

Tyr Pro Asn Lys Trp Leu Val Gly Phe Asp Arg Leu Ala Ser Leu Glu
            690                 695                 700

Pro His Arg Ser Gln Thr Met Thr Ile Pro Val Thr Ile Asp Ser Val
705                 710                 715                 720

Ala Arg Thr Asp Glu Ala Gly Asn Arg Val Leu Tyr Pro Gly Lys Tyr
                725                 730                 735

Glu Leu Ala Leu Asn Asn Glu Arg Ser Val Val Leu Gln Phe Val Leu
                740                 745                 750

Thr Gly Arg Glu Ala Val Ile Phe Lys Trp Pro Val Glu Gln Gln Gln
            755                 760                 765

Ile Ser Ser Ala
        770

<210> SEQ ID NO 14
<211> LENGTH: 775
<212> TYPE: PRT
<213> ORGANISM: Talaromyces emersonii

<400> SEQUENCE: 14

Gln Asp Asn Gln Thr Tyr Ala Asn Tyr Ser Ser Gln Ser Gln Pro Asp
1               5                   10                  15

Leu Phe Pro Arg Thr Val Ala Thr Ile Asp Leu Ser Phe Pro Asp Cys
                20                  25                  30

Glu Asn Gly Pro Leu Ser Thr Asn Leu Val Cys Asn Thr Ser Ala Asp
            35                  40                  45

Pro Trp Ala Arg Ala Glu Ala Leu Val Ser Leu Phe Thr Leu Glu Glu
    50                  55                  60

Leu Ile Asn Asn Thr Gln Asn Thr Ala Pro Gly Val Pro Arg Leu Gly
65                  70                  75                  80

Leu Pro Gln Tyr Gln Val Trp Asn Glu Ala Leu His Gly Leu Asp Arg
                85                  90                  95

Ala Asn Phe Ser Asp Ser Gly Glu Tyr Ser Trp Ala Thr Ser Phe Pro
            100                 105                 110

Met Pro Ile Leu Ser Met Ala Ser Phe Asn Arg Thr Leu Ile Asn Gln
    115                 120                 125

Ile Ala Ser Ile Ile Ala Thr Gln Ala Arg Ala Phe Asn Asn Ala Gly
130                 135                 140

Arg Tyr Gly Leu Asp Ser Tyr Ala Pro Asn Ile Asn Gly Phe Arg Ser
145                 150                 155                 160

Pro Leu Trp Gly Arg Gly Gln Glu Thr Pro Gly Glu Asp Ala Phe Phe
                165                 170                 175

Leu Ser Ser Ala Tyr Ala Tyr Glu Tyr Ile Thr Gly Leu Gln Gly Gly
            180                 185                 190
```

-continued

```
Val Asp Pro Glu His Val Lys Ile Val Ala Thr Ala Lys His Phe Ala
            195                 200                 205
Gly Tyr Asp Leu Glu Asn Trp Gly Asn Val Ser Arg Leu Gly Ser Asn
            210                 215                 220
Ala Ile Ile Thr Gln Gln Asp Leu Ser Glu Tyr Tyr Thr Pro Gln Phe
225                 230                 235                 240
Leu Ala Ser Ala Arg Tyr Ala Lys Thr Arg Ser Leu Met Cys Ser Tyr
                245                 250                 255
Asn Ala Val Asn Gly Val Pro Ser Cys Ser Asn Ser Phe Phe Leu Gln
            260                 265                 270
Thr Leu Leu Arg Glu Ser Phe Asn Phe Val Asp Asp Gly Tyr Val Ser
            275                 280                 285
Ser Asp Cys Asp Ala Val Tyr Asn Val Phe Asn Pro His Gly Tyr Ala
290                 295                 300
Leu Asn Gln Ser Gly Ala Ala Asp Ser Leu Leu Ala Gly Thr Asp
305                 310                 315                 320
Ile Asp Cys Gly Gln Thr Met Pro Trp His Leu Asn Glu Ser Phe Tyr
                325                 330                 335
Glu Arg Tyr Val Ser Arg Gly Asp Ile Glu Lys Ser Leu Thr Arg Leu
            340                 345                 350
Tyr Ala Asn Leu Val Arg Leu Gly Tyr Phe Asp Gly Asn Asn Ser Val
            355                 360                 365
Tyr Arg Asn Leu Asn Trp Asn Asp Val Val Thr Thr Asp Ala Trp Asn
            370                 375                 380
Ile Ser Tyr Glu Ala Ala Val Glu Gly Ile Thr Leu Leu Lys Asn Asp
385                 390                 395                 400
Gly Thr Leu Pro Leu Ser Lys Lys Val Arg Ser Ile Ala Leu Ile Gly
                405                 410                 415
Pro Trp Ala Asn Ala Thr Val Gln Met Gln Gly Asn Tyr Tyr Gly Thr
            420                 425                 430
Pro Pro Tyr Leu Ile Ser Pro Leu Glu Ala Ala Lys Ala Ser Gly Phe
            435                 440                 445
Thr Val Asn Tyr Ala Phe Gly Thr Asn Ile Ser Thr Asp Ser Thr Gln
            450                 455                 460
Trp Phe Ala Glu Ala Ile Ser Ala Ala Lys Lys Ser Asp Val Ile Ile
465                 470                 475                 480
Tyr Ala Gly Gly Ile Asp Asn Thr Ile Glu Ala Gly Gln Asp Arg
                485                 490                 495
Thr Asp Leu Lys Trp Pro Gly Asn Gln Leu Asp Leu Ile Glu Gln Leu
            500                 505                 510
Ser Lys Val Gly Lys Pro Leu Val Val Leu Gln Met Gly Gly Gln
            515                 520                 525
Val Asp Ser Ser Ser Leu Lys Ala Asn Lys Asn Val Asn Ala Leu Val
530                 535                 540
Trp Gly Gly Tyr Pro Gly Gln Ser Gly Gly Ala Ala Leu Phe Asp Ile
545                 550                 555                 560
Leu Thr Gly Lys Arg Ala Pro Ala Gly Arg Leu Val Ser Thr Gln Tyr
                565                 570                 575
Pro Ala Glu Tyr Ala Thr Gln Phe Pro Ala Asn Asp Met Asn Leu Arg
            580                 585                 590
Pro Asn Gly Ser Asn Pro Gly Gln Thr Tyr Ile Trp Tyr Thr Gly Thr
            595                 600                 605
Pro Val Tyr Glu Phe Gly His Gly Leu Phe Tyr Thr Glu Phe Gln Glu
```

Ser Ala Ala Gly Thr Asn Lys Thr Ser Thr Leu Asp Ile Leu Asp
625                 630                 635                 640

Leu Val Pro Thr Pro His Pro Gly Tyr Glu Tyr Ile Glu Leu Val Pro
            645                 650                 655

Phe Leu Asn Val Thr Val Asp Val Lys Asn Val Gly His Thr Pro Ser
                660                 665                 670

Pro Tyr Thr Gly Leu Leu Phe Ala Asn Thr Thr Ala Gly Pro Lys Pro
            675                 680                 685

Tyr Pro Asn Lys Trp Leu Val Gly Phe Asp Arg Leu Ala Thr Ile His
        690                 695                 700

Pro Ala Lys Thr Ala Gln Val Thr Phe Pro Val Pro Leu Gly Ala Ile
705                 710                 715                 720

Ala Arg Ala Asp Glu Asn Gly Asn Lys Val Ile Phe Pro Gly Glu Tyr
                725                 730                 735

Glu Leu Ala Leu Asn Asn Glu Arg Ser Val Val Val Ser Phe Ser Leu
            740                 745                 750

Thr Gly Asn Ala Ala Thr Leu Glu Asn Trp Pro Val Trp Glu Gln Ala
        755                 760                 765

Val Pro Gly Val Leu Gln Gln
770                 775

<210> SEQ ID NO 15
<211> LENGTH: 465
<212> TYPE: PRT
<213> ORGANISM: Mycelophthora thermophila

<400> SEQUENCE: 15

Ala Pro Val Ile Glu Glu Arg Gln Asn Cys Gly Ala Val Trp Thr Gln
1               5                   10                  15

Cys Gly Gly Asn Gly Trp Gln Gly Pro Thr Cys Cys Ala Ser Gly Ser
            20                  25                  30

Thr Cys Val Ala Gln Asn Glu Trp Tyr Ser Gln Cys Leu Pro Asn Asn
        35                  40                  45

Gln Val Thr Ser Ser Asn Thr Pro Ser Ser Thr Ser Gln Arg
    50                  55                  60

Ser Ser Ser Thr Ser Ser Ser Ser Thr Arg Ser Gly Ser Ser Ser Ser
65                  70                  75                  80

Ser Thr Thr Thr Pro Pro Val Ser Ser Pro Val Thr Ser Ile Pro
            85                  90                  95

Gly Gly Ala Thr Thr Ala Ser Tyr Ser Gly Asn Pro Phe Ser Gly
            100                 105                 110

Val Arg Leu Phe Ala Asn Asp Tyr Tyr Arg Ser Glu Val His Asn Leu
        115                 120                 125

Ala Ile Pro Ser Met Thr Gly Thr Leu Ala Ala Lys Ala Ser Ala Val
130                 135                 140

Ala Glu Val Pro Ser Phe Gln Trp Leu Asp Arg Asn Val Thr Ile Asp
145                 150                 155                 160

Thr Leu Met Val Gln Thr Leu Ser Gln Ile Arg Ala Ala Asn Asn Ala
                165                 170                 175

Gly Ala Asn Pro Pro Tyr Ala Ala Gln Leu Val Val Tyr Asp Leu Pro
            180                 185                 190

Asp Arg Asp Cys Ala Ala Ala Ser Asn Gly Glu Phe Ser Ile Ala
        195                 200                 205

```
Asn Gly Gly Ala Ala Asn Tyr Arg Ser Tyr Ile Asp Ala Ile Arg Lys
    210                 215                 220

His Ile Ile Glu Tyr Ser Asp Ile Arg Ile Ile Leu Val Ile Glu Pro
225                 230                 235                 240

Asp Ser Met Ala Asn Met Val Thr Asn Met Asn Val Ala Lys Cys Ser
                245                 250                 255

Asn Ala Ala Ser Thr Tyr His Glu Leu Thr Val Tyr Ala Leu Lys Gln
            260                 265                 270

Leu Asn Leu Pro Asn Val Ala Met Tyr Leu Asp Ala Gly His Ala Gly
        275                 280                 285

Trp Leu Gly Trp Pro Ala Asn Ile Gln Pro Ala Ala Asp Leu Phe Ala
    290                 295                 300

Gly Ile Tyr Asn Asp Ala Gly Lys Pro Ala Ala Val Arg Gly Leu Ala
305                 310                 315                 320

Thr Asn Val Ala Asn Tyr Asn Ala Trp Ser Ile Ala Ser Ala Pro Ser
                325                 330                 335

Tyr Thr Ser Pro Asn Pro Asn Tyr Asp Glu Lys His Tyr Ile Glu Ala
            340                 345                 350

Phe Ser Pro Leu Leu Asn Ala Ala Gly Phe Pro Ala Arg Phe Ile Val
        355                 360                 365

Asp Thr Gly Arg Asn Gly Lys Gln Pro Thr Gly Gln Gln Gln Trp Gly
    370                 375                 380

Asp Trp Cys Asn Val Lys Gly Thr Gly Phe Gly Val Arg Pro Thr Ala
385                 390                 395                 400

Asn Thr Gly His Asp Leu Val Asp Ala Phe Val Trp Val Lys Pro Gly
                405                 410                 415

Gly Glu Ser Asp Gly Thr Ser Asp Thr Ser Ala Ala Arg Tyr Asp Tyr
            420                 425                 430

His Cys Gly Leu Ser Asp Ala Leu Gln Pro Ala Pro Glu Ala Gly Gln
        435                 440                 445

Trp Phe Gln Ala Tyr Phe Glu Gln Leu Leu Thr Asn Ala Asn Pro Pro
    450                 455                 460

Phe
465

<210> SEQ ID NO 16
<211> LENGTH: 497
<212> TYPE: PRT
<213> ORGANISM: Trichoderma reesei

<400> SEQUENCE: 16

Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Thr Gly Ser Val
                20                  25                  30

Val Ile Asp Ala Asn Trp Arg Trp Thr His Ala Thr Asn Ser Ser Thr
            35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
            100                 105                 110
```

```
Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
            165                 170                 175

Pro Arg Asp Leu Lys Phe Ile Asn Gly Gln Ala Asn Val Glu Gly Trp
        180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
            245                 250                 255

Asp Pro Asp Gly Cys Asp Trp Asn Pro Tyr Arg Leu Gly Asn Thr Ser
        260                 265                 270

Phe Tyr Gly Pro Gly Ser Ser Phe Thr Leu Asp Thr Thr Lys Lys Leu
        275                 280                 285

Thr Val Val Thr Gln Phe Glu Thr Ser Gly Ala Ile Asn Arg Tyr Tyr
        290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
            325                 330                 335

Glu Phe Gly Gly Ser Ser Phe Ser Asp Lys Gly Gly Leu Thr Gln Phe
        340                 345                 350

Lys Lys Ala Thr Ser Gly Gly Met Val Leu Val Met Ser Leu Trp Asp
        355                 360                 365

Asp Tyr Tyr Ala Asn Met Leu Trp Leu Asp Ser Thr Tyr Pro Thr Asn
        370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
            405                 410                 415

Thr Phe Ser Asn Ile Lys Phe Gly Pro Ile Gly Ser Thr Gly Asn Pro
        420                 425                 430

Ser Gly Gly Asn Pro Pro Gly Gly Asn Pro Pro Gly Thr Thr Thr Thr
        435                 440                 445

Arg Arg Pro Ala Thr Thr Thr Gly Ser Ser Pro Gly Pro Thr Gln Ser
450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
            485                 490                 495

Leu

<210> SEQ ID NO 17
<211> LENGTH: 453
<212> TYPE: PRT
```

<213> ORGANISM: Trichoderma reesei

<400> SEQUENCE: 17

Val Pro Leu Glu Glu Arg Gln Ala Cys Ser Ser Val Trp Gly Gln Cys
1               5                   10                  15

Gly Gly Gln Asn Trp Ser Gly Pro Thr Cys Cys Ala Ser Gly Ser Thr
            20                  25                  30

Cys Val Tyr Ser Asn Asp Tyr Tyr Ser Gln Cys Leu Pro Gly Ala Ala
        35                  40                  45

Ser Ser Ser Ser Ser Thr Arg Ala Ala Ser Thr Thr Ser Arg Val Ser
    50                  55                  60

Pro Thr Thr Ser Arg Ser Ser Ala Thr Pro Pro Gly Ser Thr
65                  70                  75                  80

Thr Thr Arg Val Pro Pro Val Gly Ser Gly Thr Ala Thr Tyr Ser Gly
                85                  90                  95

Asn Pro Phe Val Gly Val Thr Pro Trp Ala Asn Ala Tyr Tyr Ala Ser
            100                 105                 110

Glu Val Ser Ser Leu Ala Ile Pro Ser Leu Thr Gly Ala Met Ala Thr
        115                 120                 125

Ala Ala Ala Ala Val Ala Lys Val Pro Ser Phe Met Trp Leu Asp Thr
    130                 135                 140

Leu Asp Lys Thr Pro Leu Met Glu Gln Thr Leu Ala Asp Ile Arg Thr
145                 150                 155                 160

Ala Asn Lys Asn Gly Gly Asn Tyr Ala Gly Gln Phe Val Val Tyr Asp
                165                 170                 175

Leu Pro Asp Arg Asp Cys Ala Ala Leu Ala Ser Asn Gly Glu Tyr Ser
            180                 185                 190

Ile Ala Asp Gly Gly Val Ala Lys Tyr Lys Asn Tyr Ile Asp Thr Ile
        195                 200                 205

Arg Gln Ile Val Val Glu Tyr Ser Asp Ile Arg Thr Leu Leu Val Ile
    210                 215                 220

Glu Pro Asp Ser Leu Ala Asn Leu Val Thr Asn Leu Gly Thr Pro Lys
225                 230                 235                 240

Cys Ala Asn Ala Gln Ser Ala Tyr Leu Glu Cys Ile Asn Tyr Ala Val
                245                 250                 255

Thr Gln Leu Asn Leu Pro Asn Val Ala Met Tyr Leu Asp Ala Gly His
            260                 265                 270

Ala Gly Trp Leu Gly Trp Pro Ala Asn Gln Asp Pro Ala Ala Gln Leu
        275                 280                 285

Phe Ala Asn Val Tyr Lys Asn Ala Ser Ser Pro Arg Ala Leu Arg Gly
    290                 295                 300

Leu Ala Thr Asn Val Ala Asn Tyr Asn Gly Trp Asn Ile Thr Ser Pro
305                 310                 315                 320

Pro Ser Tyr Thr Gln Gly Asn Ala Val Tyr Asn Glu Lys Leu Tyr Ile
                325                 330                 335

His Ala Ile Gly Arg Leu Leu Ala Asn His Gly Trp Ser Asn Ala Phe
            340                 345                 350

Phe Ile Thr Asp Gln Gly Arg Ser Gly Lys Gln Pro Thr Gly Gln Gln
        355                 360                 365

Gln Trp Gly Asp Trp Cys Asn Val Ile Gly Thr Gly Phe Gly Ile Arg
    370                 375                 380

Pro Ser Ala Asn Thr Gly Asp Ser Leu Leu Asp Ser Phe Val Trp Val
385                 390                 395                 400

```
Lys Pro Gly Gly Glu Cys Asp Gly Thr Ser Asp Ser Ala Pro Arg
                405                 410                 415

Phe Asp Ser His Cys Ala Leu Pro Asp Ala Leu Gln Pro Ala Pro Gln
            420                 425                 430

Ala Gly Ala Trp Phe Gln Ala Tyr Phe Val Gln Leu Leu Thr Asn Ala
        435                 440                 445

Asn Pro Ser Phe Leu
    450

<210> SEQ ID NO 18
<211> LENGTH: 506
<212> TYPE: PRT
<213> ORGANISM: Aspergillus fumigatus

<400> SEQUENCE: 18

Gln Gln Val Gly Thr Ser Gln Ala Glu Val His Pro Ser Met Thr Trp
1               5                   10                  15

Gln Ser Cys Thr Ala Gly Gly Ser Cys Thr Thr Asn Asn Gly Lys Val
            20                  25                  30

Val Ile Asp Ala Asn Trp Arg Trp Val His Lys Val Gly Asp Tyr Thr
        35                  40                  45

Asn Cys Tyr Thr Gly Asn Thr Trp Asp Thr Thr Ile Cys Pro Asp Asp
    50                  55                  60

Ala Thr Cys Ala Ser Asn Cys Ala Leu Glu Gly Ala Asn Tyr Glu Ser
65                  70                  75                  80

Thr Tyr Gly Val Thr Ala Ser Gly Asn Ser Leu Arg Leu Asn Phe Val
                85                  90                  95

Thr Thr Ser Gln Gln Lys Asn Ile Gly Ser Arg Leu Tyr Met Met Lys
            100                 105                 110

Asp Asp Ser Thr Tyr Glu Met Phe Lys Leu Leu Asn Gln Glu Phe Thr
        115                 120                 125

Phe Asp Val Asp Val Ser Asn Leu Pro Cys Gly Leu Asn Gly Ala Leu
    130                 135                 140

Tyr Phe Val Ala Met Asp Ala Asp Gly Gly Met Ser Lys Tyr Pro Thr
145                 150                 155                 160

Asn Lys Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Gln Pro Ser Ser Asn Asp Ala Asn Ala Gly Thr Gly Asn His Gly Ser
        195                 200                 205

Cys Cys Ala Glu Met Asp Ile Trp Glu Ala Asn Ser Ile Ser Thr Ala
    210                 215                 220

Phe Thr Pro His Pro Cys Asp Thr Pro Gly Gln Val Met Cys Thr Gly
225                 230                 235                 240

Asp Ala Cys Gly Gly Thr Tyr Ser Ser Asp Arg Tyr Gly Gly Thr Cys
                245                 250                 255

Asp Pro Asp Gly Cys Asp Phe Asn Ser Phe Arg Gln Gly Asn Lys Thr
            260                 265                 270

Phe Tyr Gly Pro Gly Met Thr Val Asp Thr Lys Ser Lys Phe Thr Val
        275                 280                 285

Val Thr Gln Phe Ile Thr Asp Asp Gly Thr Ser Ser Gly Thr Leu Lys
    290                 295                 300

Glu Ile Lys Arg Phe Tyr Val Gln Asn Gly Lys Val Ile Pro Asn Ser
305                 310                 315                 320
```

```
Glu Ser Thr Trp Thr Gly Val Ser Gly Asn Ser Ile Thr Thr Glu Tyr
                325                 330                 335

Cys Thr Ala Gln Lys Ser Leu Phe Gln Asp Gln Asn Val Phe Glu Lys
            340                 345                 350

His Gly Gly Leu Glu Gly Met Gly Ala Ala Leu Ala Gln Gly Met Val
        355                 360                 365

Leu Val Met Ser Leu Trp Asp Asp His Ser Ala Asn Met Leu Trp Leu
    370                 375                 380

Asp Ser Asn Tyr Pro Thr Thr Ala Ser Ser Thr Thr Pro Gly Val Ala
385                 390                 395                 400

Arg Gly Thr Cys Asp Ile Ser Ser Gly Val Pro Ala Asp Val Glu Ala
                405                 410                 415

Asn His Pro Asp Ala Tyr Val Val Tyr Ser Asn Ile Lys Val Gly Pro
            420                 425                 430

Ile Gly Ser Thr Phe Asn Ser Gly Gly Ser Asn Pro Gly Gly Gly Thr
        435                 440                 445

Thr Thr Thr Thr Thr Thr Gln Pro Thr Thr Thr Thr Thr Thr Ala Gly
    450                 455                 460

Asn Pro Gly Gly Thr Gly Val Ala Gln His Tyr Gly Gln Cys Gly Gly
465                 470                 475                 480

Ile Gly Trp Thr Gly Pro Thr Thr Cys Ala Ser Pro Tyr Thr Cys Gln
                485                 490                 495

Lys Leu Asn Asp Tyr Tyr Ser Gln Cys Leu
            500                 505

<210> SEQ ID NO 19
<211> LENGTH: 435
<212> TYPE: PRT
<213> ORGANISM: Aspergillus fumigatus

<400> SEQUENCE: 19

Gln Gln Thr Val Trp Gly Gln Cys Gly Gly Gln Gly Trp Ser Gly Pro
1               5                   10                  15

Thr Ser Cys Val Ala Gly Ala Ala Cys Ser Thr Leu Asn Pro Tyr Tyr
                20                  25                  30

Ala Gln Cys Ile Pro Gly Ala Thr Ala Thr Ser Thr Thr Leu Thr Thr
            35                  40                  45

Thr Thr Ala Ala Thr Thr Ser Gln Thr Thr Thr Lys Pro Thr Thr
    50                  55                  60

Thr Gly Pro Thr Thr Ser Ala Pro Thr Val Thr Ala Ser Gly Asn Pro
65                  70                  75                  80

Phe Ser Gly Tyr Gln Leu Tyr Ala Asn Pro Tyr Tyr Ser Ser Glu Val
                85                  90                  95

His Thr Leu Ala Met Pro Ser Leu Pro Ser Ser Leu Gln Pro Lys Ala
            100                 105                 110

Ser Ala Val Ala Glu Val Pro Ser Phe Val Trp Leu Asp Val Ala Ala
        115                 120                 125

Lys Val Pro Thr Met Gly Thr Tyr Leu Ala Asp Ile Gln Ala Lys Asn
    130                 135                 140

Lys Ala Gly Ala Asn Pro Pro Ile Ala Gly Ile Phe Val Val Tyr Asp
145                 150                 155                 160

Leu Pro Asp Arg Asp Cys Ala Ala Leu Ala Ser Asn Gly Glu Tyr Ser
                165                 170                 175

Ile Ala Asn Asn Gly Val Ala Asn Tyr Lys Ala Tyr Ile Asp Ala Ile
```

```
            180                 185                 190
Arg Ala Gln Leu Val Lys Tyr Ser Asp Val His Thr Ile Leu Val Ile
        195                 200                 205

Glu Pro Asp Ser Leu Ala Asn Leu Val Thr Asn Leu Asn Val Ala Lys
    210                 215                 220

Cys Ala Asn Ala Gln Ser Ala Tyr Leu Glu Cys Val Asp Tyr Ala Leu
225                 230                 235                 240

Lys Gln Leu Asn Leu Pro Asn Val Ala Met Tyr Leu Asp Ala Gly His
                245                 250                 255

Ala Gly Trp Leu Gly Trp Pro Ala Asn Leu Gly Pro Ala Ala Thr Leu
            260                 265                 270

Phe Ala Lys Val Tyr Thr Asp Ala Gly Ser Pro Ala Ala Val Arg Gly
        275                 280                 285

Leu Ala Thr Asn Val Ala Asn Tyr Asn Ala Trp Ser Leu Ser Thr Cys
    290                 295                 300

Pro Ser Tyr Thr Gln Gly Asp Pro Asn Cys Asp Glu Lys Lys Tyr Ile
305                 310                 315                 320

Asn Ala Met Ala Pro Leu Leu Lys Glu Ala Gly Phe Asp Ala His Phe
                325                 330                 335

Ile Met Asp Thr Ser Arg Asn Gly Val Gln Pro Thr Lys Gln Asn Ala
            340                 345                 350

Trp Gly Asp Trp Cys Asn Val Ile Gly Thr Gly Phe Gly Val Arg Pro
        355                 360                 365

Ser Thr Asn Thr Gly Asp Pro Leu Gln Asp Ala Phe Val Trp Ile Lys
    370                 375                 380

Pro Gly Gly Glu Ser Asp Gly Thr Ser Asn Ser Thr Ser Pro Arg Tyr
385                 390                 395                 400

Asp Ala His Cys Gly Tyr Ser Asp Ala Leu Gln Pro Ala Pro Glu Ala
                405                 410                 415

Gly Thr Trp Phe Gln Ala Tyr Phe Glu Gln Leu Leu Thr Asn Ala Asn
            420                 425                 430

Pro Ser Phe
        435

<210> SEQ ID NO 20
<211> LENGTH: 437
<212> TYPE: PRT
<213> ORGANISM: Trichoderma reesei

<400> SEQUENCE: 20

Gln Gln Pro Gly Thr Ser Thr Pro Glu Val His Pro Lys Leu Thr Thr
1               5                   10                  15

Tyr Lys Cys Thr Lys Ser Gly Cys Val Ala Gln Asp Thr Ser Val
            20                  25                  30

Val Leu Asp Trp Asn Tyr Arg Trp Met His Asp Ala Asn Tyr Asn Ser
        35                  40                  45

Cys Thr Val Asn Gly Gly Val Asn Thr Thr Leu Cys Pro Asp Glu Ala
    50                  55                  60

Thr Cys Gly Lys Asn Cys Phe Ile Glu Gly Val Asp Tyr Ala Ala Ser
65                  70                  75                  80

Gly Val Thr Thr Ser Gly Ser Ser Leu Thr Met Asn Gln Tyr Met Pro
                85                  90                  95

Ser Ser Ser Gly Gly Tyr Ser Ser Val Ser Pro Arg Leu Tyr Leu Leu
            100                 105                 110
```

Asp Ser Asp Gly Glu Tyr Val Met Leu Lys Leu Asn Gly Gln Glu Leu
            115                 120                 125

Ser Phe Asp Val Asp Leu Ser Ala Leu Pro Cys Gly Glu Asn Gly Ser
        130                 135                 140

Leu Tyr Leu Ser Gln Met Asp Glu Asn Gly Gly Ala Asn Gln Tyr Asn
145                 150                 155                 160

Thr Ala Gly Ala Asn Tyr Gly Ser Gly Tyr Cys Asp Ala Gln Cys Pro
                165                 170                 175

Val Gln Thr Trp Arg Asn Gly Thr Leu Asn Thr Ser His Gln Gly Phe
            180                 185                 190

Cys Cys Asn Glu Met Asp Ile Leu Glu Gly Asn Ser Arg Ala Asn Ala
        195                 200                 205

Leu Thr Pro His Ser Cys Thr Ala Thr Ala Cys Asp Ser Ala Gly Cys
210                 215                 220

Gly Phe Asn Pro Tyr Gly Ser Gly Tyr Lys Ser Tyr Tyr Gly Pro Gly
225                 230                 235                 240

Asp Thr Val Asp Thr Ser Lys Thr Phe Thr Ile Ile Thr Gln Phe Asn
                245                 250                 255

Thr Asp Asn Gly Ser Pro Ser Gly Asn Leu Val Ser Ile Thr Arg Lys
            260                 265                 270

Tyr Gln Gln Asn Gly Val Asp Ile Pro Ser Ala Gln Pro Gly Gly Asp
        275                 280                 285

Thr Ile Ser Ser Cys Pro Ser Ala Ser Ala Tyr Gly Gly Leu Ala Thr
290                 295                 300

Met Gly Lys Ala Leu Ser Ser Gly Met Val Leu Val Phe Ser Ile Trp
305                 310                 315                 320

Asn Asp Asn Ser Gln Tyr Met Asn Trp Leu Asp Ser Gly Asn Ala Gly
                325                 330                 335

Pro Cys Ser Ser Thr Glu Gly Asn Pro Ser Asn Ile Leu Ala Asn Asn
            340                 345                 350

Pro Asn Thr His Val Val Phe Ser Asn Ile Arg Trp Gly Asp Ile Gly
        355                 360                 365

Ser Thr Thr Asn Ser Thr Ala Pro Pro Pro Pro Ala Ser Ser Thr
370                 375                 380

Thr Phe Ser Thr Thr Arg Arg Ser Ser Thr Thr Ser Ser Ser Pro Ser
385                 390                 395                 400

Cys Thr Gln Thr His Trp Gly Gln Cys Gly Gly Ile Gly Tyr Ser Gly
                405                 410                 415

Cys Lys Thr Cys Thr Ser Gly Thr Thr Cys Gln Tyr Ser Asn Asp Tyr
            420                 425                 430

Tyr Ser Gln Cys Leu
        435

<210> SEQ ID NO 21
<211> LENGTH: 397
<212> TYPE: PRT
<213> ORGANISM: Trichoderma reesei

<400> SEQUENCE: 21

Gln Gln Thr Val Trp Gly Gln Cys Gly Gly Ile Gly Trp Ser Gly Pro
1               5                   10                  15

Thr Asn Cys Ala Pro Gly Ser Ala Cys Ser Thr Leu Asn Pro Tyr Tyr
            20                  25                  30

Ala Gln Cys Ile Pro Gly Ala Thr Thr Ile Thr Thr Ser Thr Arg Pro
        35                  40                  45

```
Pro Ser Gly Pro Thr Thr Thr Arg Ala Thr Ser Thr Ser Ser Ser
    50                  55                  60

Thr Pro Pro Thr Ser Ser Gly Val Arg Phe Ala Gly Val Asn Ile Ala
65                  70                  75                  80

Gly Phe Asp Phe Gly Cys Thr Thr Asp Gly Thr Cys Val Thr Ser Lys
                85                  90                  95

Val Tyr Pro Pro Leu Lys Asn Phe Thr Gly Ser Asn Asn Tyr Pro Asp
                100                 105                 110

Gly Ile Gly Gln Met Gln His Phe Val Asn Glu Asp Gly Met Thr Ile
            115                 120                 125

Phe Arg Leu Pro Val Gly Trp Gln Tyr Leu Val Asn Asn Asn Leu Gly
        130                 135                 140

Gly Asn Leu Asp Ser Thr Ser Ile Ser Lys Tyr Asp Gln Leu Val Gln
145                 150                 155                 160

Gly Cys Leu Ser Leu Gly Ala Tyr Cys Ile Val Asp Ile His Asn Tyr
                165                 170                 175

Ala Arg Trp Asn Gly Gly Ile Ile Gly Gln Gly Gly Pro Thr Asn Ala
                180                 185                 190

Gln Phe Thr Ser Leu Trp Ser Gln Leu Ala Ser Lys Tyr Ala Ser Gln
            195                 200                 205

Ser Arg Val Trp Phe Gly Ile Met Asn Glu Pro His Asp Val Asn Ile
        210                 215                 220

Asn Thr Trp Ala Ala Thr Val Gln Glu Val Val Thr Ala Ile Arg Asn
225                 230                 235                 240

Ala Gly Ala Thr Ser Gln Phe Ile Ser Leu Pro Gly Asn Asp Trp Gln
                245                 250                 255

Ser Ala Gly Ala Phe Ile Ser Asp Gly Ser Ala Ala Leu Ser Gln
            260                 265                 270

Val Thr Asn Pro Asp Gly Ser Thr Thr Asn Leu Ile Phe Asp Val His
        275                 280                 285

Lys Tyr Leu Asp Ser Asp Asn Ser Gly Thr His Ala Glu Cys Thr Thr
        290                 295                 300

Asn Asn Ile Asp Gly Ala Phe Ser Pro Leu Ala Thr Trp Leu Arg Gln
305                 310                 315                 320

Asn Asn Arg Gln Ala Ile Leu Thr Glu Thr Gly Gly Gly Asn Val Gln
                325                 330                 335

Ser Cys Ile Gln Asp Met Cys Gln Gln Ile Gln Tyr Leu Asn Gln Asn
            340                 345                 350

Ser Asp Val Tyr Leu Gly Tyr Val Gly Trp Gly Ala Gly Ser Phe Asp
        355                 360                 365

Ser Thr Tyr Val Leu Thr Glu Thr Pro Thr Ser Ser Gly Asn Ser Trp
    370                 375                 380

Thr Asp Thr Ser Leu Val Ser Ser Cys Leu Ala Arg Lys
385                 390                 395

<210> SEQ ID NO 22
<211> LENGTH: 218
<212> TYPE: PRT
<213> ORGANISM: Trichoderma reesei

<400> SEQUENCE: 22

Gln Thr Ser Cys Asp Gln Trp Ala Thr Phe Thr Gly Asn Gly Tyr Thr
1               5                   10                  15

Val Ser Asn Asn Leu Trp Gly Ala Ser Ala Gly Ser Gly Phe Gly Cys
```

```
            20                  25                  30
Val Thr Ala Val Ser Leu Ser Gly Gly Ala Ser Trp His Ala Asp Trp
         35                  40                  45

Gln Trp Ser Gly Gly Gln Asn Asn Val Lys Ser Tyr Gln Asn Ser Gln
 50                  55                  60

Ile Ala Ile Pro Gln Lys Arg Thr Val Asn Ser Ile Ser Ser Met Pro
 65                  70                  75                  80

Thr Thr Ala Ser Trp Ser Tyr Ser Gly Ser Asn Ile Arg Ala Asn Val
                 85                  90                  95

Ala Tyr Asp Leu Phe Thr Ala Ala Asn Pro Asn His Val Thr Tyr Ser
             100                 105                 110

Gly Asp Tyr Glu Leu Met Ile Trp Leu Gly Lys Tyr Gly Asp Ile Gly
             115                 120                 125

Pro Ile Gly Ser Ser Gln Gly Thr Val Asn Val Gly Gly Gln Ser Trp
             130                 135                 140

Thr Leu Tyr Tyr Gly Tyr Asn Gly Ala Met Gln Val Tyr Ser Phe Val
145                 150                 155                 160

Ala Gln Thr Asn Thr Thr Asn Tyr Ser Gly Asp Val Lys Asn Phe Phe
                 165                 170                 175

Asn Tyr Leu Arg Asp Asn Lys Gly Tyr Asn Ala Ala Gly Gln Tyr Val
             180                 185                 190

Leu Ser Tyr Gln Phe Gly Thr Glu Pro Phe Thr Gly Ser Gly Thr Leu
             195                 200                 205

Asn Val Ala Ser Trp Thr Ala Ser Ile Asn
             210                 215

<210> SEQ ID NO 23
<211> LENGTH: 225
<212> TYPE: PRT
<213> ORGANISM: Trichoderma reesei

<400> SEQUENCE: 23

Tyr Lys Ala Thr Thr Thr Arg Tyr Tyr Asp Gly Gln Glu Gly Ala Cys
 1                   5                  10                  15

Gly Cys Gly Ser Ser Ser Gly Ala Phe Pro Trp Gln Leu Gly Ile Gly
                 20                  25                  30

Asn Gly Val Tyr Thr Ala Ala Gly Ser Gln Ala Leu Phe Asp Thr Ala
             35                  40                  45

Gly Ala Ser Trp Cys Gly Ala Gly Cys Gly Lys Cys Tyr Gln Leu Thr
 50                  55                  60

Ser Thr Gly Gln Ala Pro Cys Ser Ser Cys Gly Thr Gly Gly Ala Ala
 65                  70                  75                  80

Gly Gln Ser Ile Ile Val Met Val Thr Asn Leu Cys Pro Asn Asn Gly
                 85                  90                  95

Asn Ala Gln Trp Cys Pro Val Val Gly Gly Thr Asn Gln Tyr Gly Tyr
             100                 105                 110

Ser Tyr His Phe Asp Ile Met Ala Gln Asn Glu Ile Phe Gly Asp Asn
             115                 120                 125

Val Val Val Asp Phe Glu Pro Ile Ala Cys Pro Gly Gln Ala Ala Ser
             130                 135                 140

Asp Trp Gly Thr Cys Leu Cys Val Gly Gln Gln Glu Thr Asp Pro Thr
145                 150                 155                 160

Pro Val Leu Gly Asn Asp Thr Gly Ser Thr Pro Pro Gly Ser Ser Pro
                 165                 170                 175
```

```
Pro Ala Thr Ser Ser Pro Pro Ser Gly Gly Gln Gln Thr Leu
            180                 185                 190

Tyr Gly Gln Cys Gly Gly Ala Gly Trp Thr Gly Pro Thr Cys Gln
        195                 200                 205

Ala Pro Gly Thr Cys Lys Val Gln Asn Gln Trp Tyr Ser Gln Cys Leu
    210                 215                 220

Pro
225

<210> SEQ ID NO 24
<211> LENGTH: 373
<212> TYPE: PRT
<213> ORGANISM: Mycelophthora thermophila

<400> SEQUENCE: 24

Gln Ser Gly Pro Trp Gln Gln Cys Gly Gly Ile Gly Trp Gln Gly Ser
1               5                   10                  15

Thr Asp Cys Val Ser Gly Tyr His Cys Val Tyr Gln Asn Asp Trp Tyr
            20                  25                  30

Ser Gln Cys Val Pro Gly Ala Ala Ser Thr Thr Leu Gln Thr Ser Thr
        35                  40                  45

Thr Ser Arg Pro Thr Ala Thr Ser Thr Ala Pro Pro Ser Ser Thr Thr
    50                  55                  60

Ser Pro Ser Lys Gly Lys Leu Lys Trp Leu Gly Ser Asn Glu Ser Gly
65                  70                  75                  80

Ala Glu Phe Gly Glu Gly Asn Tyr Pro Gly Leu Trp Gly Lys His Phe
                85                  90                  95

Ile Phe Pro Ser Thr Ser Ala Ile Gln Thr Leu Ile Asn Asp Gly Tyr
            100                 105                 110

Asn Ile Phe Arg Ile Asp Phe Ser Met Glu Arg Leu Val Pro Asn Gln
        115                 120                 125

Leu Thr Ser Ser Phe Asp Gln Gly Tyr Leu Arg Asn Leu Thr Glu Val
    130                 135                 140

Val Asn Phe Val Thr Asn Ala Gly Lys Tyr Ala Val Leu Asp Pro His
145                 150                 155                 160

Asn Tyr Gly Arg Tyr Tyr Gly Asn Ile Ile Thr Asp Thr Asn Ala Phe
                165                 170                 175

Arg Thr Phe Trp Thr Asn Leu Ala Lys Gln Phe Ala Ser Asn Ser Leu
            180                 185                 190

Val Ile Phe Asp Thr Asn Asn Glu Tyr Asn Thr Met Asp Gln Thr Leu
        195                 200                 205

Val Leu Asn Leu Asn Gln Ala Ala Ile Asp Gly Ile Arg Ala Ala Gly
    210                 215                 220

Ala Thr Ser Gln Tyr Ile Phe Val Glu Gly Asn Ala Trp Ser Gly Ala
225                 230                 235                 240

Trp Ser Trp Asn Thr Thr Asn Thr Asn Met Ala Ala Leu Thr Asp Pro
                245                 250                 255

Gln Asn Lys Ile Val Tyr Glu Met His Gln Tyr Leu Asp Ser Asp Ser
            260                 265                 270

Ser Gly Thr His Ala Glu Cys Val Ser Ser Thr Ile Gly Ala Gln Arg
        275                 280                 285

Val Val Gly Ala Thr Gln Trp Leu Arg Ala Asn Gly Lys Leu Gly Val
    290                 295                 300

Leu Gly Glu Phe Ala Gly Gly Ala Asn Ala Val Cys Gln Gln Ala Val
305                 310                 315                 320
```

Thr Gly Leu Leu Asp His Leu Gln Asp Asn Ser Asp Val Trp Leu Gly
            325                 330                 335

Ala Leu Trp Trp Ala Ala Gly Pro Trp Trp Gly Asp Tyr Met Tyr Ser
            340                 345                 350

Phe Glu Pro Pro Ser Gly Thr Gly Tyr Val Asn Tyr Asn Ser Ile Leu
            355                 360                 365

Lys Lys Tyr Leu Pro
        370

<210> SEQ ID NO 25
<211> LENGTH: 475
<212> TYPE: PRT
<213> ORGANISM: Penicillium pinophalum

<400> SEQUENCE: 25

Gln Gln Ala Pro Thr Pro Asp Asn Leu Ala Ser Leu Pro Thr Trp Lys
1               5                   10                  15

Cys Thr Thr Ser Gly Gly Cys Val Gln Gln Ser Thr Ser Ile Val Val
            20                  25                  30

Asp Trp Val Tyr His Trp Ile His Thr Val Asn Gly Ser Thr Ser Cys
        35                  40                  45

Thr Thr Ser Ser Gly Leu Asp Pro Thr Leu Cys Gly Thr Glu Glu Glu
    50                  55                  60

Cys Tyr Thr Asn Cys Glu Ile Ser Pro Ala Thr Tyr Asp Gly Leu Gly
65                  70                  75                  80

Ile Lys Thr Ser Gly Asn Ala Leu Thr Leu Asn Gln Tyr Val Thr Ser
                85                  90                  95

Asn Gly Thr Thr Ser Asn Ala Ser Pro Arg Val Tyr Leu Leu Asp Pro
            100                 105                 110

Ala Gly Lys Asn Tyr Glu Met Leu Gln Leu Leu Gly Gln Glu Ile Ser
        115                 120                 125

Phe Asp Val Asp Ala Ser Asn Leu Pro Cys Gly Glu Asn Gly Ala Leu
    130                 135                 140

Tyr Leu Ser Glu Met Asp Ala Thr Gly Gly Arg Ser Gln Tyr Asn Pro
145                 150                 155                 160

Ala Gly Ala Ser Tyr Gly Ser Gly Tyr Cys Asp Ala Gln Cys Gly Ser
                165                 170                 175

Ser Ser Trp Phe Asn Gly Ser Ile Asn Ser Ala Gly Leu Gly Ser Cys
            180                 185                 190

Cys Asn Glu Met Asp Leu Trp Glu Ala Asn Gly Glu Ala Thr Ala Leu
        195                 200                 205

Thr Pro His Pro Cys Ser Val Asp Gly Pro Tyr Gly Cys Ser Gly Ser
    210                 215                 220

Ala Cys Gly Ser Thr Gly Val Cys Asp Lys Asn Gly Cys Gly Phe Asn
225                 230                 235                 240

Pro Tyr Ala Leu Gly Asn His Ser Tyr Tyr Gly Pro Gly Leu Thr Val
                245                 250                 255

Asp Thr Ser Lys Pro Phe Thr Val Thr Thr Gln Phe Val Thr Asn Asp
            260                 265                 270

Gly Thr Lys Thr Gly Thr Leu Thr Glu Ile Arg Arg Ser Tyr Thr Gln
        275                 280                 285

Asn Gly Lys Val Ile Ala Asn Ala Val Ala Ser Ser Ser Ser Gly Phe
    290                 295                 300

Ser Gly Gln Ser Ser Ile Thr Glu Ser Phe Cys Thr Ala Met Asp Ser

```
            305                 310                 315                 320
    Glu Ala Gly Thr Leu Gly Gly Leu Thr Thr Met Gly Glu Ala Leu Gly
                        325                 330                 335

Arg Gly Met Val Leu Ile Phe Ser Ile Trp Asn Asp Ala Gly Gly Tyr
                        340                 345                 350

Met Asn Trp Leu Asp Ser Gly Ser Ser Gly Pro Cys Ser Ser Thr Ala
                        355                 360                 365

Gly Ile Pro Ser Thr Ile Gln Ala Asn Asp Pro Gly Thr Ser Val Thr
                        370                 375                 380

Phe Ser Asn Ile Lys Trp Gly Asp Ile Gly Ser Thr Gly Ser Gly Thr
    385                 390                 395                 400

Gly Gly Ser Ser Ser Ser Ser Ser Thr Ser Thr Ser Pro Lys Thr
                        405                 410                 415

Thr Ser Thr Thr Thr Thr Ser Ala Thr Thr Lys Thr Ser Ala Thr Thr
                        420                 425                 430

Thr Thr Thr Ser Thr Gly Val Thr Gln Thr His Tyr Gly Gln Cys Gly
                        435                 440                 445

Gly Met Tyr Tyr Thr Gly Pro Thr Val Cys Ala Ser Pro Tyr Thr Cys
                        450                 455                 460

Gln Val Gln Asn Pro Tyr Tyr Ser Gln Cys Leu
    465                 470                 475

<210> SEQ ID NO 26
<211> LENGTH: 367
<212> TYPE: PRT
<213> ORGANISM: Aspergillus niger

<400> SEQUENCE: 26

Asn Val Ser Thr Ala Leu Pro Lys Ala Ser Pro Ala Pro Ser Thr Ser
    1               5                   10                  15

Ser Ser Ala Ala Ser Thr Ser Phe Ala Ser Thr Ser Gly Leu Gln Phe
                        20                  25                  30

Thr Ile Asp Gly Glu Thr Gly Tyr Phe Ala Gly Thr Asn Ser Tyr Trp
                        35                  40                  45

Ile Gly Phe Leu Thr Asp Asn Ser Asp Val Asp Leu Val Met Ser His
                50                  55                  60

Leu Lys Ser Ser Gly Leu Lys Ile Leu Arg Val Trp Gly Phe Asn Asp
    65                  70                  75                  80

Val Thr Ser Gln Pro Ser Ser Gly Thr Val Trp Tyr Gln Leu His Gln
                        85                  90                  95

Asp Gly Lys Ser Thr Ile Asn Thr Gly Ala Asp Gly Leu Gln Arg Leu
                        100                 105                 110

Asp Tyr Val Val Ser Ser Ala Glu Gln His Asp Ile Lys Leu Ile Ile
                        115                 120                 125

Asn Phe Val Asn Tyr Trp Thr Asp Tyr Gly Gly Met Ser Ala Tyr Val
                        130                 135                 140

Ser Ala Tyr Gly Gly Ser Asp Glu Thr Asp Phe Tyr Thr Ser Asp Thr
    145                 150                 155                 160

Ile Gln Ser Ala Tyr Gln Thr Tyr Ile Lys Thr Val Val Glu Arg Tyr
                        165                 170                 175

Ser Asn Ser Ser Ala Val Phe Ala Trp Glu Leu Ala Asn Glu Pro Arg
                        180                 185                 190

Cys Pro Ser Cys Asp Thr Ser Val Leu Tyr Asn Trp Ile Glu Lys Thr
                        195                 200                 205
```

```
Ser Lys Phe Ile Lys Gly Leu Asp Ala Asp His Met Val Cys Ile Gly
    210                 215                 220

Asp Glu Gly Phe Gly Leu Asn Ile Asp Ser Asp Gly Ser Tyr Pro Tyr
225                 230                 235                 240

Gln Phe Ser Glu Gly Leu Asn Phe Thr Met Asn Leu Gly Ile Asp Thr
                245                 250                 255

Ile Asp Phe Gly Thr Leu His Leu Tyr Pro Asp Ser Trp Gly Thr Ser
                260                 265                 270

Asp Asp Trp Gly Asn Gly Trp Ile Thr Ala His Gly Ala Ala Cys Lys
            275                 280                 285

Ala Ala Gly Lys Pro Cys Leu Leu Glu Glu Tyr Gly Val Thr Ser Asn
290                 295                 300

His Cys Ser Val Glu Ser Pro Trp Gln Lys Thr Ala Leu Asn Thr Thr
305                 310                 315                 320

Gly Val Gly Ala Asp Leu Phe Trp Gln Tyr Gly Asp Asp Leu Ser Thr
                325                 330                 335

Gly Lys Ser Pro Asp Asp Gly Asn Thr Ile Tyr Tyr Gly Thr Ser Asp
                340                 345                 350

Tyr Glu Cys Leu Val Thr Asp His Val Ala Ala Ile Gly Ser Ala
                355                 360                 365
```

<210> SEQ ID NO 27
<211> LENGTH: 418
<212> TYPE: PRT
<213> ORGANISM: Trichoderma reesei

<400> SEQUENCE: 27

```
Ala Val Leu Gln Pro Val Pro Arg Ala Ser Phe Val Thr Ile Ser
1               5                   10                  15

Gly Thr Gln Phe Asn Ile Asp Gly Lys Val Gly Tyr Phe Ala Gly Thr
                20                  25                  30

Asn Cys Tyr Trp Cys Ser Phe Leu Thr Asn His Ala Asp Val Asp Ser
                35                  40                  45

Thr Phe Ser His Ile Ser Ser Gly Leu Lys Val Val Arg Val Trp
        50                  55                  60

Gly Phe Asn Asp Val Asn Thr Gln Pro Ser Pro Gly Gln Ile Trp Phe
65                  70                  75                  80

Gln Lys Leu Ser Ala Thr Gly Ser Thr Ile Asn Thr Gly Ala Asp Gly
                85                  90                  95

Leu Gln Thr Leu Asp Tyr Val Val Gln Ser Ala Glu Gln His Asn Leu
                100                 105                 110

Lys Leu Ile Ile Pro Phe Val Asn Asn Trp Ser Asp Tyr Gly Gly Ile
            115                 120                 125

Asn Ala Tyr Val Asn Ala Phe Gly Gly Asn Ala Thr Thr Trp Tyr Thr
        130                 135                 140

Asn Thr Ala Ala Gln Thr Gln Tyr Arg Lys Tyr Val Gln Ala Val Val
145                 150                 155                 160

Ser Arg Tyr Ala Asn Ser Thr Ala Ile Phe Ala Trp Glu Leu Gly Asn
                165                 170                 175

Glu Pro Arg Cys Asn Gly Cys Ser Thr Asp Val Ile Val Gln Trp Ala
            180                 185                 190

Thr Ser Val Ser Gln Tyr Val Lys Ser Leu Asp Ser Asn His Leu Val
        195                 200                 205

Thr Leu Gly Asp Glu Gly Leu Gly Leu Ser Thr Gly Asp Gly Ala Tyr
    210                 215                 220
```

```
Pro Tyr Thr Tyr Gly Glu Gly Thr Asp Phe Ala Lys Asn Val Gln Ile
225                 230                 235                 240

Lys Ser Leu Asp Phe Gly Thr Phe His Leu Tyr Pro Asp Ser Trp Gly
            245                 250                 255

Thr Asn Tyr Thr Trp Gly Asn Gly Trp Ile Gln Thr His Ala Ala Ala
        260                 265                 270

Cys Leu Ala Ala Gly Lys Pro Cys Val Phe Glu Glu Tyr Gly Ala Gln
        275                 280                 285

Gln Asn Pro Cys Thr Asn Glu Ala Pro Trp Gln Thr Thr Ser Leu Thr
        290                 295                 300

Thr Arg Gly Met Gly Gly Asp Met Phe Trp Gln Trp Gly Asp Thr Phe
305                 310                 315                 320

Ala Asn Gly Ala Gln Ser Asn Ser Asp Pro Tyr Thr Val Trp Tyr Asn
            325                 330                 335

Ser Ser Asn Trp Gln Cys Leu Val Lys Asn His Val Asp Ala Ile Asn
        340                 345                 350

Gly Gly Thr Thr Thr Pro Pro Val Ser Thr Thr Thr Thr Ser
        355                 360                 365

Ser Arg Thr Ser Ser Thr Pro Pro Pro Gly Gly Ser Cys Ser Pro
370                 375                 380

Leu Tyr Gly Gln Cys Gly Gly Ser Gly Tyr Thr Gly Pro Thr Cys Cys
385                 390                 395                 400

Ala Gln Gly Thr Cys Ile Tyr Ser Asn Tyr Trp Tyr Ser Gln Cys Leu
                405                 410                 415

Asn Thr

<210> SEQ ID NO 28
<211> LENGTH: 381
<212> TYPE: PRT
<213> ORGANISM: Aspergillus fumigatus

<400> SEQUENCE: 28

Val Tyr Gly Ala Gly Leu Asn Thr Ala Ala Lys Ala Lys Gly Leu Lys
1               5                   10                  15

Tyr Phe Gly Ser Ala Thr Asp Asn Pro Glu Leu Thr Asp Ser Ala Tyr
            20                  25                  30

Val Ala Gln Leu Ser Asn Thr Asp Asp Phe Gly Gln Ile Thr Pro Gly
        35                  40                  45

Asn Ser Met Lys Trp Asp Ala Thr Glu Pro Ser Gln Asn Ser Phe Ser
50                  55                  60

Phe Ala Asn Gly Asp Ala Val Val Asn Leu Ala Asn Lys Asn Gly Gln
65                  70                  75                  80

Leu Met Arg Cys His Thr Leu Val Trp His Ser Gln Leu Pro Asn Trp
                85                  90                  95

Val Ser Ser Gly Ser Trp Thr Asn Ala Thr Leu Leu Ala Ala Met Lys
            100                 105                 110

Asn His Ile Thr Asn Val Val Thr His Tyr Lys Gly Lys Cys Tyr Ala
        115                 120                 125

Trp Asp Val Val Asn Glu Ala Leu Asn Glu Asp Gly Thr Phe Arg Asn
    130                 135                 140

Ser Val Phe Tyr Gln Ile Ile Gly Pro Ala Tyr Ile Pro Ile Ala Phe
145                 150                 155                 160

Ala Thr Ala Ala Ala Ala Asp Pro Asp Val Lys Leu Tyr Tyr Asn Asp
                165                 170                 175
```

```
Tyr Asn Ile Glu Tyr Ser Gly Ala Lys Ala Thr Ala Ala Gln Asn Ile
            180                 185                 190

Val Lys Met Ile Lys Ala Tyr Gly Ala Lys Ile Asp Gly Val Gly Leu
        195                 200                 205

Gln Ala His Phe Ile Val Gly Ser Thr Pro Ser Gln Ser Asp Leu Thr
    210                 215                 220

Thr Val Leu Lys Gly Tyr Thr Ala Leu Gly Val Glu Val Ala Tyr Thr
225                 230                 235                 240

Glu Leu Asp Ile Arg Met Gln Leu Pro Ser Thr Ala Ala Lys Leu Ala
                245                 250                 255

Gln Gln Ser Thr Asp Phe Gln Gly Val Ala Ala Ala Cys Val Ser Thr
            260                 265                 270

Thr Gly Cys Val Gly Val Thr Ile Trp Asp Trp Thr Asp Lys Tyr Ser
        275                 280                 285

Trp Val Pro Ser Val Phe Gln Gly Tyr Gly Ala Pro Leu Pro Trp Asp
    290                 295                 300

Glu Asn Tyr Val Lys Lys Pro Ala Tyr Asp Gly Leu Met Ala Gly Leu
305                 310                 315                 320

Gly Ala Ser Gly Ser Gly Thr Thr Thr Thr Thr Thr Thr Thr Ser Thr
                325                 330                 335

Thr Thr Gly Gly Thr Asp Pro Thr Gly Val Ala Gln Lys Trp Gly Gln
            340                 345                 350

Cys Gly Gly Ile Gly Trp Thr Gly Pro Thr Thr Cys Val Ser Gly Thr
        355                 360                 365

Thr Cys Gln Lys Leu Asn Asp Trp Tyr Ser Gln Cys Leu
    370                 375                 380

<210> SEQ ID NO 29
<211> LENGTH: 388
<212> TYPE: PRT
<213> ORGANISM: Penicillium pinophilum

<400> SEQUENCE: 29

Gln Leu Asn Thr Ala Ala Lys Ala Ala Gly Leu Leu Tyr Phe Gly Thr
1               5                   10                  15

Ala Val Asp Asn Pro Asp Leu Ser Asp Ser Lys Tyr Ile Ala Asn Leu
            20                  25                  30

Glu Thr Ala Asp Phe Gly Gln Ile Thr Pro Ala Asn Ala Met Lys Trp
        35                  40                  45

Gln Pro Thr Glu Pro Ser Gln Gly Ser Tyr Thr Phe Thr Gln Gly Asp
    50                  55                  60

Gln Ile Ala Ser Leu Ala Lys Ser Asn Asn Asp Tyr Leu Arg Cys His
65                  70                  75                  80

Asn Leu Val Trp Tyr Asn Gln Leu Pro Ser Tyr Val Thr Ser Gly Ser
                85                  90                  95

Trp Thr Asn Ala Thr Leu Ile Ala Ala Leu Lys Glu His Ile Asn Gly
            100                 105                 110

Val Val Thr His Tyr Lys Gly Gln Cys Tyr Ala Trp Asp Val Val Asn
        115                 120                 125

Glu Ala Leu Asn Glu Asp Gly Thr Tyr Arg Gln Asn Val Phe Tyr Gln
    130                 135                 140

Tyr Ile Gly Glu Ala Tyr Ile Pro Ile Ala Phe Ala Ala Ala Ala Ala
145                 150                 155                 160

Ala Asp Pro Asn Ala Lys Leu Tyr Tyr Asn Asp Tyr Asn Ile Glu Tyr
```

```
                      165                 170                 175
Ala Gly Ser Lys Ala Thr Gly Ala Gln Arg Ile Val Lys Leu Ile Gln
                180                 185                 190

Ala Ala Gly Gly Arg Ile Asp Gly Val Gly Leu Gln Ser His Phe Ile
            195                 200                 205

Val Gly Gln Thr Pro Ser Leu Ala Thr Gln Lys Ala Asn Met Ala Ala
        210                 215                 220

Phe Thr Ala Leu Gly Val Asp Val Ala Ile Thr Glu Leu Asp Ile Arg
225                 230                 235                 240

Met Thr Leu Pro Asp Thr Ser Ala Leu Gln Thr Gln Gln Ser Thr Asp
                245                 250                 255

Tyr Gln Thr Thr Thr Ala Cys Val Gln Thr Lys Gly Cys Val Gly
                260                 265                 270

Ile Thr Leu Trp Asp Tyr Thr Asp Lys Tyr Ser Trp Val Pro Gly Thr
                275                 280                 285

Phe Ser Gly Gln Gly Asp Ala Cys Pro Trp Asp Ser Asn Tyr Asn Lys
            290                 295                 300

Lys Pro Ala Tyr Tyr Gly Ile Leu Ala Gly Leu Gln Ser Gly Thr Gly
305                 310                 315                 320

Ser Ser Ser Ser Thr Ser Ser Thr Thr Leu Thr Thr Thr Thr Thr Pro
                325                 330                 335

Thr Thr Ala Ser Ser Thr Thr Ser Thr Thr Ser Thr Ser Ala Thr Ser
                340                 345                 350

Gly Ala Ala His Trp Gly Gln Cys Gly Gly Ile Gly Trp Ser Gly Pro
                355                 360                 365

Thr Ile Cys Val Ser Pro Tyr Thr Cys Gln Val Leu Asn Pro Tyr Tyr
            370                 375                 380

Ser Gln Cys Leu
385

<210> SEQ ID NO 30
<211> LENGTH: 380
<212> TYPE: PRT
<213> ORGANISM: Penicillium

<400> SEQUENCE: 30

Ala Gly Leu Asn Thr Ala Ala Lys Ala Ile Gly Leu Lys Tyr Phe Gly
1               5                  10                  15

Thr Ala Thr Asp Asn Pro Glu Leu Ser Asp Thr Ala Tyr Glu Thr Glu
                20                  25                  30

Leu Asn Asn Thr Gln Asp Phe Gly Gln Leu Thr Pro Ala Asn Ser Met
            35                  40                  45

Lys Trp Asp Ala Thr Glu Pro Gln Gln Asn Thr Phe Thr Phe Ser Gly
        50                  55                  60

Gly Asp Gln Ile Ala Asn Leu Ala Lys Ala Asn Gly Gln Met Leu Arg
65                  70                  75                  80

Cys His Asn Leu Val Trp Tyr Asn Gln Leu Pro Ser Trp Val Thr Gly
                85                  90                  95

Gly Ser Trp Thr Asn Glu Thr Leu Leu Ala Ala Met Lys Asn His Ile
            100                 105                 110

Thr Asn Val Val Thr His Tyr Lys Gly Gln Cys Tyr Ala Trp Asp Val
        115                 120                 125

Val Asn Glu Ala Leu Asn Asp Asp Gly Thr Tyr Arg Ser Asn Val Phe
130                 135                 140
```

Tyr Gln Tyr Ile Gly Glu Ala Tyr Ile Pro Ile Ala Phe Ala Thr Ala
145                 150                 155                 160

Ala Ala Ala Asp Pro Asp Ala Lys Leu Tyr Tyr Asn Asp Tyr Asn Ile
            165                 170                 175

Glu Tyr Pro Gly Ala Lys Ala Thr Ala Ala Gln Asn Ile Val Lys Leu
            180                 185                 190

Val Gln Ser Tyr Gly Ala Arg Ile Asp Gly Val Gly Leu Gln Ser His
            195                 200                 205

Phe Ile Val Gly Gln Thr Pro Ser Thr Ser Ala Gln Gln Asn Met
210                 215                 220

Ala Ala Phe Thr Ala Leu Gly Val Glu Val Ala Ile Thr Glu Leu Asp
225                 230                 235                 240

Ile Arg Met Gln Leu Pro Glu Thr Ser Ala Gln Leu Thr Gln Gln Ala
            245                 250                 255

Thr Asp Tyr Gln Ser Thr Val Gln Ala Cys Val Asn Thr Asp Ser Cys
            260                 265                 270

Val Gly Ile Thr Leu Trp Asp Trp Thr Asp Lys Tyr Ser Trp Val Pro
            275                 280                 285

Ser Thr Phe Ser Gly Trp Gly Asp Ala Cys Pro Trp Asp Asp Asn Tyr
290                 295                 300

Gln Lys Lys Pro Ala Tyr Asn Gly Ile Leu Thr Ala Leu Gly Gly Thr
305                 310                 315                 320

Pro Ser Ser Ser Thr Ser Tyr Thr Leu Thr Pro Thr Thr Thr Ser Ser
            325                 330                 335

Gly Gly Ser Gly Ser Pro Thr Asp Val Ala Gln His Trp Glu Gln Cys
            340                 345                 350

Gly Gly Leu Gly Trp Thr Gly Pro Thr Val Cys Ala Ser Gly Phe Thr
            355                 360                 365

Cys Thr Val Ile Asn Glu Tyr Tyr Ser Gln Cys Leu
            370                 375                 380

<210> SEQ ID NO 31
<211> LENGTH: 379
<212> TYPE: PRT
<213> ORGANISM: Trichophaea saccata

<400> SEQUENCE: 31

Gln Val Ala Val Trp Gly Gln Cys Gly Gly Ile Gly Tyr Ser Gly Ser
1               5                   10                  15

Thr Thr Cys Ala Ala Gly Thr Cys Val Lys Leu Asn Asp Tyr Tyr
            20                  25                  30

Ser Gln Cys Gln Pro Gly Gly Thr Thr Leu Thr Thr Thr Lys Pro
        35                  40                  45

Ala Thr Thr Thr Thr Thr Thr Ala Thr Ser Pro Ser Ser Pro
50                  55                  60

Gly Leu Asn Ala Leu Ala Gln Lys Ser Gly Arg Tyr Phe Gly Ser Ala
65                  70                  75                  80

Thr Asp Asn Pro Glu Leu Ser Asp Ala Ala Tyr Ile Ala Ile Leu Ser
            85                  90                  95

Asn Lys Asn Glu Phe Gly Ile Ile Thr Pro Gly Asn Ser Met Lys Trp
            100                 105                 110

Asp Ala Thr Glu Pro Ser Arg Gly Ser Phe Ser Phe Thr Gly Gly Gln
            115                 120                 125

Gln Ile Val Asp Phe Ala Gln Gly Asn Gly Gln Ala Ile Arg Gly His
130                 135                 140

Thr Leu Val Trp Tyr Ser Gln Leu Pro Ser Trp Val Thr Ser Gly Asn
145                 150                 155                 160

Phe Asp Lys Ala Thr Leu Thr Ser Ile Met Gln Asn His Ile Thr Thr
                165                 170                 175

Leu Val Ser His Trp Lys Gly Gln Leu Ala Tyr Trp Asp Val Val Asn
            180                 185                 190

Glu Ala Phe Asn Asp Asp Gly Thr Phe Arg Gln Asn Val Phe Tyr Thr
        195                 200                 205

Thr Ile Gly Glu Asp Tyr Ile Gln Leu Ala Phe Glu Ala Ala Arg Ala
    210                 215                 220

Ala Asp Pro Thr Ala Lys Leu Cys Ile Asn Asp Tyr Asn Ile Glu Gly
225                 230                 235                 240

Thr Gly Ala Lys Ser Thr Ala Met Tyr Asn Leu Val Ser Lys Leu Lys
                245                 250                 255

Ser Ala Gly Val Pro Ile Asp Cys Ile Gly Val Gln Gly His Leu Ile
            260                 265                 270

Val Gly Glu Val Pro Thr Thr Ile Gln Ala Asn Leu Ala Gln Phe Ala
        275                 280                 285

Ser Leu Gly Val Asp Val Ala Ile Thr Glu Leu Asp Ile Arg Met Thr
    290                 295                 300

Leu Pro Ser Thr Thr Ala Leu Leu Gln Gln Gln Ala Lys Asp Tyr Val
305                 310                 315                 320

Ser Val Val Thr Ala Cys Met Asn Val Pro Arg Cys Ile Gly Ile Thr
                325                 330                 335

Ile Trp Asp Tyr Thr Asp Lys Tyr Ser Trp Val Pro Gln Thr Phe Ser
            340                 345                 350

Gly Gln Gly Asp Ala Cys Pro Trp Asp Ala Asn Leu Gln Lys Lys Pro
        355                 360                 365

Ala Tyr Ser Ala Ile Ala Ser Ala Leu Ala Ala
    370                 375

<210> SEQ ID NO 32
<211> LENGTH: 312
<212> TYPE: PRT
<213> ORGANISM: Trichoderma reesei

<400> SEQUENCE: 32

Leu Pro Thr Glu Thr Ile His Leu Asp Pro Glu Leu Ala Ala Leu Arg
1               5                   10                  15

Ala Asn Leu Thr Glu Arg Thr Ala Asp Leu Trp Asp Arg Gln Ala Ser
            20                  25                  30

Gln Ser Ile Asp Gln Leu Ile Lys Arg Gly Lys Leu Tyr Phe Gly
        35                  40                  45

Thr Ala Thr Asp Arg Gly Leu Leu Gln Arg Glu Lys Asn Ala Ala Ile
    50                  55                  60

Gln Ala Asp Leu Gly Gln Val Thr Pro Glu Asn Ser Met Lys Trp Gln
65                  70                  75                  80

Ser Leu Glu Asn Asn Gln Gly Gln Leu Asn Trp Gly Asp Ala Asp Tyr
                85                  90                  95

Leu Val Asn Phe Ala Gln Gln Asn Gly Lys Ser Ile Arg Gly His Thr
            100                 105                 110

Leu Ile Trp His Ser Gln Leu Pro Ala Trp Val Asn Asn Ile Asn Asn
        115                 120                 125

Ala Asp Thr Leu Arg Gln Val Ile Arg Thr His Val Ser Thr Val Val

```
                130                 135                 140
Gly Arg Tyr Lys Gly Lys Ile Arg Ala Trp Asp Val Val Asn Glu Ile
145                 150                 155                 160

Phe Asn Glu Asp Gly Thr Leu Arg Ser Ser Val Phe Ser Arg Leu Leu
                165                 170                 175

Gly Glu Glu Phe Val Ser Ile Ala Phe Arg Ala Ala Arg Asp Ala Asp
                180                 185                 190

Pro Ser Ala Arg Leu Tyr Ile Asn Asp Tyr Asn Leu Asp Arg Ala Asn
                195                 200                 205

Tyr Gly Lys Val Asn Gly Leu Lys Thr Tyr Val Ser Lys Trp Ile Ser
                210                 215                 220

Gln Gly Val Pro Ile Asp Gly Ile Gly Ser Gln Ser His Leu Ser Gly
225                 230                 235                 240

Gly Gly Gly Ser Gly Thr Leu Gly Ala Leu Gln Gln Leu Ala Thr Val
                245                 250                 255

Pro Val Thr Glu Leu Ala Ile Thr Glu Leu Asp Ile Gln Gly Ala Pro
                260                 265                 270

Thr Thr Asp Tyr Thr Gln Val Val Gln Ala Cys Leu Ser Val Ser Lys
                275                 280                 285

Cys Val Gly Ile Thr Val Trp Gly Ile Ser Asp Lys Asp Ser Trp Arg
                290                 295                 300

Ala Ser Thr Asn Pro Leu Leu Phe
305                 310

<210> SEQ ID NO 33
<211> LENGTH: 777
<212> TYPE: PRT
<213> ORGANISM: Trichoderma reesei

<400> SEQUENCE: 33

Gln Asn Asn Gln Thr Tyr Ala Asn Tyr Ser Ala Gln Gly Gln Pro Asp
1               5                   10                  15

Leu Tyr Pro Glu Thr Leu Ala Thr Leu Thr Leu Ser Phe Pro Asp Cys
                20                  25                  30

Glu His Gly Pro Leu Lys Asn Asn Leu Val Cys Asp Ser Ser Ala Gly
                35                  40                  45

Tyr Val Glu Arg Ala Gln Ala Leu Ile Ser Leu Phe Thr Leu Glu Glu
        50                  55                  60

Leu Ile Leu Asn Thr Gln Asn Ser Gly Pro Gly Val Pro Arg Leu Gly
65              70                  75                  80

Leu Pro Asn Tyr Gln Val Trp Asn Glu Ala Leu His Gly Leu Asp Arg
                85                  90                  95

Ala Asn Phe Ala Thr Lys Gly Gly Gln Phe Glu Trp Ala Thr Ser Phe
                100                 105                 110

Pro Met Pro Ile Leu Thr Thr Ala Ala Leu Asn Arg Thr Leu Ile His
                115                 120                 125

Gln Ile Ala Asp Ile Ile Ser Thr Gln Ala Arg Ala Phe Ser Asn Ser
                130                 135                 140

Gly Arg Tyr Gly Leu Asp Val Tyr Ala Pro Asn Val Asn Gly Phe Arg
145                 150                 155                 160

Ser Pro Leu Trp Gly Arg Gly Gln Glu Thr Pro Gly Glu Asp Ala Phe
                165                 170                 175

Phe Leu Ser Ser Ala Tyr Thr Tyr Glu Tyr Ile Thr Gly Ile Gln Gly
                180                 185                 190
```

```
Gly Val Asp Pro Glu His Leu Lys Val Ala Ala Thr Val Lys His Phe
    195                 200                 205
Ala Gly Tyr Asp Leu Glu Asn Trp Asn Gln Ser Arg Leu Gly Phe
210                 215                 220
Asp Ala Ile Ile Thr Gln Gln Asp Leu Ser Glu Tyr Tyr Thr Pro Gln
225                 230                 235                 240
Phe Leu Ala Ala Ala Arg Tyr Ala Lys Ser Arg Ser Leu Met Cys Ala
                245                 250                 255
Tyr Asn Ser Val Asn Gly Val Pro Ser Cys Ala Asn Ser Phe Phe Leu
            260                 265                 270
Gln Thr Leu Leu Arg Glu Ser Trp Gly Phe Pro Glu Trp Gly Tyr Val
        275                 280                 285
Ser Ser Asp Cys Asp Ala Val Tyr Asn Val Phe Asn Pro His Asp Tyr
    290                 295                 300
Ala Ser Asn Gln Ser Ser Ala Ala Ser Ser Leu Arg Ala Gly Thr
305                 310                 315                 320
Asp Ile Asp Cys Gly Gln Thr Tyr Pro Trp His Leu Asn Glu Ser Phe
                325                 330                 335
Val Ala Gly Glu Val Ser Arg Gly Ile Glu Arg Ser Val Thr Arg
            340                 345                 350
Leu Tyr Ala Asn Leu Val Arg Leu Gly Tyr Phe Asp Lys Lys Asn Gln
        355                 360                 365
Tyr Arg Ser Leu Gly Trp Lys Asp Val Val Lys Thr Asp Ala Trp Asn
    370                 375                 380
Ile Ser Tyr Glu Ala Ala Val Glu Gly Ile Val Leu Leu Lys Asn Asp
385                 390                 395                 400
Gly Thr Leu Pro Leu Ser Lys Lys Val Arg Ser Ile Ala Leu Ile Gly
                405                 410                 415
Pro Trp Ala Asn Ala Thr Thr Gln Met Gln Gly Asn Tyr Tyr Gly Pro
            420                 425                 430
Ala Pro Tyr Leu Ile Ser Pro Leu Glu Ala Ala Lys Lys Ala Gly Tyr
        435                 440                 445
His Val Asn Phe Glu Leu Gly Thr Glu Ile Ala Gly Asn Ser Thr Thr
    450                 455                 460
Gly Phe Ala Lys Ala Ile Ala Ala Lys Lys Ser Asp Ala Ile Ile
465                 470                 475                 480
Tyr Leu Gly Gly Ile Asp Asn Thr Ile Glu Gln Glu Gly Ala Asp Arg
                485                 490                 495
Thr Asp Ile Ala Trp Pro Gly Asn Gln Leu Asp Leu Ile Lys Gln Leu
            500                 505                 510
Ser Glu Val Gly Lys Pro Leu Val Val Leu Gln Met Gly Gly Gly Gln
        515                 520                 525
Val Asp Ser Ser Ser Leu Lys Ser Asn Lys Val Asn Ser Leu Val
    530                 535                 540
Trp Gly Gly Tyr Pro Gly Gln Ser Gly Gly Val Ala Leu Phe Asp Ile
545                 550                 555                 560
Leu Ser Gly Lys Arg Ala Pro Ala Gly Arg Leu Val Thr Thr Gln Tyr
                565                 570                 575
Pro Ala Glu Tyr Val His Gln Phe Pro Gln Asn Asp Met Asn Leu Arg
            580                 585                 590
Pro Asp Gly Lys Ser Asn Pro Gly Gln Thr Tyr Ile Trp Tyr Thr Gly
        595                 600                 605
Lys Pro Val Tyr Glu Phe Gly Ser Gly Leu Phe Tyr Thr Thr Phe Lys
```

```
              610                 615                 620
Glu Thr Leu Ala Ser His Pro Lys Ser Leu Lys Phe Asn Thr Ser Ser
625                 630                 635                 640

Ile Leu Ser Ala Pro His Pro Gly Tyr Thr Tyr Ser Glu Gln Ile Pro
                645                 650                 655

Val Phe Thr Phe Glu Ala Asn Ile Lys Asn Ser Gly Lys Thr Glu Ser
                660                 665                 670

Pro Tyr Thr Ala Met Leu Phe Val Arg Thr Ser Asn Ala Gly Pro Ala
                675                 680                 685

Pro Tyr Pro Asn Lys Trp Leu Val Gly Phe Asp Arg Leu Ala Asp Ile
                690                 695                 700

Lys Pro Gly His Ser Ser Lys Leu Ser Ile Pro Ile Pro Val Ser Ala
705                 710                 715                 720

Leu Ala Arg Val Asp Ser His Gly Asn Arg Ile Val Tyr Pro Gly Lys
                725                 730                 735

Tyr Glu Leu Ala Leu Asn Thr Asp Glu Ser Val Lys Leu Glu Phe Glu
                740                 745                 750

Leu Val Gly Glu Glu Val Thr Ile Glu Asn Trp Pro Leu Glu Glu Gln
                755                 760                 765

Gln Ile Lys Asp Ala Thr Pro Asp Ala
                770                 775

<210> SEQ ID NO 34
<211> LENGTH: 414
<212> TYPE: PRT
<213> ORGANISM: Talaromyces leycettanus

<400> SEQUENCE: 34

Gln Val Ala Asn Tyr Gly Gln Cys Gly Gly Gln Asn Tyr Ser Gly Pro
1               5                   10                  15

Thr Thr Cys Asn Pro Gly Trp Ser Cys Gln Tyr Leu Asn Pro Tyr Tyr
                20                  25                  30

Ser Gln Cys Leu Pro Ala Thr Gln Thr Thr Leu Thr Thr Ser Thr
            35                  40                  45

Lys Pro Thr Ser Thr Ser Thr Thr Arg Thr Ser Thr Ser Thr Thr
50                  55                  60

Ser Thr Gln Gly Gly Ser Ser Ser Thr Ser Ile Pro Ser Lys Asn Gly
65                  70                  75                  80

Leu Lys Phe Thr Ile Asp Gly Lys Thr Ala Tyr Tyr Ala Gly Thr Asn
                85                  90                  95

Thr Tyr Trp Leu Pro Phe Leu Thr Asn Asn Ala Asp Val Asp Leu Val
                100                 105                 110

Met Ser His Leu Gln Gln Ser Gly Leu Lys Ile Leu Arg Val Trp Gly
                115                 120                 125

Phe Asn Asp Val Asn Thr Gln Pro Gly Ser Gly Thr Val Trp Phe Gln
                130                 135                 140

Leu Leu Gln Asn Gly Gln Ala Thr Ile Asn Thr Gly Ala Asn Gly Leu
145                 150                 155                 160

Gln Arg Leu Asp Tyr Val Val Gln Ser Ala Glu Ala His Asp Ile Lys
                165                 170                 175

Leu Ile Ile Asn Phe Val Asn Asn Trp Asn Asp Tyr Gly Gly Ile Asn
                180                 185                 190

Ala Tyr Val Asn Asn Tyr Gly Gly Asn Ala Thr Thr Trp Tyr Thr Asn
                195                 200                 205
```

```
Ser Ala Ala Gln Ala Ala Tyr Arg Asn Tyr Ile Lys Ala Val Ile Ser
    210                 215                 220

Arg Tyr Ile Gly Ser Pro Ala Ile Phe Ala Trp Glu Leu Ala Asn Glu
225                 230                 235                 240

Pro Arg Cys His Gly Cys Asp Thr Ser Val Ile Tyr Asn Trp Val Ser
                245                 250                 255

Ser Thr Ser Ala Tyr Ile Lys Ser Leu Glu Pro Asn Arg Met Val Cys
            260                 265                 270

Ile Gly Asp Glu Gly Met Gly Leu Thr Thr Gly Ser Asp Gly Ser Tyr
        275                 280                 285

Pro Phe Gln Tyr Thr Glu Gly Thr Asp Phe Lys Asn Leu Ala Ile
290                 295                 300

Pro Thr Ile Asp Phe Gly Thr Leu His Leu Tyr Pro Ser Ser Trp Gly
305                 310                 315                 320

Glu Gln Asp Ser Trp Gly Ser Thr Trp Ile Ser Ala His Gly Gln Ala
                325                 330                 335

Cys Val Asn Ala Gly Lys Pro Cys Leu Leu Glu Glu Tyr Gly Ser Thr
                340                 345                 350

Asn His Cys Ser Ser Glu Ala Pro Trp Gln Ser Thr Ala Leu Ser Thr
            355                 360                 365

Asn Gly Ile Ala Ala Asp Ser Phe Trp Gln Tyr Gly Asp Thr Leu Ser
        370                 375                 380

Thr Gly Gln Ser Pro Asn Asp Gly Tyr Thr Ile Tyr Tyr Gly Ser Ser
385                 390                 395                 400

Asp Tyr Thr Cys Leu Val Thr Asn His Ile Ser Gln Phe Gln
                405                 410

<210> SEQ ID NO 35
<211> LENGTH: 411
<212> TYPE: PRT
<213> ORGANISM: Corollospora maritima

<400> SEQUENCE: 35

Gln Gln Thr Val Trp Gly Gln Cys Gly Gly Ile Asn Trp Thr Gly Pro
1               5                   10                  15

Thr Thr Cys Thr Ser Gly Asn His Cys Glu Lys Leu Asn Asp Trp Tyr
            20                  25                  30

Trp Gln Cys Leu Pro Gly Ala Ala Thr Thr Thr Gln Gln Pro Thr
            35                  40                  45

Thr Thr Arg Thr Thr Thr Thr Thr Arg Pro Thr Thr Thr Thr Thr
50                  55                  60

Thr Asn Asn Pro Pro Thr Gly Thr Gly Phe Pro Ser Arg Ser Gly Thr
65                  70                  75                  80

Lys Phe Thr Ile Asp Gly Val Thr Lys Tyr Phe Ala Gly Thr Asn Cys
                85                  90                  95

Tyr Trp Cys Pro Phe Leu Thr Ser Asn Ser Asp Val Asp Leu Val Phe
                100                 105                 110

Asp His Leu Arg Thr Ser Gly Ile Lys Ile Leu Arg Ile Trp Gly Phe
            115                 120                 125

Asn Asp Val Asn Ser Val Pro Ser Gly Gln Val Tyr Phe Gln His Leu
        130                 135                 140

Thr Ser Ser Gly Ser Thr Ile Asn Thr Gly Ser Asn Gly Leu Gln Arg
145                 150                 155                 160

Leu Asp Tyr Val Val Ser Ala Ala Gln Ser Arg Gly Ile Lys Leu Ile
                165                 170                 175
```

-continued

```
Ile Asn Phe Val Asn Asn Trp Asp Asp Tyr Gly Gly Met Lys Ala Tyr
            180             185             190

Thr Asn Ala Phe Gly Gly Asp His Asn Gly Trp Tyr Thr Asn Ser Ala
        195             200             205

Ala Gln Thr Gln Tyr Lys Lys Tyr Ile Asn Ala Val Val Ser Arg Tyr
    210             215             220

Arg Asn Ser Asn Ala Ile Leu Ala Trp Glu Leu Ala Asn Glu Pro Arg
225             230             235             240

Cys Gln Gln Cys Asp Thr Ser Val Ile Tyr Asn Trp Ala Lys Ser Thr
                245             250             255

Ser Glu Tyr Val Lys Ser Leu Asp Ser Asn His Met Val Thr Leu Gly
            260             265             270

Asp Glu Gly Phe Gly Leu Ser Gly Asp Gly Ser Tyr Pro Tyr Thr Tyr
        275             280             285

Tyr Glu Gly Val Asp Phe Gln Lys Asn Leu Glu Ile Ser Thr Leu Asp
    290             295             300

Phe Gly Thr Phe His Met Tyr Pro Asp His Trp Gly Val Ser Ser Ser
305             310             315             320

Trp Gly Asn Asp Trp Ile Arg Ser His Ala Ala Leu Cys Ala Ala Ala
                325             330             335

Asn Lys Pro Cys Leu Leu Glu Glu Tyr Gly Ile Glu Ser Asn Lys Cys
            340             345             350

Ser Ile Glu Gly Gln Trp Gln Ala Thr Ser Arg Gly Ala Ala Gly Met
        355             360             365

Gly Gly Asp Ala Phe Trp Gln Leu Gly Asp Thr Leu Ser Thr Gly Gln
    370             375             380

Thr His Asn Asp Gly Phe Thr Ile Tyr Tyr Gly Ser Ser Asp Trp Gln
385             390             395             400

Cys Leu Val Thr Asn His Val Ala Ala Ile Gly
                405             410
```

PROCESS FOR DEGRADING MANNAN-CONTAINING CELLULOSIC MATERIALS

CROSS-REFERENCE TO RELATED APPLICATIONS

This application is a divisional of U.S. application Ser. No. 15/109,696 filed on Jul. 5, 2016, now U.S. Pat. No. 10,287,563, which is a 35 U.S.C. 371 national application of international application no. 5 PCT/US2015/010423 filed Jan. 7, 2015, which claims priority or the benefit under 35 U.S.C. 119 of U.S. provisional application No. 61/924,491 filed Jan. 7, 2014 the contents of which are fully incorporated herein by reference.

REFERENCE TO A SEQUENCE LISTING

This application contains a Sequence Listing in computer readable form, which is incorporated herein by reference.

TECHNICAL FIELD

The present invention relates to processes comprising enzymatic degradation of a mannan-containing cellulosic material for producing a hydrolyzate. The invention also relates to processes of producing a fermentation product from the mannan-containing cellulosic material.

BACKGROUND OF THE INVENTION

Mannan is a non-starch polysaccharide which is a polymer of the monosaccharide mannose. Mannan is found in plant, fungal and bacterial cell walls. Mannan is present in significant amounts in certain plant residues, such as, e.g., softwood.

Softwood is a promising feedstock for bioethanol production. Softwood contains up to 30% mannan in the form of galactoglucomannan. Galactoglucomannans consist of a beta-1,4 linked backbone of beta-D-glucopyranose and beta-D-mannopyranose units, substituted at the C-6 by alpha-D-galactopyranose units. Hemicellulose in softwood may prevent the hydrolysis of cellulose in the absence of accessory enzymes such as hemicellulases. For the complete hydrolysis of mannan-type hemicellulose, a wide array of enzymes is required. The main enzyme involved in hydrolysis of galactoglucomannan is endo-1,4-beta-mannanase (EC.3.2.1.78). Endomannanase cleaves the main chain to oligosaccharides facilitating the solubilisation of galactoglucomannans. The action of endomannanases is restricted by galactose substitutions, hence their cleavage by alpha-galactosidase is needed for the complete hydrolysis of the polymer. Oligosaccharides from galactoglucomannan are hydrolyzed to monomers by beta-mannosidase and beta-glucosidase.

Clarke et al. (*Appl. Microbiol. Biotechnol.* 53:661-667 (2000)) compare bleaching of softwood paper pulp using combinations of xylanase, mannanase, and alpha-galactosidase.

Varnai et al. (*Bioresource Technology* 102: 9096-9104 (2011)) disclose that xylanase and mannanase improve the hydrolysis of softwood.

WO 2009/074685 discloses a process of hydrolyzing substrates comprising contacting a slurry of the mannan-containing cellulosic material with an enzyme composition comprising cellulase, mannanase, and mannosidase.

It is an object of the present invention to provide improved processes for hydrolyzing mannan-containing cellulosic materials, e.g., galactoglucomannan and mannan rich softwood substrates.

SUMMARY OF THE INVENTION

The present invention relates to an enzyme composition comprising one or more endoglucanases, one or more cellobiohydrolases, one or more beta-glucosidases, at least one beta-mannosidase, and at least one mannanase, wherein the mannanase is selected from the group consisting of *Aspergillus niger* mannanase, *Trichoderma reesei* mannanase, *Corollospora maritima* mannanase or *Talaromyces leycettanus* mannanase.

The present invention further relates to the use of such a composition in a process for hydrolysis of a mannan-containing cellulosic material comprising contacting said material with said composition. In a further asect the present invention relates to a process for producing a fermentation product, comprising:

(a) saccharifying a mannan-containing cellulosic material with an enzyme composition of the present invention;

(b) fermenting the saccharified cellulosic material with a fermenting microorganism to produce the fermentation product; and (c) recovering the fermentation product from the fermentation.

In a still further aspect the present invention relates to a use of a mannase and a beta-manosidase in combination with a cellulase composition for hydrolysing a mannan-containing cellulosic material, wherein the mannanase is selected from the group consisting of *Aspergillus niger* mannanase, *Trichoderma reesei* mannanase, *Corollospora maritima* mannanase or *Talaromyces leycettanus* mannanase.

The present invention also relates to a process for producing a fermentation product, the process comprising; a) contacting an aqueous slurry of a mannan-containing cellulosic material with an enzyme composition of the present invention to produce a soluble hydrolyzate, and b) contacting the soluble hydrolyzate with a fermenting organism to produce a fermentation product.

DETAILED DESCRIPTION OF THE INVENTION

Definitions

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. Acetylxylan esterase activity can be determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-galactosidase: The term "alpha-galactosidase" means an alpha-D-galactoside galactohydrolase (EC 3.2.1.22) that catalyzes the hydrolysis of terminal, non-reducing alpha-D-galactose residues in alpha-D-galactosides, including galactose oligosaccharides, galactomannans and galactolipids. Alpha-galactosidase is also known as melibiase; alpha-D-galactosidase; alpha-galactosidase A; and alpha-galactoside galactohydrolase. Alpha-galactosidase activity can be determined by measuring the degradation of the colorless p-nitrophenyl-α-D-galactopyranoside (p-NPGal) to form 4-nitrophenol, which gives a yellow color at alkaline pH that can be detected at 405 nm. One alpha-galactose unit is the amount of enzyme which degrades 1 mmol p-NPGal per minute under the standard conditions (37° C., pH 5.5, 15 minutes).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. Alpha-glucuronidase activity can be determined according to de Vries, 1998, *J. Bacteriol.* 180: 243-249. One unit of alpha-glucuronidase equals the amount of enzyme capable of releasing 1 μmole of glucuronic or 4-O-methylglucuronic acid per minute at pH 5, 40° C.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. Alpha-L-arabinofuranosidase activity can be determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Auxiliary Activity 9: The term "Auxiliary Activity 9" or "AA9" means a polypeptide classified as a lytic polysaccharide monooxygenase (Quinlan et al., 2011, *Proc. Natl. Acad. Sci. USA* 208: 15079-15084; Phillips et al., 2011, *ACS Chem. Biol.* 6: 1399-1406; Lin et al., 2012, *Structure* 20: 1051-1061). AA9 polypeptides were formerly classified into the glycoside hydrolase Family 61 (GH61) according to Henrissat, 1991, *Biochem. J.* 280: 309-316, and Henrissat and Bairoch, 1996, *Biochem. J.* 316: 695-696.

AA9 polypeptides enhance the hydrolysis of a cellulosic material by an enzyme having cellulolytic activity. Cellulolytic enhancing activity can be determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of an AA9 polypeptide for 1-7 days at a suitable temperature, such as 40° C.-80° C., e.g., 50° C., 55° C., 60° C., 65° C., or 70° C., and a suitable pH, such as 4-9, e.g., 4.5, 5.0, 5.5, 6.0, 6.5, 7.0, 7.5, 8.0, or 8.5, compared to a control hydrolysis with equal total protein loading without cellulolytic enhancing activity (1-50 mg of cellulolytic protein/g of cellulose in PCS).

AA9 polypeptide enhancing activity can be determined using a mixture of CELLUCLAST® 1.5 L (Novozymes A/S, Bagsværd, Denmark) and beta-glucosidase as the source of the cellulolytic activity, wherein the beta-glucosidase is present at a weight of at least 2-5% protein of the cellulase protein loading. In one aspect, the beta-glucosidase is an *Aspergillus oryzae* beta-glucosidase (e.g., recombinantly produced in *Aspergillus oryzae* according to WO 02/095014). In another aspect, the beta-glucosidase is an *Aspergillus fumigatus* beta-glucosidase (e.g., recombinantly produced in *Aspergillus oryzae* as described in WO 02/095014).

AA9 polypeptide enhancing activity can also be determined by incubating an AA9 polypeptide with 0.5% phosphoric acid swollen cellulose (PASC), 100 mM sodium acetate pH 5, 1 mM $MnSO_4$, 0.1% gallic acid, 0.025 mg/ml of *Aspergillus fumigatus* beta-glucosidase, and 0.01% TRITON® X-100 (4-(1,1,3,3-tetramethylbutyl)phenyl-polyethylene glycol) for 24-96 hours at 40° C. followed by determination of the glucose released from the PASC.

AA9 polypeptide enhancing activity can also be determined according to WO 2013/028928 for high temperature compositions.

AA9 polypeptides enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. Beta-glucosidase activity can be determined using p-nitrophenyl-beta-D-glucopyranoside as substrate according to the procedure of Venturi et al., 2002, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-mannosidase: The term "beta-mannosidase" means a beta-D-mannoside mannohydrolase (EC 3.2.1.25) that catalyzes the hydrolysis of terminal, non-reducing beta-D-mannose residues in beta-D-mannosides. Beta-mannosidase is also known as beta-D-mannosidase; beta-mannoside mannohydrolase; exo-beta-D-mannanase. Mannosidase activity can be determined by measuring the release of p-nitrophenol (pNP) from pNP-β-mannopyranosid at 37° C. for 15 minutes. One unit of mannosidase equals the amount of enzyme capable of releasing 1 μmole of pNP per minute from pNP-beta-mannopyranosid.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. Beta-xylosidase activity can be determined using 1 mM p-nitrophenyl-beta-D-xyloside as substrate in 100 mM sodium citrate containing 0.01% TWEEN® 20 at pH 5, 40° C. One unit of beta-xylosidase is defined as 1.0 μmole of p-nitrophenolate anion produced per minute at 40° C., pH 5 from 1 mM p-nitrophenyl-beta-D-xyloside in 100 mM sodium citrate containing 0.01% TWEEN® 20.

Carbohydrate binding module: The term "carbohydrate binding module" means a domain within a carbohydrate-active enzyme that provides carbohydrate-binding activity (Boraston et al., 2004, *Biochem. J.* 383: 769-781). A majority of known carbohydrate binding modules (CBMs) are contiguous amino acid sequences with a discrete fold. The carbohydrate binding module (CBM) is typically found either at the N-terminal or at the C-terminal extremity of an enzyme. Some CBMs are known to have specificity for cellulose.

Catalytic domain: The term "catalytic domain" means the region of an enzyme containing the catalytic machinery of the enzyme.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teeri et al., 1998, *Biochem. Soc. Trans.* 26: 173-178). Cellobiohydrolase activity can be determined according to the procedures described by Lever et al., 1972, *Anal. Biochem.* 47: 273-279; van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, *Pure Appl. Chem.* 59: 257-68).

Cellulolytic enzyme activity can be determined by measuring the increase in production/release of sugars during hydrolysis of a cellulosic material by cellulolytic enzyme(s) under the following conditions: 1-50 mg of cellulolytic enzyme protein/g of cellulose in pretreated corn stover (PCS) (or other pretreated cellulosic material) for 3-7 days at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by an AMINEX® HPX-87H column (Bio-Rad Laboratories, Inc., Hercules, Calif., USA).

Endoglucanase: The term "endoglucanase" means a 4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-1,4 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, supra). Endoglucanase activity can also be determined using carboxymethyl cellulose (CMC) as substrate according to the procedure of Ghose, 1987, supra, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase (FAE) is also known as ferulic acid esterase, hydroxycinnamoyl esterase, FAE-III, cinnamoyl ester hydrolase, FAEA, cinnAE, FAE-I, or FAE-II. Feruloyl esterase activity can be determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of a mature polypeptide or domain; wherein the fragment has biological activity.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, *Current Opinion In Microbiology* 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature such as 40-80° C., e.g., 50° C., 55° C., 60° C., 65° C., or 70° C., and a suitable pH such as 4-9, e.g., 5.0, 5.5, 6.0, 6.5, or 7.0.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Mannanase: The term "mannanase" means a mannan endo-1,4-beta-mannosidase (EC 3.2.1.78) that catalyzes the hydrolysis of beta-1,4-D-mannosidic linkages in mannans, galactomannans and glucomannans. Mannanase is also known as endo-1,4-beta-mannanase; endo-beta-1,4-mannase; beta-mannanase B; beta-1, 4-mannan 4-mannanohydrolase; endo-beta-mannanase; beta-D-mannanase; 1,4-beta-D-mannan mannanohydrolase. Mannanase activity can be determined by measuring the release of reducing carbohydrate from hydrolysis of carob galactomannan. The reaction is stopped by an alkaline reagent including PAHBAH amd Bi3+, which complexes with reducing sugar producing color detected at 405 nm. One unit of mannanase equals the amount of enzyme capable of releasing 1 μmole of reducing sugar.

Mannan-containing cellulosic materials: The term "mannan-containing cellulosic material" means a cellulosic material comprising mannan. Any mannan-containing cellulosic material is contemplated according to the present invention. In an embodiment the mannan-containing cellulosic material contains 1-25 wt. %, 2-20 wt. %, 3-15 wt. %, or 4-10 wt. % mannan. The mannan-containing cellulosic material may also comprise other constituents such as cellulosic material, including cellulose and/or hemicellulose, and may also comprise other constituents such as proteinaceous material, starch, sugars, such as fermentable sugars and/or un-fermentable sugars.

Mannan, galacto-mannan, and galactoglucomannnan are found in plant, fungal and bacterial cell walls. Mannan-containing cellulosic material is generally found, for example, in the stems, leaves, fruits, hulls, husks, and cobs of plants or leaves, branches, and wood of trees. It is understood herein that mannan-containing cellulosic material may be in the form of plant cell wall material containing lignin, cellulose, and hemicellulose in a mixed matrix.

The mannan-containing cellulosic material may be selected from the list consisting of herbaceous and/or woody crops, agricultural food and feed crops, animal feed products, tubers, roots, stems, legumes, cassava peels, cocoa pods, rice husks and/or hulls, rice bran, cobs, straw, hulls, husks, sugar beet pulp, locust bean pulp, vegetable pomaces, agricultural crop waste, straw, stalks, leaves, corn bran, husks, cobs, rind, shells, pods, wood waste, bark, shavings, sawdust, wood pulp, pulping liquor, waste paper, cardboard, wood waste, industrial or municipal waste water solids, manure, by-product from brewing and/or fermentation processes, wet distillers grain, dried distillers grain, spent grain, vinasse and bagasse.

In an embodiment, the mannan-containing cellulosic material is derived from softwood. Softwood is wood from gymnosperm trees such as conifers. Examples of softwood species include, but are not limited to, pines, spruces, hemlocks, firs, conifers etc., e.g., red pine (*Pinus resinosa*), lodgepole pine (*Pinus contorta*), loblolly pine (*Pinus taeda*), Eastern spruce (*Picea* spp.), Norway spruce (*Picea abies*) Douglas Fir (*Pseudotsuga menziesii*), Eastern Red-Cedar (*Juniperos virginiana*) and redwood (*Sequoia sempervirens*).

Softwood contains up to 30% mannans, in the form of galactoglucomannan. In softwood, the content of glucomannan increases steadily from the outer parts to the inner parts. Softwood typically contains 40-60% cellulose, 20-30% hemicellulose and 20-30% lignin. The composition after pretreatment is very dependent on the type of pretreatment and parameters.

In an embodiment the mannan-containing cellulosic material comprises plant material derived from an *Aracaceae* sp. such as *Cocos mucifera, Elaeis guineensis, Elaeis malanococca*, an *Coffea* sp., an *Cyamopsis* sp. such as *Cyamopsis tetragonoloba* (guar bean).

In one embodiment the mannan-containing cellulosic material comprises coffee waste, guar meal, palm kernel cake, palm kernel meal and/or copra cake.

In another embodiment the mannan-containing cellulosic material is municipal solid waste (MSW). Municipal Solid Waste (MSW) is commonly also known as trash, garbage, refuse or rubbish. It consists of solid waste fractions that typically comes from municipalities and includes for instance waste from homes, schools, offices, hospitals, institutions etc.

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment.

Variant: The term "variant" means a polypeptide comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, *Journal of the Science of Food and Agriculture* 86(11): 1636-1647; Spanikova and Biely, 2006, *FEBS Letters* 580(19): 4597-4601; Herrimann et al., 1997, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. A common total xylanolytic activity assay is based on production of reducing sugars from polymeric 4-O-methyl glucuronoxylan as described in Bailey et al., 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Xylan degrading activity can be determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, *Anal. Biochem.* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. Xylanase activity can be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

The present invention relates to compostions and methods/processes for degrading mannan-containing cellulosic material using a cellulase composition in combination with a beta-manosidase and a mannanase. The cellulase composition may be any suitable mixture of cellulases necessary to efficiently degrade cellulose. As a minimum the cellulase composition should contain at least three enzyme activities selected from beta-glucosidase, endoglucanase, and cellobiohydrolase. Preferably the cellobiohydrolase includes both a cellobiohydrolase I and a cellobiohydrolase II. The cellulase composition may e.g. be a *Trichoderma* whole cellulase. A whole cellulase preparation includes all of the cellulase components naturally produced by a strain of *Trichoderma*, e.g., *Trichoderma reesei*. The cellulase composition may in another embodiment be a mixture of cellulases from different microorganisms. For more details on these specific cellulase components see enzyme sections below.

Enzyme Compositions

Thus the present invention relates to a composition comprising one or more endoglucanases, one or more cellobiohydrolases, at least one beta-glucosidases, at least one beta-mannosidase, and at least one mannanase, wherein the mannanase is selected from the group consisting of *Aspergillus niger* mannanase, *Trichoderma reesei* mannanase, *C. maritima* mannanase or *Talaromyces leycettanus* mannanase.

AA9 Polypeptide

Any AA9 polypeptide can be used as a component of the enzyme composition. Examples of AA9 polypeptides useful in the processes of the present invention include, but are not limited to, AA9 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290 and WO 2012/1449344), *Myceliophthora thermophila* (WO 2009/033071, WO 2009/085935, WO 2009/085859, WO 2009/085864, and WO 2009/085868), *Aspergillus fumigatus* (WO 2010/138754), *Penicillium pinophilum* (WO 2011/005867), *Thermoascus* sp. (WO 2011/039319), *Penicillium emersonii* (WO 2011/041397), *Thermoascus crustaceous* (WO 2011/041504), *Aspergillus aculeatus* (WO 2012/125925), *Thermomyces lanuginosus* (WO 2012/113340, WO 2012/129699, and WO 2012/130964), *Aurantiporus alborubescens* (WO 2012/122477), *Trichophaea saccata* (WO 2012/122477), *Penicillium thomii* (WO 2012/122477), *Talaromyces stipitatus* (WO 2012/135659), *Humicola insolens* (WO 2012/146171), *Malbranchea cinnamomea* (WO 2012/101206), *Talaromyces leycettanus* (WO 2012/101206), *Chaetomium thermophilum* (WO 2012/101206), and *Talaromyces emersonii* (WO 2012/000892).

In one aspect, the AA9 polypeptide is used in the presence of a soluble activating divalent metal cation according to WO 2008/151043, e.g., manganese or copper. In another aspect, the AA9 polypeptide is used in the presence of a dioxy compound, a bicyclic compound, a heterocyclic compound, a nitrogen-containing compound, a quinone compound, a sulfur-containing compound, or a liquor obtained from a pretreated cellulosic material such as pretreated corn stover (WO 2012/021394, WO 2012/021395, WO 2012/021396, WO 2012/021399, WO 2012/021400, WO 2012/021401, WO 2012/021408, and WO 2012/021410).

In an embodiment, the AA9 polypeptide has a sequence identity of at least 70%, e.g., at least 75%, at least 80%, at least 85%, at least 90%, or at least 95%, to SEQ ID NO: 1.

In another embodiment, the AA9 polypeptide has a sequence identity of at least 70%, e.g., at least 75%, at least 80%, at least 85%, at least 90%, or at least 95%, to SEQ ID NO: 2.

In another embodiment, the AA9 polypeptide has a sequence identity of at least 70%, e.g., at least 75%, at least 80%, at least 85%, at least 90%, or at least 95%, to SEQ ID NO: 3.

In another embodiment, the AA9 polypeptide has a sequence identity of at least 70%, e.g., at least 75%, at least 80%, at least 85%, at least 90%, or at least 95%, to SEQ ID NO: 4.

In another embodiment, the AA9 polypeptide has a sequence identity of at least 70%, e.g., at least 75%, at least 80%, at least 85%, at least 90%, or at least 95%, to SEQ ID NO: 5.

In another embodiment, the AA9 polypeptide has a sequence identity of at least 70%, e.g., at least 75%, at least 80%, at least 85%, at least 90%, or at least 95%, to SEQ ID NO: 6.

In another embodiment, the AA9 polypeptide has a sequence identity of at least 70%, e.g., at least 75%, at least 80%, at least 85%, at least 90%, or at least 95%, to SEQ ID NO: 7.

In another embodiment, the AA9 polypeptide has a sequence identity of at least 70%, e.g., at least 75%, at least 80%, at least 85%, at least 90%, or at least 95%, to SEQ ID NO: 8.

Beta-Glucosidase

Any beta-glucosidase can be used as a component of the enzyme composition. Examples of beta-glucosidases useful in the present invention include, but are not limited to, beta-glucosidases from *Aspergillus aculeatus* (Kawaguchi et al., 1996, Gene 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 02/095014), *Penicillium brasilianum* IBT 20888 (WO 2007/019442 and WO 2010/088387), *Thielavia terrestris* (WO 2011/035029), and *Trichophaea saccata* (WO 2007/019442).

In an embodiment, the beta-glucosidase has a sequence identity of at least 70%, e.g., at least 75%, at least 80%, at least 85%, at least 90%, or at least 95%, to SEQ ID NO: 10.

In another embodiment, the beta-glucosidase has a sequence identity of at least 70%, e.g., at least 75%, at least 80%, at least 85%, at least 90%, or at least 95%, to SEQ ID NO: 11.

Beta-Mannosidase

Any beta-mannosidase can be used as a component of the enzyme composition. Examples of beta-mannosidases useful in the present invention include, but are not limited to, a beta-mannosidase from *Aspergillus aculeatus* (SwissProt: O74168), *Aspergillus niger* (SwissProt:A2QWU9), *Bacteroides thetaiotaomicron* (SwissProt:Q8AAK6), *Caenorhabditis elegans* (SwissProt:Q93324), *Cellulomonas fimi* (SwissProt:Q9XCV4), *Streptomyces* sp. S27 (SwissProt:D2DFB5), *Thermotoga maritima* MSB8 (SwissProt:Q9X1V9), and *Thermotoga neapolitana* (SwissProt:Q93M25).

In an embodiment, the beta-mannosidase has a sequence identity of at least 70%, e.g., at least 75%, at least 80%, at least 85%, at least 90%, or at least 95%, to SEQ ID NO: 12.

Beta-Xylosidase

Any beta-xylosidase can be used as a component of the enzyme composition. Examples of beta-xylosidases useful in the processes of the present invention include, but are not limited to, beta-xylosidases from *Aspergillus fumigatus* (WO 2011/057140), *Neurospora crassa* (SwissProt:Q7SOW4), *Talaromyces emersonii* (SwissProt:Q8X212), *Talaromyces thermophilus* (GeneSeqP:BAA22816), and *Trichoderma reesei* (UniProtKB/TrEMBL:Q92458).

In an embodiment, the beta-xylosidase has a sequence identity of at least 70%, e.g., at least 75%, at least 80%, at least 85%, at least 90%, or at least 95%, to SEQ ID NO: 13.

In another embodiment, the beta-xylosidase has a sequence identity of at least 70%, e.g., at least 75%, at least 80%, at least 85%, at least 90%, or at least 95%, to SEQ ID NO: 14.

In another embodiment, the beta-xylosidase has a sequence identity of at least 70%, e.g., at least 75%, at least 80%, at least 85%, at least 90%, or at least 95%, to SEQ ID NO: 33.

Cellobiohydrolase

Any cellobiohydroase I (CBH I) and cellobiohydrolase II (CBH II) can be used as a component of the enzyme composition. Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871, US 2007/0238155), *Penicillium occitanis* cellobiohydrolase I (GenBank:AY690482), *Talaromyces emersonii* cellobiohydrolase I (GenBank:AF439936), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086). *Aspergillus fumigatus* cellobiohydrolase I (WO 2013/028928), *Aspergillus fumigatus* cellobiohydrolase II (WO 2013/028928)

In an embodiment, the cellobiohydrolase I has a sequence identity of at least 70%, e.g., at least 75%, at least 80%, at least 85%, at least 90%, or at least 95%, to SEQ ID NO: 16.

In another embodiment, the cellobiohydrolase I has a sequence identity of at least 70%, e.g., at least 75%, at least 80%, at least 85%, at least 90%, or at least 95%, to SEQ ID NO: 18.

In an embodiment, the cellobiohydrolase II has a sequence identity of at least 70%, e.g., at least 75%, at least 80%, at least 85%, at least 90%, or at least 95%, to SEQ ID NO: 15, In another embodiment, the cellobiohydrolase II has a sequence identity of at least 70%, e.g., at least 75%, at least 80%, at least 85%, at least 90%, or at least 95%, to SEQ ID NO: 17.

In another embodiment, the cellobiohydrolase II has a sequence identity of at least 70%, e.g., at least 75%, at least 80%, at least 85%, at least 90%, or at least 95%, to SEQ ID NO: 19.

Endoglucanase

Any endoglucanase can be used as a component of the enzyme composition. In an embodiment, the endoglucanase is an endoglucanase I, endoglucanase II, endoglucanase III, or endoglucanase V. Examples of fungal endoglucanases that can be used in the present invention, include, but are not limited to, *Trichoderma reesei* endoglucanase I (Penttila et al., 1986, Gene 45: 253-263), *Trichoderma reesei* Cel7B endoglucanase I (GenBank:M15665), *Trichoderma reesei* endoglucanase II (Saloheimo et al., 1988, Gene 63:11-22), *Trichoderma reesei* Cel5A endoglucanase II (GenBank: M19373), *Trichoderma reesei* endoglucanase III (Okada et al., 1988, *Appl. Environ. Microbiol.* 64: 555-563, GenBank: AB003694), *Trichoderma reesei* endoglucanase V (Saloheimo et al., 1994, *Molecular Microbiology* 13: 219-228, GenBank:Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Fusarium oxysporum* endoglucanase (GenBank:L29381), *Humicola grisea* var. thermoidea endoglucanase (GenBank:AB003107), *Melanocarpus albomyces* endoglucanase (GenBank: MAL515703), *Neurospora crassa* endoglucanase (Gen Bank: XM_324477), *Humicola insolens* endoglucanase V, *Myceliophthora thermophila* CBS 117.65 endoglucanase (WO 2007/109441, WO 2008/008070), *Thermoascus aurantiacus* endoglucanase I (GenBank:AF487830) and *Trichoderma reesei* strain No. VTT-D-80133 endoglucanase (GenBank: M15665). *Penicillium pinophalum* (WO 2012/062220)

In another embodiment, the endoglucanase has a sequence identity of at least 70%, e.g., at least 75%, at least 80%, at least 85%, at least 90%, or at least 95%, to SEQ ID NO: 20.

In another embodiment, the endoglucanase has a sequence identity of at least 70%, e.g., at least 75%, at least 80%, at least 85%, at least 90%, or at least 95%, to SEQ ID NO: 21.

In another embodiment, the endoglucanase has a sequence identity of at least 70%, e.g., at least 75%, at least 80%, at least 85%, at least 90%, or at least 95%, to SEQ ID NO: 22.

In another embodiment, the endoglucanase has a sequence identity of at least 70%, e.g., at least 75%, at least 80%, at least 85%, at least 90%, or at least 95%, to SEQ ID NO: 23.

In another embodiment, the endoglucanase has a sequence identity of at least 70%, e.g., at least 75%, at least 80%, at least 85%, at least 90%, or at least 95%, to SEQ ID NO: 24.

In another embodiment, the endoglucanase has a sequence identity of at least 70%, e.g., at least 75%, at least 80%, at least 85%, at least 90%, or at least 95%, to SEQ ID NO: 25.

Mannanase

Any mannanase can be used as a component of the enzyme composition. Mannanases have been identified in several *Bacillus* organisms. For example, Talbot et al., 1990, *Appl. Environ. Microbiol.* 56(11): 3505-3510 describes a beta-mannanase derived from *Bacillus stearothermophilus* having an optimum pH of 5.5-7.5. Mendoza et al., 1994, *World Journal of Microbiology and Biotechnology* 10(5): 551-555 describes a beta-mannanase derived from *Bacillus subtilis* having an optimum activity at pH 5.0 and 55° C. JP-03047076 discloses a beta-mannanase derived from *Bacillus* sp., having a pH optimum of 8-10. JP-63056289 describes the production of an alkaline, thermostable beta-mannanase. JP-08051975 discloses alkaline beta-mannanases from alkalophilic *Bacillus* sp. AM-001. A purified mannanase from *Bacillus amyloliquefaciens* is disclosed in WO 97/11164. WO 94/25576 discloses an enzyme from *Aspergillus aculeatus*, CBS 101.43, exhibiting mannanase activity and WO 93/24622 discloses a mannanase isolated from *Trichoderma reesei*.

The mannanase may be derived from a strain of *Bacillus*, such as the amino acid sequence deposited as GeneSeqP: AAY54122.

A suitable commercial mannanase preparation is Mannaway® produced by Novozymes A/S.

Other examples of mannanases include, but are not limited, mannanases from *Aspergillus niger* (GeneSeqP: BA K16998) and *Trichoderma reesei* (GeneSeqP:AXQ82767).

In an embodiment, the mannanase is an *Aspergillus niger* mannanase, particularly the mannanase shown in SEQ ID NO: 26 or a beta-mannosidase having a sequence identity of at least 70%, e.g., at least 75%, at least 80%, at least 85%, at least 90%, or at least 95%, or at least 98% or at least 99% to SEQ ID NO: 26. In an embodiment, the mannanase is a *Trichoderma reesei* mannanase, particularly the mannanase shown in SEQ ID NO: 27 or a beta-mannosidase having a sequence identity of at least 70%, e.g., at least 75%, at least 80%, at least 85%, at least 90%, or at least 95%, or at least 98% or at least 99% to SEQ ID NO: 27. In an embodiment, the mannanase is a *Talaromyces leycettanus* mannanase, particularly the mannanase shown in SEQ ID NO: 34 or a beta-mannosidase having a sequence identity of at least 70%, e.g., at least 75%, at least 80%, at least 85%, at least 90%, or at least 95%, or at least 98% or at least 99% to SEQ ID NO: 34. In an embodiment, the mannanase is a *Corollospora maritima* mannanase, particularly the mannanase shown in SEQ ID NO: 35 or a beta-mannosidase having a sequence identity of at least 70%, e.g., at least 75%, at least 80%, at least 85%, at least 90%, or at least 95%, or at least 98% or at least 99% to SEQ ID NO: 35.

Xylanase

Any xylanase can be used as a component of the enzyme composition. Examples of xylanases useful in the processes of the present invention include, but are not limited to, xylanases from *Aspergillus aculeatus* (GeneSeqP: AAR63790; WO 94/21785), *Aspergillus fumigatus* (WO 2006/078256), *Penicillium pinophilum* (WO 2011/041405), *Penicillium* sp. (WO 2010/126772), *Thermomyces lanuginosus* (GeneSeqP:BAA22485), *Talaromyces thermophilus* (GeneSeqP:BAA22834), *Thielavia terrestris* NRRL 8126 (WO 2009/079210), and *Trichophaea saccata* (WO 2011/057083).

In an embodiment, the xylanase has a sequence identity of at least 70%, e.g., at least 75%, at least 80%, at least 85%, at least 90%, or at least 95%, to SEQ ID NO: 28.

In an embodiment, the xylanase has a sequence identity of at least 70%, e.g., at least 75%, at least 80%, at least 85%, at least 90%, or at least 95%, to SEQ ID NO: 29.

In an embodiment, the xylanase has a sequence identity of at least 70%, e.g., at least 75%, at least 80%, at least 85%, at least 90%, or at least 95%, to SEQ ID NO: 30.

In an embodiment, the xylanase has a sequence identity of at least 70%, e.g., at least 75%, at least 80%, at least 85%, at least 90%, or at least 95%, to SEQ ID NO: 31.

In an embodiment, the xylanase has a sequence identity of at least 70%, e.g., at least 75%, at least 80%, at least 85%, at least 90%, or at least 95%, to SEQ ID NO: 32.

Embodiments of Enzymes Compositions

In one aspect the composition comprises one or more endoglucanases, one or more cellobiohydrolases, one or more beta-glucosidases, at least one beta-mannosidase, and one mannanase, wherein the mannanase is selected from the group consisting of *Aspergillus niger* mannanase, *Trichoderma reesei* mannanase, *C. maritima* mannanase or *Talaromyces leycettanus* mannanase.

In an embodiment the composition comprises one or more endoglucanases, one or more cellobiohydrolases, one or more beta-glucosidases, at least one beta-mannosidase, and one mannanase, wherein the beta-mannosidase is selected from *A. niger* beta-mannosidase shown as SEQ ID NO: 12 or a beta-mannosidase having a sequence identity of at least 70%, e.g., at least 75%, at least 80%, at least 85%, at least 90%, at least 95%, at least 98%, or at least 99% to SEQ ID NO: 12, and wherein the mannanase is selected from *A. niger* mannanase shown as SEQ ID NO: 26 or a mannase having a sequence identity of at least 70%, e.g., at least 75%, at least 80%, at least 85%, at least 90%, at least 95%, or at least 98%, or at least 99% to SEQ ID NO: 26.

In an embodiment the composition comprises one or more endoglucanases, one or more cellobiohydrolases, one or more beta-glucosidases, at least one beta-mannosidase, and one mannanase, wherein the beta-mannosidase is selected from *A. niger* beta-mannosidase shown as SEQ ID NO: 12 or a beta-mannosidase having a sequence identity of at least 70%, e.g., at least 75%, at least 80%, at least 85%, at least 90%, at least 95%, at least 98%, or at least 99% to SEQ ID NO: 12, and wherein the mannanase is selected from *T. reesei* mannanase shown as SEQ ID NO: 27 or a mannase having a sequence identity of at least 70%, e.g., at least 75%, at least 80%, at least 85%, at least 90%, at least 95%, at least 98%, or at least 99% to SEQ ID NO: 27.

In an embodiment the composition comprises one or more endoglucanases, one or more cellobiohydrolases, one or more beta-glucosidases, at least one beta-mannosidase, and one mannanase, wherein the beta-mannosidase is selected from *A. niger* beta-mannosidase shown as SEQ ID NO: 12 or a beta-mannosidase having a sequence identity of at least 70%, e.g., at least 75%, at least 80%, at least 85%, at least 90%, at least 95%, at least 98%, or at least 99% to SEQ ID NO: 12, and wherein the mannanase is selected from *C. maritima* mannanase shown as SEQ ID NO: 35 or a mannase having a sequence identity of at least 70%, e.g., at least 75%, at least 80%, at least 85%, at least 90%, at least 95%, at least 98%, or at least 99% to SEQ ID NO: 35.

In an embodiment the composition comprises one or more endoglucanases, one or more cellobiohydrolases, one or more beta-glucosidases, at least one beta-mannosidase, and one mannanase, wherein the beta-mannosidase is selected from *A. niger* beta-mannosidase shown as SEQ ID NO: 12 or a beta-mannosidase having a sequence identity of at least 70%, e.g., at least 75%, at least 80%, at least 85%, at least 90%, at least 95%, at least 98%, or at least 99% to SEQ ID NO: 12, and wherein the mannanase is selected from *T. leycettanus* mannanase shown as SEQ ID NO: 34 or a mannase having a sequence identity of at least 70%, e.g., at least 75%, at least 80%, at least 85%, at least 90%, at least 95%, at least 98%, or at least 99% to SEQ ID NO: 34.

In a further embodiment the composition comprises an *Aspergillus fumigatus* GH10 xylanase (WO 2006/078256), an *Aspergillus fumigatus* beta-xylosidase (WO 2011/057140), a *Trichoderma reesei* cellulase preparation containing *Aspergillus fumigatus* cellobiohydrolase I (WO 2011/057140), *Aspergillus fumigatus* cellobiohydrolase II (WO 2011/057140), *Aspergillus fumigatus* beta-glucosidase variant (WO 2012/044915), and *Penicillium* sp. (*emersonii*) AA9 polypeptide (WO 2011/041397), and *A. niger* beta-mannosidase shown as SEQ ID NO: 12 or a beta-mannosidase having a sequence identity of at least 70%, e.g., at least 75%, at least 80%, at least 85%, at least 90%, at least 95%, at least 98%, or at least 99% to SEQ ID NO: 12, and a mannanase shown as SEQ ID NO: 26, SEQ ID NO: 27, SEQ ID NO: 34, SEQ ID NO: 35 or a mannase having a sequence identity of at least 70%, e.g., at least 75%, at least 80%, at least 85%, at least 90%, at least 95%, at least 98%, or at least 99% to SEQ ID NO: 26, SEQ ID NO: 27, SEQ ID NO: 34, SEQ ID NO: 35.

In a further embodiment the composition comprises an *Aspergillus fumigatus* GH10 xylanase (WO 2006/078256), an *Aspergillus fumigatus* beta-xylosidase (WO 2011/057140), a *Trichoderma reesei* cellulase preparation containing *Aspergillus fumigatus* cellobiohydrolase I (WO 2011/057140), *Aspergillus fumigatus* cellobiohydrolase II (WO 2011/057140), *Aspergillus fumigatus* beta-glucosidase variant (WO 2012/044915), and *Penicillium* sp. (*emersonii*) AA9 polypeptide (WO 2011/041397), and *A. niger* beta-mannosidase shown as SEQ ID NO: 12 or a beta-mannosidase having a sequence identity of at least 70%, e.g., at least 75%, at least 80%, at least 85%, at least 90%, at least 95%, at least 98%, or at least 99% to SEQ ID NO: 12, and a mannanase shown as SEQ ID NO: 34 or a mannase having a sequence identity of at least 70%, e.g., at least 75%, at least 80%, at least 85%, at least 90%, at least 95%, at least 98%, or at least 99% to SEQ ID NO: 34.

In one aspect, the enzyme composition comprises or further comprises one or more (e.g., several) proteins selected from the group consisting of an acetylmannan esterase, an acetylxylan esterase, an alpha-galactosidase, an arabinanase, an arabinofuranosidase, a cellulose inducible protein (CIP), a coumaric acid esterase, an esterase, an expansin, a feruloyl esterase, a glucuronidase, a glucuronoyl esterase, a ligninolytic enzyme, an oxidoreductase, a pectinase, a protease, and a swollenin.

In one aspect, the enzyme composition comprises an acetylmannan esterase.

In another aspect, the enzyme composition comprises an acetylxylan esterase. Examples of acetylxylan esterases include, but are not limited to, acetylxylan esterases from *Aspergillus aculeatus* (WO 2010/108918), *Chaetomium globosum* (UniProt:Q2 GWX4), *Chaetomium gracile* (GeneSeqP:AAB82124), *Humicola insolens* DSM 1800 (WO 2009/073709), *Hypocrea jecorina* (WO 2005/001036), *Myceliophtera thermophila* (WO 2010/014880), *Neuro-* spora crassa (U ni Prot: q7s259), *Phaeosphaeria nodorum* (UniProt:Q0UHJ1), and *Thielavia terrestris* NRRL 8126 (WO 2009/042846).

In another aspect, the enzyme composition comprises an alpha-galactosidase. Examples of alpha-galactosidases include, but are not limited to, an alpha-galactosidase from *Aspergillus aculeatus, Aspergillus niger, Emericella nidulans*, and *Talaromyces emersonii*. In an embodiment, the alpha-galactosidase has a sequence identity of at least 70%, e.g., at least 75%, at least 80%, at least 85%, at least 90%, or at least 95%, to SEQ ID NO: 9.

In another aspect, the enzyme composition comprises an arabinanase (e.g., alpha-L-arabinanase).

In another aspect, the enzyme composition comprises an arabinofuranosidase (e.g., alpha-L-arabinofuranosidase). Examples of arabinofuranosidases include, but are not limited to, arabinofuranosidases from *Aspergillus niger* (GeneSeqP:AAR94170), *Humicola insolens* DSM 1800 (WO 2006/114094 and WO 2009/073383), and *M. giganteus* (WO 2006/114094).

In another aspect, the enzyme composition comprises a cellulose inducible protein (CIP).

In another aspect, the enzyme composition comprises a coumaric acid esterase.

In another aspect, the enzyme composition comprises an esterase.

In another aspect, the enzyme composition comprises an expansin.

In another aspect, the enzyme composition comprises a feruloyl esterase. Examples of feruloyl esterases (ferulic acid esterases) include, but are not limited to, feruloyl esterases form *Humicola insolens* DSM 1800 (WO 2009/076122), *Neosartorya fischeri* (UniProt:A1D9T4), *Neurospora crassa* (UniProt:Q9HGR3), *Penicillium aurantiogriseum* (WO 2009/127729), and *Thielavia terrestris* (WO 2010/053838 and WO 2010/065448).

In another aspect, the enzyme composition comprises a glucuronidase (e.g., alpha-D-glucuronidase). Examples of alpha-glucuronidases include, but are not limited to, alpha-glucuronidases from *Aspergillus clavatus* (UniProt:alcc12), *Aspergillus fumigatus* (SwissProt:Q4WW45), *Aspergillus niger* (UniProt:Q96WX9), *Aspergillus terreus* (SwissProt:Q0CJP9), *Humicola insolens* (WO 2010/014706), *Penicillium aurantiogriseum* (WO 2009/068565), *Talaromyces emersonii* (UniProt:Q8X211), and *Trichoderma reesei* (UniProt:Q99024).

In another aspect, the enzyme composition comprises a glucuronoyl esterase.

In another aspect, the enzyme composition comprises a ligninolytic enzyme. In an embodiment, the ligninolytic enzyme is a manganese peroxidase. In another embodiment, the ligninolytic enzyme is a lignin peroxidase. In another embodiment, the ligninolytic enzyme is a $H_2O_2$-producing enzyme.

In another aspect, the enzyme composition comprises an oxidoreductase. In an embodiment, the oxidoreductase is a catalase. In another embodiment, the oxidoreductase is a laccase. In another embodiment, the oxidoreductase is a peroxidase. Examples of oxidoreductases include, but are not limited to, *Aspergillus lentilus* catalase, *Aspergillus fumigatus* catalase, *Aspergillus niger* catalase, *Aspergillus oryzae* catalase, *Humicola insolens* catalase, *Neurospora crassa* catalase, *Penicillium emersonii* catalase, *Scytalidium thermophilum* catalase, *Talaromyces stipitatus* catalase, *Thermoascus aurantiacus* catalase, *Coprinus cinereus* laccase, *Myceliophthora thermophila* laccase, *Polyporus pinsitus* laccase, *Pycnoporus cinnabarinus* laccase, *Rhizoctonia solani* laccase, *Streptomyces coelicolor* laccase, *Coprinus cinereus* peroxidase, Soy peroxidase, Royal palm peroxidase.

In another aspect, the enzyme composition comprises a pectinase.

In another aspect, the enzyme composition comprises a protease.

In another aspect, the enzyme composition comprises a swollenin.

In another aspect, the enzyme composition comprises a second beta-glucosidase.

In another aspect, the enzyme composition comprises a second beta-xylosidase.

In another aspect, the enzyme composition comprises a second cellobiohydrolase I.

In another aspect, the enzyme composition comprises a second cellobiohydrolase II.

In another aspect, the enzyme composition comprises a second endoglucanase, a third endoglucanase and/or a fourth endoglucanase, each of which may be an endoglucanase I, an endoglucanase II, an endoglucanase III, or endoglucanase V.

In another aspect, the enzyme composition comprises a second xylanase.

In another aspect, the enzyme composition comprises a *Trichoderma* whole cellulase composition, e.g., a *Trichoderma reesei* whole cellulase composition. A whole cellulase preparation includes all of the cellulase components naturally produced by a strain of *Trichoderma*, e.g., *Trichoderma reesei*.

In the processes of the present invention, the enzyme(s) can be added prior to or during saccharification, saccharification and fermentation, or fermentation.

One or more components of the enzyme composition may be native proteins, recombinant proteins, or a combination of native proteins and recombinant proteins. For example, one or more components may be native proteins of a cell, which is used as a host cell to express recombinantly one or more other components of the enzyme composition. It is understood herein that the recombinant proteins may be heterologous and/or native to the host cell. One or more components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes depend on several factors including, but not limited to, the mixture of cellulolytic enzymes and/or hemicellulolytic enzymes, the mannan-containing cellulosic material, the concentration of mannan-containing cellulosic material, the pretreatment(s) of the mannan-containing cellulosic material, temperature, time, pH, and inclusion of a fermenting organism (e.g., for Simultaneous Saccharification and Fermentation).

In one aspect, an effective amount of a cellulolytic or hemicellulolytic enzyme to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In another aspect, an effective amount of each polypeptide to the cellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material.

In another aspect, an effective amount of each polypeptide to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material, e.g., AA9 polypeptides can be derived or obtained from any suitable origin, including, archaeal, bacterial, fungal, yeast, plant, or animal origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained by, e.g., site-directed mutagenesis or shuffling.

Each polypeptide may be a bacterial polypeptide. For example, each polypeptide may be a Gram-positive bacterial polypeptide having enzyme activity, or a Gram-negative bacterial polypeptide having enzyme activity.

Each polypeptide may also be a fungal polypeptide, e.g., a yeast polypeptide or a filamentous fungal polypeptide.

Chemically modified or protein engineered mutants of polypeptides may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host can be a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLIC® CTec3 (Novozymes A/S), CELLUCLAST® (Novozymes A/S), NOVOZYM™ 188 (Novozymes A/S), SPEZYME™ CP (Genencor Int.), ACCELLERASE™ TRIO (DuPont), FILTRASE® NL (DSM); METHAPLUS® S/L 100 (DSM), ROHAMENT™ 7069 W (Röhm GmbH), or ALTERNAFUEL® CMAX3™ (Dyadic International, Inc.). The cellulolytic enzyme preparation is added in an amount effective from about 0.001 to about 5.0 wt. % of solids, e.g., about 0.025 to about 4.0 wt. % of solids or about 0.005 to about 2.0 wt. % of solids.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), CELLIC® HTec3 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK), ALTERNA FUEL 100P (Dyadic), and ALTERNA FUEL 200P (Dyadic).

The enzymes may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, C A, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, N Y, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Processes for Producing a Fermentation Product

The present invention also relates to a process for producing a fermentation product, comprising:

(a) saccharifying a mannan-containing cellulosic material with an enzyme composition of the invention;

(b) fermenting the saccharified cellulosic material with a fermenting microorganism to produce the fermentation product; and (c) recovering the fermentation product from the fermentation.

Pretreatment

The process of the present invention may further comprise pretreating the mannan-containing cellulosic material prior to contacting an aqueous slurry of the mannan-containing cellulosic material with an enzyme composition of the present invention. Any pretreatment process known in the art can be used to disrupt plant cell wall components of the mannan-containing cellulosic material (Chandra et al., 2007, *Adv. Biochem. Engin./Biotechnol.* 108: 67-93; Galbe and Zacchi, 2007, *Adv. Biochem. Engin./Biotechnol.* 108: 41-65;

Hendriks and Zeeman, 2009, *Bioresource Technology* 100: 10-18; Mosier et al., 2005, *Bioresource Technology* 96: 673-686; Taherzadeh and Karimi, 2008, *Int. J. Mol. Sci.* 9: 1621-1651; Yang and Wyman, 2008, *Biofuels Bioproducts and Biorefining-Biofpr.* 2: 26-40).

The mannan-containing cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, biological pretreatment, and sulfite cooking. Additional pretreatments include ammonia percolation, ultrasound, electroporation, microwave, supercritical $CO_2$, supercritical $H_2O$, ozone, ionic liquid, and gamma irradiation pretreatments.

The mannan-containing cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the mannan-containing cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on optional addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on the temperature and optional addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 2002/0164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze expansion (AFEX), ammonia percolation (APR), ionic liquid, and organosolv pretreatments.

A chemical catalyst such as $H_2SO_4$ or $SO_2$ (typically 0.3 to 5% w/w) is sometimes added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technology* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze expansion (AFEX) pretreatment.

Lime pretreatment is performed with calcium oxide or calcium hydroxide at temperatures of 85-150° C. and residence times from 1 hour to several days (Wyman et al., 2005, *Bioresource Technology* 96: 1959-1966; Mosier et al., 2005, supra). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technology* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber expansion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technology* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. Biotechnol.*

105-108: 69-85, and Mosier et al., 2005, supra, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt. % acid, e.g., 0.05 to 5 wt. % acid or 0.1 to 2 wt. % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the mannan-containing cellulosic material is present during pretreatment in amounts preferably between 10-80 wt. %, e.g., 20-70 wt. % or 30-60 wt. %, such as around 40 wt. %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperature in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., *ACS Symposium Series* 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, *Enz. Microb. Tech.* 18: 312-331; and Vallander and Eriksson, 1990, *Adv. Biochem. Eng./Biotechnol.* 42: 63-95).

Sulfite cooking: This pretreatment is described in US 2011/0250638 and involves pretreatment of a mannan-containing cellulosic material in a sulphite cooking step.

Saccharification

In the hydrolysis step, also known as saccharification, the cellulosic material, e.g., pretreated, is hydrolyzed by an enzyme composition of the present invention to break down cellulose and/or hemicellulose to fermentable sugars, such as glucose, cellobiose, xylose, xylulose, arabinose, mannose, galactose, and/or soluble oligosaccharides. The enzymes can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzymes(s), i.e., optimal for the enzyme(s). The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 4.5 to about 5.5. The dry solids content is in the range of preferably about 5 to about 50 wt. %, e.g., about 10 to about 40 wt. % or about 20 to about 30 wt. %.

Fermentation

The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous.

Any suitable hydrolyzed cellulosic material can be used in the fermentation step in practicing the present invention. The material is generally selected based on economics, i.e., costs per equivalent sugar potential, and recalcitrance to enzymatic conversion.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol Biotechnol.* 69: 627-642.

Examples of fermenting microorganisms that can ferment hexose sugars include bacterial and fungal organisms, such as yeast. Yeast include strains of *Candida, Kluyveromyces,* and *Saccharomyces*, e.g., *Candida sonorensis, Kluyveromyces marxianus,* and *Saccharomyces cerevisiae.*

Examples of fermenting organisms that can ferment pentose sugars in their native state include bacterial and fungal organisms, such as some yeast. Xylose fermenting yeast include strains of *Candida*, preferably *C. sheatae* or *C. sonorensis*; and strains of *Pichia*, e.g., *P. stipitis*, such as *P. stipitis* CBS 5773. Pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum,* and *Zymomonas mobilis* (Philippidis, 1996, supra).

Other fermenting organisms include strains of *Bacillus*, such as *Bacillus coagulans; Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae; Clostridium*, such as *C. acetobutylicum, C. thermocellum,* and *C. phytofermentans; E. coli*, especially *E. coli* strains that have been genetically modified to improve the yield of ethanol; *Geobacillus* sp.; *Hansenula*, such as *Hansenula anomala; Klebsiella*, such as *K. oxytoca; Kluyveromyces*, such as *K. marxianus, K. lactis, K. thermotolerans,* and *K. fragilis; Schizosaccharomyces*, such as *S. pombe; Thermoanaerobacter*, such as *Thermoanaerobacter saccharolyticum;* and *Zymomonas*, such as *Zymomonas mobilis.*

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In an aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, *Appl. Biochem. Biotechnol.* 39-40: 135-147; Ho et al., 1998, *Appl. Environ. Microbiol.* 64: 1852-1859; Kotter and Ciriacy, 1993, *Appl. Microbiol. Biotechnol.* 38: 776-783; Walfridsson et al., 1995, *Appl. Environ. Microbiol.* 61: 4184-4190; Kuyper et al., 2004, *FEMS Yeast Research* 4: 655-664; Beall et al., 1991, *Biotech. Bioeng.* 38: 296-303; Ingram et al., 1998, *Biotechnol. Bioeng.* 58: 204-214; Zhang et al., 1995, *Science* 267: 240-243; Deanda et al., 1996, *Appl. Environ. Microbiol.* 62: 4465-4470; WO 03/062430).

In one aspect, the fermenting organism comprises polynucleotides encoding the enzymes in the enzyme composition.

The fermenting microorganism is typically added to the degraded cellulosic material or hydrolyzate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism is applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2\times10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g., pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In one aspect, the fermentation product is an alcohol. The term "alcohol" encompasses a substance that contains one or more hydroxyl moieties. The alcohol can be, but is not limited to, n-butanol, isobutanol, ethanol, methanol, arabinitol, butanediol, ethylene glycol, glycerin, glycerol, 1,3-propanediol, sorbitol, xylitol. See, for example, Gong et al., 1999, Ethanol production from renewable resources, in *Advances in Biochemical Engineering/Biotechnology*, Scheper, T., ed., Springer-Verlag Berlin Heidelberg, Germany, 65: 207-241; Silveira and Jonas, 2002, *Appl. Microbiol. Biotechnol.* 59: 400-408; Nigam and Singh, 1995, *Process Biochemistry* 30(2): 117-124; Ezeji et al., 2003, *World Journal of Microbiology and Biotechnology* 19(6): 595-603.

In another aspect, the fermentation product is an alkane. The alkane may be an unbranched or a branched alkane. The alkane can be, but is not limited to, pentane, hexane, heptane, octane, nonane, decane, undecane, or dodecane.

In another aspect, the fermentation product is a cycloalkane. The cycloalkane can be, but is not limited to, cyclopentane, cyclohexane, cycloheptane, or cyclooctane.

In another aspect, the fermentation product is an alkene. The alkene may be an unbranched or a branched alkene. The alkene can be, but is not limited to, pentene, hexene, heptene, or octene.

In another aspect, the fermentation product is an amino acid. The organic acid can be, but is not limited to, aspartic acid, glutamic acid, glycine, lysine, serine, or threonine. See, for example, Richard and Margaritis, 2004, *Biotechnology and Bioengineering* 87(4): 501-515.

In another aspect, the fermentation product is a gas. The gas can be, but is not limited to, methane, $H_2$, $CO_2$, or CO. See, for example, Kataoka et al., 1997, *Water Science and Technology* 36(6-7): 41-47; and Gunaseelan, 1997, *Biomass and Bioenergy* 13(1-2): 83-114.

In another aspect, the fermentation product is isoprene.

In another aspect, the fermentation product is a ketone. The term "ketone" encompasses a substance that contains one or more ketone moieties. The ketone can be, but is not limited to, acetone.

In another aspect, the fermentation product is an organic acid. The organic acid can be, but is not limited to, acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, or xylonic acid. See, for example, Chen and Lee, 1997, *Appl. Biochem. Biotechnol.* 63-65: 435-448.

In another aspect, the fermentation product is polyketide.

Recovery

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Processes and Uses According to the Invention

The present invention relates to processes for degrading mannan-containing cellulosic material, comprising: treating the cellulosic material with an enzyme composition of the invention. More particularly the invention relates to a process for producing a fermentation product, comprising:

(a) saccharifying a mannan-containing cellulosic material with an enzyme composition of the invention;

(b) fermenting the saccharified cellulosic material with a fermenting microorganism to produce the fermentation product; and (c) recovering the fermentation product from the fermentation.

In another aspect the invention relates to a process for producing a fermentation product, the process comprising; a) contacting an aqueous slurry of a mannan-containing cellulosic material with an enzyme composition of the present invention to produce a soluble hydrolyzate, and b) contacting the soluble hydrolyzate with a fermenting organism to produce a fermentation product.

In particular the fermentation product is an alcohol, more particularly ethanol.

The mannan-containing cellulosic material is in a particular embodiment selected from plant material derived from an *Aracaceae* sp. such as *Cocos mucifera, Elaeis guineensis, Elaeis malanococca*, an *Coffea* sp., an *Cyamopsis* sp. such as *Cyamopsis tetragonoloba* (guar bean).

In one embodiment the mannan-containing cellulosic material comprises coffee waste, guar meal, palm kernel cake, palm kernel meal and/or copra cake.

In another embodiment the mannan-containing cellulosic material is softwood.

In another embodiment the mannan-containing cellulosic material is municipal solid waste (MSW).

The invention further relates to a use of a mannase and a beta-manosidase in combination with a cellulase composition for hydrolysing a mannan-containing cellulosic material, wherein the mannanase is selected from the group consisting of *Aspergillus niger* mannanase, *Trichoderma reesei* mannanase, *C. maritima* mannanase or *Talaromyces leycettanus* mannanase. In a particular embodiment the beta-mannosidase is *Aspergillus niger* beta-mannosidase.

In the processes and uses described herein, preferably the beta-mannosidase is selected from the beta-mannosidase shown as SEQ ID NO: 12 or a beta-mannosidase having a sequence identity of at least 70%, e.g., at least 75%, at least 80%, at least 85%, at least 90%, at least 95%, at least 98%, or at least 99% to SEQ ID NO: 12. The mannanase is preferably selected from *T. leycettanus* mannanase, or the mannanase shown as SEQ ID NO: 34 or a mannase having a sequence identity of at least 70%, e.g., at least 75%, at least 80%, at least 85%, at least 90%, at least 95%, at least 98%, or at least 99% to SEQ ID NO: 34. In another preferred embodiment the mannanase is a *Corollospora maritime* mannanase, particularly the mannanase shown in SEQ ID NO: 35 or a beta-mannosidase having a sequence identity of at least 70%, e.g., at least 75%, at least 80%, at least 85%, at least 90%, or at least 95%, or at least 98% or at least 99% to SEQ ID NO: 35.

The present invention is further described by the following numbered paragraphs:

Paragraph [1]. An enzyme composition comprising one or more endoglucanases, one or more cellobiohydrolases, one or more beta-glucosidases, at least one beta-mannosidase, and at least one mannanase, wherein the mannanase is selected from the group consisting of *Aspergillus niger* mannanase, *Trichoderma reesei* mannanase, *Corollospora maritima* mannanase or *Talaromyces leycettanus* mannanase.

Paragraph [2]. The composition of paragraph 1, wherein the beta-mannosidase is *Aspergillus niger* beta-mannosidase.

Paragraph [3]. The enzyme composition of paragraph 1, further comprising one or more of an AA9 polypeptide, a beta-xylosidase, a cellobiohydrolase I and a cellobiohydrolase II, or a xylanase.

Paragraph [4]. The enzyme composition of paragraph 3, which comprises the AA9 polypeptide in an amount of 0.05-4 mg enzyme protein/g total solids (TS), e.g., 0.1-3, 0.2-2, and 0.3-1 mg enzyme protein/g TS.

Paragraph [5]. The enzyme composition of any of paragraphs 1-4, which comprises the beta-glucosidase in an amount of 0.05-4 mg enzyme protein/g total solids (TS), e.g., 0.1-3, 0.2-2, and 0.3-1 mg enzyme protein/g TS.

Paragraph [6]. The enzyme composition of any of paragraphs 1-5, which comprises the beta-mannosidase in an amount of 0.05-4 mg enzyme protein/g total solids (TS), e.g., 0.1-3, 0.2-2, and 0.3-1 mg enzyme protein/g TS.

Paragraph [7]. The enzyme composition of any of paragraphs 1-6, which comprises the beta-xylosidase in an amount of 0.05-4 mg enzyme protein/g total solids (TS), e.g., 0.1-3, 0.2-2, and 0.3-1 mg enzyme protein/g TS.

Paragraph [8]. The enzyme composition of any of paragraphs 1-7, which comprises the cellobiohydrolase I in an amount of 0.05-4 mg enzyme protein/g total solids (TS), e.g., 0.1-3, 0.2-2, and 0.3-1 mg enzyme protein/g TS.

Paragraph [9]. The enzyme composition of any of paragraphs 1-8, which comprises the cellobiohydrolase II in an amount of 0.05-4 mg enzyme protein/g total solids (TS), e.g., 0.1-3, 0.2-2, and 0.3-1 mg enzyme protein/g TS.

Paragraph [10]. The enzyme composition of any of paragraphs 1-9, which comprises the endoglucanase in an amount of 0.05-4 mg enzyme protein/g total solids (TS), e.g., 0.1-3, 0.2-2, and 0.3-1 mg enzyme protein/g TS.

Paragraph [11]. The enzyme composition of any of paragraphs 1-10, which comprises the alpha-galactosidase in an amount of 0.05-4 mg enzyme protein/g total solids (TS), e.g., 0.1-3, 0.2-2, and 0.3-1 mg enzyme protein/g TS.

Paragraph [12]. The enzyme composition of any of paragraphs 1-11, which comprises the mannanase in an amount of 0.05-4 mg enzyme protein/g total solids (TS), e.g., 0.1-3, 0.2-2, and 0.3-1 mg enzyme protein/g TS.

Paragraph [13]. The enzyme composition of any of paragraphs 1-12, which comprises the xylanase in an amount of 0.05-4 mg enzyme protein/g total solids (TS), e.g., 0.1-3, 0.2-2, and 0.3-1 mg enzyme protein/g TS.

Paragraph [14]. The enzyme composition of any of paragraphs 1-13, wherein the AA9 polypeptide has a sequence identity of at least 70%, e.g., at least 75%, at least 80%, at least 85%, at least 90%, or at least 95%, to SEQ ID NO: 1.

Paragraph [15]. The enzyme composition of any of paragraphs 1-13, wherein the AA9 polypeptide has a sequence identity of at least 70%, e.g., at least 75%, at least 80%, at least 85%, at least 90%, or at least 95%, to SEQ ID NO: 2.

Paragraph [16]. The enzyme composition of any of paragraphs 1-13, wherein the AA9 polypeptide has a sequence identity of at least 70%, e.g., at least 75%, at least 80%, at least 85%, at least 90%, or at least 95%, to SEQ ID NO: 3.

Paragraph [17]. The enzyme composition of any of paragraphs 1-13, wherein the AA9 polypeptide has a sequence identity of at least 70%, e.g., at least 75%, at least 80%, at least 85%, at least 90%, or at least 95%, to SEQ ID NO: 4.

Paragraph [18]. The enzyme composition of any of paragraphs 1-13, wherein the AA9 polypeptide has a sequence identity of at least 70%, e.g., at least 75%, at least 80%, at least 85%, at least 90%, or at least 95%, to SEQ ID NO: 5.

Paragraph [19]. The enzyme composition of any of paragraphs 1-13, wherein the AA9 polypeptide has a sequence identity of at least 70%, e.g., at least 75%, at least 80%, at least 85%, at least 90%, or at least 95%, to SEQ ID NO: 6.

Paragraph [20]. The enzyme composition of any of paragraphs 1-13, wherein the AA9 polypeptide has a sequence identity of at least 70%, e.g., at least 75%, at least 80%, at least 85%, at least 90%, or at least 95%, to SEQ ID NO: 7.

Paragraph [21]. The enzyme composition of any of paragraphs 1-13, wherein the AA9 polypeptide has a sequence identity of at least 70%, e.g., at least 75%, at least 80%, at least 85%, at least 90%, or at least 95%, to SEQ ID NO: 8.

Paragraph [22]. The enzyme composition of any of paragraphs 1-21, wherein the beta-glucosidase has a sequence identity of at least 70%, e.g., at least 75%, at least 80%, at least 85%, at least 90%, or at least 95%, to SEQ ID NO: 10.

Paragraph [23]. The enzyme composition of any of paragraphs 1-21, wherein the beta-glucosidase has a sequence identity of at least 70%, e.g., at least 75%, at least 80%, at least 85%, at least 90%, or at least 95%, to SEQ ID NO: 11.

Paragraph [24]. The enzyme composition of any of paragraphs 1-23, wherein the beta-mannosidase has a sequence identity of at least 70%, e.g., at least 75%, at least 80%, at least 85%, at least 90%, or at least 95%, to SEQ ID NO: 12.

Paragraph [25]. The enzyme composition of any of paragraphs 1-24, wherein the beta-xylosidase has a sequence identity of at least 70%, e.g., at least 75%, at least 80%, at least 85%, at least 90%, or at least 95%, to SEQ ID NO: 13.

Paragraph [26]. The enzyme composition of any of paragraphs 1-24, wherein the beta-xylosidase has a sequence identity of at least 70%, e.g., at least 75%, at least 80%, at least 85%, at least 90%, or at least 95%, to SEQ ID NO: 14.

Paragraph [27]. The enzyme composition of any of paragraphs 1-24, wherein the beta-xylosidase has a sequence identity of at least 70%, e.g., at least 75%, at least 80%, at least 85%, at least 90%, or at least 95%, to SEQ ID NO: 33.

Paragraph [28]. The enzyme composition of any of paragraphs 1-27, wherein the cellobiohydrolase I has a sequence identity of at least 70%, e.g., at least 75%, at least 80%, at least 85%, at least 90%, or at least 95%, to SEQ ID NO: 16.

Paragraph [29]. The enzyme composition of any of paragraphs 1-27, wherein the cellobiohydrolase I has a sequence identity of at least 70%, e.g., at least 75%, at least 80%, at least 85%, at least 90%, or at least 95%, to SEQ ID NO: 18.

Paragraph [30]. The enzyme composition of any of paragraphs 1-29, wherein the cellobiohydrolase II has a sequence identity of at least 70%, e.g., at least 75%, at least 80%, at least 85%, at least 90%, or at least 95%, to SEQ ID NO: 15.

Paragraph [31]. The enzyme composition of any of paragraphs 1-29, wherein the cellobiohydrolase II has a sequence identity of at least 70%, e.g., at least 75%, at least 80%, at least 85%, at least 90%, or at least 95%, to SEQ ID NO: 17.

Paragraph [32]. The enzyme composition of any of paragraphs 1-29, wherein the cellobiohydrolase II has a sequence identity of at least 70%, e.g., at least 75%, at least 80%, at least 85%, at least 90%, or at least 95%, to SEQ ID NO: 19.

Paragraph [33]. The enzyme composition of any of paragraphs 1-32, wherein the endoglucanase is an endoglucanase I.

Paragraph [34]. The enzyme composition of any of paragraphs 1-32, wherein the endoglucanase is an endoglucanase II.

Paragraph [35]. The enzyme composition of any of paragraphs 1-32, wherein the endoglucanase is an endoglucanase III.
Paragraph [36]. The enzyme composition of any of paragraphs 1-32, wherein the endoglucanase is an endoglucanase V.
Paragraph [37]. The enzyme composition of any of paragraphs 1-32, wherein the endoglucanase has a sequence identity of at least 70%, e.g., at least 75%, at least 80%, at least 85%, at least 90%, or at least 95%, to SEQ ID NO: 20.
Paragraph [38]. The enzyme composition of any of paragraphs 1-32, wherein the endoglucanase has a sequence identity of at least 70%, e.g., at least 75%, at least 80%, at least 85%, at least 90%, or at least 95%, to SEQ ID NO: 21.
Paragraph [39]. The enzyme composition of any of paragraphs 1-32, wherein the endoglucanase has a sequence identity of at least 70%, e.g., at least 75%, at least 80%, at least 85%, at least 90%, or at least 95%, to SEQ ID NO: 23.
Paragraph [40]. The enzyme composition of any of paragraphs 1-32, wherein the endoglucanase has a sequence identity of at least 70%, e.g., at least 75%, at least 80%, at least 85%, at least 90%, or at least 95%, to SEQ ID NO: 22.
Paragraph [41]. The enzyme composition of any of paragraphs 1-32, wherein the endoglucanase has a sequence identity of at least 70%, e.g., at least 75%, at least 80%, at least 85%, at least 90%, or at least 95%, to SEQ ID NO: 24.
Paragraph [42]. The enzyme composition of any of paragraphs 1-32, wherein the endoglucanase has a sequence identity of at least 70%, e.g., at least 75%, at least 80%, at least 85%, at least 90%, or at least 95%, to SEQ ID NO: 25.
Paragraph [43]. The enzyme composition of any of paragraphs 1-42, wherein the mannanase has a sequence identity of at least 70%, e.g., at least 75%, at least 80%, at least 85%, at least 90%, or at least 95%, to SEQ ID NO: 26.
Paragraph [44]. The enzyme composition of any of paragraphs 1-42, wherein the mannanase has a sequence identity of at least 70%, e.g., at least 75%, at least 80%, at least 85%, at least 90%, or at least 95%, to SEQ ID NO: 27.
Paragraph [45]. The enzyme composition of any of paragraphs 1-42, wherein the mannanase has a sequence identity of at least 70%, e.g., at least 75%, at least 80%, at least 85%, at least 90%, or at least 95%, to SEQ ID NO: 34.
Paragraph [46]. The enzyme composition of any of paragraphs 1-42, wherein the mannanase has a sequence identity of at least 70%, e.g., at least 75%, at least 80%, at least 85%, at least 90%, or at least 95%, to SEQ ID NO: 35.
Paragraph [47]. The enzyme composition of any of paragraphs 1-46, wherein the xylanase has a sequence identity of at least 70%, e.g., at least 75%, at least 80%, at least 85%, at least 90%, or at least 95%, to SEQ ID NO: 28.
Paragraph [48]. The enzyme composition of any of paragraphs 1-46, wherein the xylanase has a sequence identity of at least 70%, e.g., at least 75%, at least 80%, at least 85%, at least 90%, or at least 95%, to SEQ ID NO: 29.
Paragraph [49]. The enzyme composition of any of paragraphs 1-46, wherein the xylanase has a sequence identity of at least 70%, e.g., at least 75%, at least 80%, at least 85%, at least 90%, or at least 95%, to SEQ ID NO: 30.
Paragraph [50]. The enzyme composition of any of paragraphs 1-46, wherein the xylanase has a sequence identity of at least 70%, e.g., at least 75%, at least 80%, at least 85%, at least 90%, or at least 95%, to SEQ ID NO: 31.
Paragraph [51]. The enzyme composition of any of paragraphs 1-46, wherein the xylanase has a sequence identity of at least 70%, e.g., at least 75%, at least 80%, at least 85%, at least 90%, or at least 95%, to SEQ ID NO: 32.
Paragraph [52]. The enzyme composition of any of paragraphs 1-51, further comprising an acetylmannan esterase.
Paragraph [53]. The enzyme composition of any of paragraphs 1-52, further comprising an acetylxylan esterase.
Paragraph [54]. The enzyme composition of any of paragraphs 1-53, further comprising an alpha-galactosidase.
Paragraph [55]. The enzyme composition of paragraph 54, wherein the alpha-galactosidase has a sequence identity of at least 70%, e.g., at least 75%, at least 80%, at least 85%, at least 90%, or at least 95%, to SEQ ID NO: 9.
Paragraph [56]. The enzyme composition of any of paragraphs 1-55, further comprising an arabinanase (e.g., alpha-L-arabinanase).
Paragraph [57]. The enzyme composition of any of paragraphs 1-56, further comprising an arabinofuranosidase (e.g., alpha-L-arabinofuranosidase).
Paragraph [58]. The enzyme composition of any of paragraphs 1-57, further comprising a cellulose inducible protein (CI P).
Paragraph [59]. The enzyme composition of any of paragraphs 1-58, further comprising a coumaric acid esterase.
Paragraph [60]. The enzyme composition of any of paragraphs 1-59, further comprising an esterase.
Paragraph [61]. The enzyme composition of any of paragraphs 1-60, further comprising an expansin.
Paragraph [62]. The enzyme composition of any of paragraphs 1-61, further comprising a feruloyl esterase.
Paragraph [63]. The enzyme composition of any of paragraphs 1-62, further comprising a glucuronidase (e.g., alpha-D-glucuronidase).
Paragraph [64]. The enzyme composition of any of paragraphs 1-63, further comprising a glucuronoyl esterase.
Paragraph [65]. The enzyme composition of any of paragraphs 1-64, further comprising a ligninolytic enzyme.
Paragraph [66]. The enzyme composition of paragraph 65, wherein the ligninolytic enzyme is a manganese peroxidase.
Paragraph [67]. The enzyme composition of paragraph 65, wherein the ligninolytic enzyme is a lignin peroxidase.
Paragraph [68]. m The enzyme composition of paragraph 65, wherein the ligninolytic enzyme is a $H_2O_2$-producing enzyme.
Paragraph [69]. The enzyme composition of any of paragraphs 1-68, further comprising an oxidoreductase.
Paragraph [70]. The enzyme composition of paragraph 69, wherein the oxidoreductase is a catalase.
Paragraph [71]. The enzyme composition of paragraph 69, wherein the oxidoreductase is a laccase.
Paragraph [72]. The enzyme composition of paragraph 69, wherein the oxidoreductase is a peroxidase.
Paragraph [73]. The enzyme composition of any of paragraphs 1-72, further comprising a pectinase.
Paragraph [74]. The enzyme composition of any of paragraphs 1-73, further comprising a protease.
Paragraph [75]. The enzyme composition of any of paragraphs 1-74, further comprising a swollenin.
Paragraph [76]. The enzyme composition of any of paragraphs 1-75, further comprising a second beta-glucosidase (different from the beta-glucosidase).
Paragraph [77]. The enzyme composition of paragraph 76, wherein the second beta-glucosidase has a sequence identity of at least 70%, e.g., at least 75%, at least 80%, at least 85%, at least 90%, or at least 95%, to SEQ ID NO: 10.
Paragraph [78]. The enzyme composition of paragraph 76, wherein the second beta-glucosidase has a sequence identity of at least 70%, e.g., at least 75%, at least 80%, at least 85%, at least 90%, or at least 95%, to SEQ ID NO: 11.

Paragraph [79]. The enzyme composition of any of paragraphs 1-78, further comprising a second beta-xylosidase (different from the beta-xylosidase).

Paragraph [80]. The enzyme composition of paragraph 79, wherein the beta-xylosidase has a sequence identity of at least 70%, e.g., at least 75%, at least 80%, at least 85%, at least 90%, or at least 95%, to SEQ ID NO: 13.

Paragraph [81]. The enzyme composition of paragraph 79, wherein the beta-xylosidase has a sequence identity of at least 70%, e.g., at least 75%, at least 80%, at least 85%, at least 90%, or at least 95%, to SEQ ID NO: 14.

Paragraph [82]. The enzyme composition of paragraph 79, wherein the beta-xylosidase has a sequence identity of at least 70%, e.g., at least 75%, at least 80%, at least 85%, at least 90%, or at least 95%, to SEQ ID NO: 33.

Paragraph [83]. The enzyme composition of any of paragraphs 1-82, further comprising a second cellobiohydrolase I (different from the cellobiohydrolase I).

Paragraph [84]. The enzyme composition of paragraph 83, wherein the second cellobiohydrolase I has a sequence identity of at least 70%, e.g., at least 75%, at least 80%, at least 85%, at least 90%, or at least 95%, to SEQ ID NO: 16.

Paragraph [85]. The enzyme composition of paragraph 84, wherein the second cellobiohydrolase I has a sequence identity of at least 70%, e.g., at least 75%, at least 80%, at least 85%, at least 90%, or at least 95%, to SEQ ID NO: 18.

Paragraph [86]. The enzyme composition of any of paragraphs 1-85, further comprising a second cellobiohydrolase II (different from the cellobiohydrolase II).

Paragraph [87]. The enzyme composition of paragraph 86, wherein the second cellobiohydrolase II has a sequence identity of at least 70%, e.g., at least 75%, at least 80%, at least 85%, at least 90%, or at least 95%, to SEQ ID NO: 15.

Paragraph [88]. The enzyme composition of paragraph 86, wherein the second cellobiohydrolase II has a sequence identity of at least 70%, e.g., at least 75%, at least 80%, at least 85%, at least 90%, or at least 95%, to SEQ ID NO: 17.

Paragraph [89]. The enzyme composition of paragraph 86, wherein the second cellobiohydrolase II has a sequence identity of at least 70%, e.g., at least 75%, at least 80%, at least 85%, at least 90%, or at least 95%, to SEQ ID NO: 19.

Paragraph [90]. The enzyme composition of any of paragraphs 1-89, further comprising a second endoglucanase, a third endoglucanase and/or fourth endoglucanase (each different from the endoglucanase and each other).

Paragraph [91]. The enzyme composition of paragraph 90, wherein the second endoglucanase is an endoglucanase I.

Paragraph [92]. The enzyme composition of paragraph 90, wherein the second endoglucanase is an endoglucanase II.

Paragraph [93]. The enzyme composition of paragraph 90, wherein the second endoglucanase is an endoglucanase III.

Paragraph [94]. The enzyme composition of paragraph 90, wherein the second endoglucanase is an endoglucanase V.

Paragraph [95]. The enzyme composition of any of paragraphs 90-94, wherein the third endoglucanase is an endoglucanase I.

Paragraph [96]. The enzyme composition of any of paragraphs 90-94, wherein the third endoglucanase is an endoglucanase II.

Paragraph [97]. The enzyme composition of any of paragraphs 90-94, wherein the third endoglucanase is an endoglucanase III.

Paragraph [98]. The enzyme composition of any of paragraphs 90-94, wherein the third endoglucanase is an endoglucanase V.

Paragraph [99]. The enzyme composition of any of paragraphs 90-98, wherein the fourth endoglucanase is an endoglucanase I.

Paragraph [100]. The enzyme composition of any of paragraphs 90-98, wherein the fourth endoglucanase is an endoglucanase II.

Paragraph [101]. The enzyme composition of any of paragraphs 90-98, wherein the fourth endoglucanase is an endoglucanase III.

Paragraph [102]. The enzyme composition of any of paragraphs 90-98, wherein the fourth endoglucanase is an endoglucanase V.

Paragraph [103]. The enzyme composition of any of paragraphs 90-102, wherein the endoglucanase has a sequence identity of at least 70%, e.g., at least 75%, at least 80%, at least 85%, at least 90%, or at least 95%, to SEQ ID NO: 20, the second endoglucanase has a sequence identity of at least 70%, e.g., at least 75%, at least 80%, at least 85%, at least 90%, or at least 95%, to SEQ ID NO: 21, the third endoglucanase has a sequence identity of at least 70%, e.g., at least 75%, at least 80%, at least 85%, at least 90%, or at least 95%, to SEQ ID NO: 23, and the fourth endoglucanase has a sequence identity of at least 70%, e.g., at least 75%, at least 80%, at least 85%, at least 90%, or at least 95%, to SEQ ID NO: 22.

Paragraph [104]. The enzyme composition of any of paragraphs 1-103, further comprising a second xylanase (different from the xylanase).

Paragraph [105]. The enzyme composition of paragraph 104, wherein the second xylanase has a sequence identity of at least 70%, e.g., at least 75%, at least 80%, at least 85%, at least 90%, or at least 95%, to SEQ ID NO: 28.

Paragraph [106]. The enzyme composition of paragraph 104, wherein the second xylanase has a sequence identity of at least 70%, e.g., at least 75%, at least 80%, at least 85%, at least 90%, or at least 95%, to SEQ ID NO: 29.

Paragraph [107]. The enzyme composition of paragraph 104, wherein the second xylanase has a sequence identity of at least 70%, e.g., at least 75%, at least 80%, at least 85%, at least 90%, or at least 95%, to SEQ ID NO: 30.

Paragraph [108]. The enzyme composition of paragraph 104, wherein the second xylanase has a sequence identity of at least 70%, e.g., at least 75%, at least 80%, at least 85%, at least 90%, or at least 95%, to SEQ ID NO: 31.

Paragraph [109]. The enzyme composition of paragraph 104, wherein the second xylanase has a sequence identity of at least 70%, e.g., at least 75%, at least 80%, at least 85%, at least 90%, or at least 95%, to SEQ ID NO: 32.

Paragraph [110]. The enzyme composition of any of paragraphs 1-109, further comprising a *Trichoderma* whole cellulase composition.

Paragraph [111]. The enzyme composition of paragraph 110, wherein the *Trichoderma* whole cellulase composition is a *Trichoderma reesei* whole cellulase composition.

Paragraph [112]. A process for degrading a mannan-containing cellulosic material, comprising: treating the cellulosic material with an enzyme composition of any of paragraphs 1-111.

Paragraph [113]. The process of paragraph 112, further comprising pretreating the mannan-containing cellulosic material prior to treatment of the mannan-containing cellulosic material.

Paragraph [114]. The process of paragraph 113, wherein the pretreatment is acid pretreatment carried out using an organic acid, preferably sulphuric acid, acetic acid, citric acid, tartaric acid, succinic acid, and/or mixtures thereof.

Paragraph [115]. The process of any of paragraphs 112-114, further comprising recovering the degraded cellulosic material.

Paragraph [116]. The process of paragraph 115, wherein the degraded cellulosic material is a sugar.

Paragraph [117]. The process of paragraph 116, wherein the sugar is selected from the group consisting of glucose, xylose, mannose, galactose, and arabinose.

Paragraph [118]. A process for producing a fermentation product, comprising:
  (a) saccharifying a mannan-containing cellulosic material with an enzyme composition of any of paragraphs 1-111;
  (b) fermenting the saccharified cellulosic material with a fermenting microorganism to produce the fermentation product; and
  (c) recovering the fermentation product from the fermentation.

Paragraph [119]. The process of paragraph 118, further comprising pretreating the mannan-containing cellulosic material prior to saccharification.

Paragraph [120]. The process of paragraph 118 or 119, wherein the pretreatment is acid pretreatment carried out using an organic acid, preferably sulphuric acid, acetic acid, citric acid, tartaric acid, succinic acid, and/or mixtures thereof.

Paragraph [121]. The process of any of paragraphs 118-120, wherein steps (a) and (b) are performed simultaneously in a simultaneous saccharification and fermentation.

Paragraph [122]. The process of any of paragraphs 118-121, wherein the fermentation product is an alcohol, an alkane, a cycloalkane, an alkene, an amino acid, a gas, isoprene, a ketone, an organic acid, or polyketide.

Paragraph [123]. The process of paragraph 122, wherein the fermentation product is ethanol.

Paragraph [124]. The process of any of paragraphs 118-123, wherein the fermenting microorganism is a yeast.

Paragraph [125]. The process of any of paragraphs 118-124, wherein the fermentation product is recovered by distillation.

Paragraph [126]. The process of any of paragraphs 112-125, wherein the mannan-containing cellulosic material comprises plant material derived from an *Aracaceae* sp. such as *Cocos mucifera, Elaeis guineensis, Elaeis malanococca*, an *Coffea* sp., an *Cyamopsis* sp. such as *Cyamopsis tetragonoloba* (guar bean).

Paragraph [127]. The process of any of paragraphs 112-125, wherein the mannan-containing cellulosic material comprises coffee waste, guar meal, palm kernel cake, palm kernel meal and/or copra cake.

Paragraph [128]. The process of any of paragraphs 112-125, wherein the mannan-containing cellulosic material is softwood.

Paragraph [129]. The process of any of the paragraphs 112-125, wherein the mannan-containing cellulosic material is municipal solid waste.

Paragraph [130]. A use of a mannase and a beta-manosidase in combination with a cellulase composition for hydrolysing a mannan-containing cellulosic material, wherein the mannanase is selected from the group consisting of *Aspergillus niger* mannanase, *Trichoderma reesei* mannanase, *Corollospora maritima* mannanase or *Talaromyces leycettanus* mannanase.

Paragraph [131]. The use according to paragraph 130, wherein the beta-mannosidase is *Aspergillus niger* beta-mannosidase, particularly the beta-mannosidase shown in SEQ ID NO: 12 or a beta-mannosidase having a sequence identity of at least 70%, e.g., at least 75%, at least 80%, at least 85%, at least 90%, or at least 95%, or at least 98% or at least 99% to SEQ ID NO: 12.

Paragraph [132]. The use according to paragraph 130 or 131, wherein the mannanase is a *Talaromyces leycettanus* mannanase, particularly the mannanase shown in SEQ ID NO: 34 or a beta-mannosidase having a sequence identity of at least 70%, e.g., at least 75%, at least 80%, at least 85%, at least 90%, or at least 95%, or at least 98% or at least 99% to SEQ ID NO: 34.

Paragraph [133]. The use according to paragraph 130 or 131, wherein the mannanase is a *Corollospora maritime* mannanase, particularly the mannanase shown in SEQ ID NO: 35 or a beta-mannosidase having a sequence identity of at least 70%, e.g., at least 75%, at least 80%, at least 85%, at least 90%, or at least 95%, or at least 98% or at least 99% to SEQ ID NO: 35.

Paragraph [134]. The use according to any of the paragraphs 130-133, wherein the mannan-containing cellulosic material is softwood or municipal solid waste.

Paragraph [135]. A process for producing a fermentation product, the process comprising; a) contacting an aqueous slurry of a mannan-containing cellulosic material with an enzyme composition of the present invention to produce a soluble hydrolyzate, and b) contacting the soluble hydrolyzate with a fermenting organism to produce a fermentation product.

Materials & Methods

Enzymes

Cellulolytic Enzyme Composition #1: A blend of an *Aspergillus fumigatus* GH10 xylanase (WO 2006/078256) and *Aspergillus fumigatus* beta-xylosidase (WO 2011/057140) with a *Trichoderma reesei* cellulase preparation containing *Aspergillus fumigatus* cellobiohydrolase I (WO 2011/057140), *Aspergillus fumigatus* cellobiohydrolase II (WO 2011/057140), *Aspergillus fumigatus* beta-glucosidase variant (WO 2012/044915), and *Penicillium* sp. (*emersonii*) GH61 polypeptide (WO 2011/041397).

Cellulolytic Enzyme Composition #2: A blend of 87.67% Cellulolytic Enzyme Composition #1 with 5.84% *Aspergillus niger* endo-mannanase (SEQ ID NO: 26); 3.25% *Aspergillus niger* beta-mannosidase (SEQ ID NO: 12); and 3.25% *Aspergillus niger* alpha-galactosidase (SEQ ID NO: 9).

Cellulolytic Enzyme Composition #3: A blend of 86.54% Cellulolytic Enzyme Composition #1 with 8.65% *Aspergillus niger* endo-mannanase (SEQ ID NO: 26) and 4.81% *Aspergillus niger* beta-mannosidase (SEQ ID NO: 12).

Cellulolytic Enzyme Composition #4: A blend of 90% Cellulolytic Enzyme Composition #1 with 5% *Trichoderma reesei* endo-mannanase (SEQ ID NO: 27); and 5% *Aspergillus niger* beta-mannosidase (SEQ ID NO: 12).

Cellulolytic Enzyme Composition #5: A blend of an *Trichophaea saccata* GH10 xylanase (WO2011/057083), *Talaromyces emersonii* beta-xylosidase (SwissProt: Q8X212), with a *Trichoderma reesei* cellulase preparation containing *Aspergillus fumigatus* cellobiohydrolase I (WO 2011/057140), *Aspergillus fumigatus* cellobiohydrolase II (WO 2011/057140), *Aspergillus fumigatus* beta-glucosidase variant (WO 2012/044915), and *Penicillium* sp. (*emersonii*) GH61 polypeptide (WO 2011/041397).

Example 1: Hydrolysis of Softwood

Wood chips from Norway spruce (*Picea abies*) were pretreated with steam in a two stage process as provided below. The first stage was performed at 175° C. for 30 minutes, followed by separation of the solid and liquid fraction by pressing of the wood material. The solid fraction from the first stage was treated in the second stage at 210° C. for 5 minutes. For the hydrolysis experiments described here, only the material from the second stage was used. This material was mechanically refined in a PFI mill according to the standard TAPPI method T248 to varying severities of 5000 (5K) and 20000 (20K) revolutions.

Hydrolysis was performed on a 20 g scale under the following conditions: 5% total solids (TS), 50 mM citrate buffer, pH 5, 50° C. for 72 hours at 20 rpm in a FINEPCR Combi-D24 hybridization incubator.

Cellulolytic Enzyme Composition #1 and Cellulolytic Enzyme Composition #2 were used in the hydrolysis. The enzyme compositions were dosed at 20 and 20.53 mg enzyme per g TS, respectively.

All experiments were performed in triplicate. Samples were taken after 72 hours of hydrolysis. The samples were deactivated at 100° C. for 10 minutes and subsequently diluted 5 times (weight/weight) in 0.005 M $H_2SO_4$. The diluted samples were centrifuged and HPLC samples were taken from the supernatant. The samples were analyzed for glucose by HPLC using a 300×7.8 mm AMINEX® HPX-87H column. Elution was isocratic using 0.005 M $H_2SO_4$ at a column temperature of 65° C. The flow rate was 0.6 mL/minute. Quantification was performed by integration of the glucose signal, using a Waters 2414 Refractive index detector (50° C. in flow cell). HPLC chromatogram processing was performed using Waters Empower software. HPLC data processing was performed using Microsoft Excel. Measured glucose concentrations were adjusted for appropriate dilution.

Table 1 shows the glucose concentration (g glucose/kg hydrolysis slurry) for two different substrates with Cellulolytic Enzyme Compositions #1 and #2.

TABLE 1

| | Glucose concentration (g/kg) after 72 hours hydrolysis | | | | |
|---|---|---|---|---|---|
| Substrate | Cellulolytic Enzyme Composition #1 | Standard deviation | Cellulolytic Enzyme Composition #2 | Standard deviation | |
| 5K | 14.8 | 0.4 | 16.2 | 0.2 | p = 0.0095* |
| 20K | 15.0 | 0.5 | 18.1 | 0.3 | p = 0.0014* |

Cellulolytic Enzyme Composition #2 produced significantly higher glucose concentrations compared to Cellulolytic Enzyme Composition #1.

Example 2: Hydrolysis of Softwood

Softwood chips were pretreated in accordance with the BALI™ concept described by Borregaard in US 2011/0250638. This concept comprises a sulfite cook of the softwood chips.

Hydrolysis was performed on a 20 g scale under the following conditions: 10% total solids (TS), 50 mM citrate buffer, pH 5, 50° C. for 72 hours at 20 rpm in a FINEPCR Combi-D24 hybridization incubator.

Cellulolytic Enzyme Composition #1 and Cellulolytic Enzyme Composition #2 were used in the hydrolysis. The enzyme compositions were dosed at 5, 10 and 15 or 5.13, 10.27 and 15.4 mg enzyme per g TS, respectively. All experiments were performed in triplicate. Samples were taken after 72 hours of hydrolysis. The samples were deactivated at 100° C. for 10 minutes and subsequently diluted 5 times (weight/weight) in 0.005 M $H_2SO_4$. The diluted samples were centrifuged and HPLC samples were taken from the supernatant. The samples were analyzed for glucose by HPLC using a 300×7.8 mm AMINEX® HPX-87H column. Elution was isocratic using 0.005 M $H_2SO_4$ at a column temperature of 65° C. The flow rate was 0.6 mL/minute. Quantification was performed by integration of the glucose signal, using a Waters 2414 Refractive index detector (50° C. in flow cell). HPLC chromatogram processing was performed using Waters Empower software. HPLC data processing was performed using Microsoft Excel. Measured glucose concentrations were adjusted for appropriate dilution.

Table 2 shows the glucose concentration (g glucose/kg hydrolysis slurry) for three different enzyme doses with Cellulolytic Enzyme Compositions #1 and #2.

TABLE 2

| | Glucose concentration (g/kg) after 72 hours hydrolysis | | | | | |
|---|---|---|---|---|---|---|
| Enzyme dose | Cellulolytic Enzyme Composition #1 | Standard deviation | Enzyme dose | Cellulolytic Enzyme Composition #2 | Standard deviation | |
| 5 mg enzyme per g TS | 44.0 | 1.1 | 5.13 mg enzyme per g TS | 52.9 | 1.1 | p = 0.0006* |
| 10 mg enzyme per g TS | 62.4 | 0.9 | 10.27 mg enzyme per g TS | 72.7 | 1.2 | p = 0.0005* |
| 15 mg enzyme per g TS | 71.2 | 3.9 | 15.4 mg enzyme per g TS | 87.2 | 1.3 | p = 0.0133* |

Cellulolytic Enzyme Composition #2 produced significantly higher glucose concentrations compared to Cellulolytic Enzyme Composition #1.

Example 3: Hydrolysis of Softwood

Softwood chips were pretreated in accordance with the BALI™ concept described by Borregaard in US 2011/0250638.

Hydrolysis was performed on 50 g scale under the following conditions: 20% total solids (TS), 50 mM citrate buffer, pH 5, 50° C. for 72 hours with free-fall stirring in a biomass tumbler setup.

Cellulolytic Enzyme Composition #1 and Cellulolytic Enzyme Composition #2 were used in the hydrolysis experiments. The enzyme compositions were dosed at 10 and 15 or 10.27 and 15.4 mg enzyme per g TS, respectively. All experiments were performed in triplicate. Samples were taken after 72 hours of hydrolysis. The samples were deactivated at 100° C. for 10 minutes and subsequently diluted 5 times (weight/weight) in 0.005 M $H_2SO_4$. The diluted samples were centrifuged and HPLC samples were taken from the supernatant. The samples were analyzed for glucose by HPLC using a 300×7.8 mm AMINEX® HPX-87H column. Elution was isocratic using 0.005 M $H_2SO_4$ at a column temperature of 65° C. The flow rate was 0.6 mL/minute. Quantification was performed by integration of the glucose signal, using a Waters 2414 Refractive index detector (50° C. in flow cell). HPLC chromatogram processing was performed using Waters Empower software. HPLC data processing was performed using Microsoft Excel. Measured glucose concentrations were adjusted for appropriate dilution.

For mannose concentration determination, the diluted samples were centrifuged and the supernatants were further volume/volume diluted 20-fold for analysis of mannose. The samples were analyzed for glucose and mannose with a DIONEX® BIOLC® System according to the following method. Samples (10 μl) were loaded onto a DIONEX BIOLC® System equipped with a DIONEX® CARBOPAC™ PA1 analytical column (4×250 mm) (Dionex Corporation, Sunnyvale, Calif., USA) combined with a CARBOPAC™ PA1 guard column (4×50 mm) (Dionex Corporation, Sunnyvale, Calif., USA). The monosaccharides were separated isocratically with 2 mM potassium hydroxide at a flow rate of 1 ml per minute and detected by a pulsed electrochemical detector in the pulsed amperiometric detection mode. Mixtures of arabinose, galactose, glucose, xylose, and mannose (concentration range of each component: 0.0050-0.0750 g per liter) were used as standards. All DIONEX chromatogram processing was performed using Chromeleon software. All DIONEX data processing was performed using Microsoft Excel. Measured sugar concentrations were adjusted for the appropriate dilution factor.

Table 3 shows the glucose concentration (g glucose/kg hydrolysis slurry) for the 2 different enzyme doses with Cellulolytic Enzyme Composition #1 and #2.

Table 4 shows the mannose concentration (g mannose/kg hydrolysis slurry) for the 2 different enzyme doses with Cellulolytic Enzyme Compositions #1 and #2.

TABLE 3

| | Glucose concentration (g/kg) after 72 hours hydrolysis. | | | | | |
|---|---|---|---|---|---|---|
| Enzyme dose | Cellulolytic Enzyme Composition #1 | Standard deviation | Enzyme dose | Cellulolytic Enzyme Composition #2 | Standard deviation | |
| 10 mg enzyme per g TS | 104.9 | 0.7 | 10.27 mg enzyme per g TS | 117.0 | 2.1 | p = 0.0060* |
| 15 mg enzyme per g TS | 113.2 | 0.6 | 15.4 mg enzyme per g TS | 123.9 | 0.3 | p = 0.0002* |

TABLE 4

Mannose concentration (g/kg) after 72 hours hydrolysis.

| Enzyme dose | Cellulolytic Enzyme Composition #1 | Standard deviation | Enzyme dose | Cellulolytic Enzyme Composition #2 | Standard deviation | |
|---|---|---|---|---|---|---|
| 10 mg enzyme per g TS | 4.8 | 0.1 | 10.27 mg enzyme per g TS | 10.0 | 0.3 | p = 0.0004* |
| 15 mg enzyme per g TS | 6.1 | 0.2 | 15.4 mg enzyme per g TS | 9.6 | 0.4 | p = 0.0024* |

Cellulolytic Enzyme Composition #2 produced significantly higher glucose and mannose concentrations compared to Cellulolytic Enzyme Composition #1.

Example 4: Hydrolysis of Softwood

Wood chips from Norway spruce (*Picea abies*) were pretreated in a two stage process and then hydrolyzed as described in Example 1.

Cellulolytic Enzyme Composition #1 and Cellulolytic Enzyme Composition #2 were used in the hydrolysis experiments. The enzyme compositions were dosed at 10 or 10.27 mg enzyme per g TS, respectively. All experiments were tested in triplicate. Samples were taken after 72 hours of hydrolysis. The samples were deactivated at 100° C. for 10 minutes and subsequently diluted 20-fold (weight/weight) in water. The diluted samples were centrifuged and the supernatants were further volume/volume diluted 20-fold and 2-fold for analysis of glucose and mannose, respectively. The samples were analyzed for glucose and mannose with a DIONEX® BIOLC® System according to the following protocol. Samples (10 µl) were loaded onto a DIONEX BIOLC® System equipped with a DIONEX® CARBOPAC™ PA1 analytical column (4×250 mm) combined with a CARBOPAC™ PA1 guard column (4×50 mm). The monosaccharides were separated isocratically with 2 mM potassium hydroxide at a flow rate of 1 ml per minute and detected by a pulsed electrochemical detector in the pulsed amperiometric detection mode. Mixtures of arabinose, galactose, glucose, xylose and mannose (concentration range of each component: 0.0050-0.075 g per liter) were used as standards. DIONEX chromatogram processing was performed using Chromeleon software. DIONEX data processing was performed using Microsoft Excel. Measured sugar concentrations were adjusted for the appropriate dilution factor.

Table 5 shows the glucose concentration (g glucose/kg hydrolysis slurry) with Cellulolytic Enzyme Compositions #1 and #2.

Table 6 shows the mannose concentration (g mannose/kg hydrolysis slurry) with Cellulolytic Enzyme Compositions #1 and #2.

TABLE 5

Glucose concentration (g/kg) after 72 hours hydrolysis.

| Enzyme dose | Cellulolytic Enzyme Composition #1 | Standard deviation | Enzyme dose | Cellulolytic Enzyme Composition #2 | Standard deviation | |
|---|---|---|---|---|---|---|
| 10 mg enzyme per g TS | 12.5 | 1.4 | 10.27 mg enzyme per g TS | 19.0 | 0.3 | p = 0.0103* |

TABLE 6

Mannose concentration (g/kg) after 72 hours hydrolysis.

| Enzyme dose | Cellulolytic Enzyme Composition #1 | Standard deviation | Enzyme dose | Cellulolytic Enzyme Composition #2 | Standard deviation | |
|---|---|---|---|---|---|---|
| 10 mg enzyme per g TS | 0.6 | 0.0 | 10.27 mg enzyme per g TS | 2.1 | 0.0 | p = 0.0002* |

Cellulolytic Enzyme Composition #2 produced significantly higher glucose and mannose concentrations compared to Cellulolytic Enzyme Composition #1.

Example 5: Hydrolysis of Softwood

Wood chips from Norway spruce (*Picea abies*) were pretreated in a two stage process as described in Example 1. The material was mechanically refined in a PFI mill according to the standard TAPPI method T248 to a severity of 20000 revolutions. For the hydrolysis experiments described here, the refined solid material was mixed with the liquid fraction from the first step of pretreatment.

Hydrolysis was performed on a 20 g scale under the following conditions: 5% total solids (TS), 50 mM citrate buffer, pH 5, 50° C. for 72 hours at 20 rpm in a FINEPCR Combi-D24 hybridization incubator.

Cellulolytic Enzyme Composition #1 and Cellulolytic Enzyme Composition #2 were used in the hydrolysis experiments. The enzyme compositions were dosed at 5, 10 and 20 or 5.13, 10.27 and 20.53 mg enzyme per g TS, respectively. All experiments were tested in triplicate. Samples were taken after 72 hours of hydrolysis. The samples were deactivated at 100° C. for 10 minutes and subsequently diluted 20-fold (weight/weight) in water. The diluted samples were centrifuged and the supernatants were further volume/volume diluted 20-fold and 2-fold for analysis of glucose and mannose, respectively. The samples were analyzed for glucose, xylose and mannose with a DIONEX® BIOLC® System according to the following protocol. Samples (10 µl) were loaded onto a DIONEX BIOLC® System equipped with a DIONEX® CARBOPAC™ PA1 analytical column (4×250 mm) combined with a CARBOPAC™ PA1 guard column (4×50 mm). The monosaccharides were separated isocratically with 2 mM potassium hydroxide at a flow rate of 1 ml per minute and detected by a pulsed electrochemical detector in the pulsed amperiometric detection mode. Mixtures of arabinose, galactose, glucose, xylose and mannose (concentration range of each component: 0.0050-0.075 g per liter) were used as standards. DIONEX chromatogram processing was performed using Chromeleon software. DIONEX data processing was performed using Microsoft Excel. Measured sugar concentrations were adjusted for the appropriate dilution factor.

Table 7 shows the glucose concentration (g glucose/kg hydrolysis slurry) for the three different enzyme doses with Cellulolytic Enzyme Compositions #1 and #2.

Table 8 shows the mannose concentration (g mannose/kg hydrolysis slurry) for the three different enzyme doses with Cellulolytic Enzyme Compositions #1 and #2.

TABLE 7

Glucose concentration (g/kg) after 72 hours hydrolysis.

| Enzyme dose | Cellulolytic Enzyme Composition #1 | Standard deviation | Enzyme dose | Cellulolytic Enzyme Composition #2 | Standard deviation | |
|---|---|---|---|---|---|---|
| 5 mg enzyme per g TS | 7.2 | 0.1 | 5.13 mg enzyme per g TS | 9.3 | 0.2 | p = 0.0005* |
| 10 mg enzyme per g TS | 10.2 | 0.7 | 10.27 mg enzyme per g TS | 14.4 | 0.6 | p = 0.0016* |
| 20 mg enzyme per g TS | 13.5 | 0.1 | 20.53 mg enzyme per g TS | 17.4 | 0.1 | p = 0.0001* |

TABLE 8

Mannose concentration (g/kg) after 72 hours hydrolysis.

| Enzyme dose | Cellulolytic Enzyme Composition #1 | Standard deviation | Enzyme dose | Cellulolytic Enzyme Composition #2 | Standard deviation | |
|---|---|---|---|---|---|---|
| 5 mg enzyme per g TS | 1.5 | 0.1 | 5.13 mg enzyme per g TS | 7.0 | 0.1 | p = 0.0001* |
| 10 mg enzyme per g TS | 2.3 | 0.0 | 10.27 mg enzyme per g TS | 8.5 | 0.2 | p = 0.0002* |
| 20 mg enzyme per g TS | 4.1 | 0.1 | 20.53 mg enzyme per g TS | 8.7 | 0.2 | p = 0.0001* |

Cellulolytic Enzyme Composition #2 gave significantly higher glucose and mannose concentrations compared to Cellulolytic Enzyme Composition #1.

Example 6: Hydrolysis of Softwood

Softwood chips were pretreated in accordance with the BALI™ concept owned by Borregaard (US 2011/0250638).

Hydrolysis was performed on a 20 g scale under the following conditions: 10% total solids (TS), 50 mM citrate buffer, pH 5, 50° C. for 72 hours at 20 rpm in a FINEPCR Combi-D24 hybridization incubator.

Cellulolytic Enzyme Composition #1, Cellulolytic Enzyme Composition #3 and Cellulolytic Enzyme Composition #4 were used in the hydrolysis. The enzyme compositions were dosed at 6, 6.24 and 6 mg enzyme per g TS, respectively. All conditions were tested in triplicates. Samples were taken after 72 hours of hydrolysis. The samples were deactivated at 100° C. for 10 min and subsequently diluted 10×(weight/weight) in 0.005 M $H_2SO_4$. The diluted samples were centrifuged and HPLC samples were taken from the supernatant. The samples were analyzed for glucose on HPLC using a 300×7.8 mm AMINEX® HPX-87H column. Elution was isocratic using 0.005 M $H_2SO_4$ at column temperature of 65° C. The flow rate was 0.6 mL/min. Quantification was done by integration of signals derived from components, using a Waters 2414 Refractive index detector (50° C. in flow cell). HPLC chromatogram processing was performed using Waters Empower software. HPLC data processing was performed using Microsoft Excel. Measured sugar concentrations were adjusted for the appropriate dilution factor.

Table 9 shows the glucose concentration (g glucose/kg hydrolysis slurry) obtained with Cellulolytic Enzyme Compositions #1 and #3.

TABLE 9

Glucose concentration (g/kg) after 72 hours hydrolysis

| Mannanase | Cellulolytic Enzyme Composition #1 | Standard deviation | Cellulolytic Enzyme Composition #3 and #4 | Standard deviation | |
|---|---|---|---|---|---|
| None | 51.7 | 0.5 | | | |
| Trichoderma reesei (#4) | | | 62.1 | 0.5 | p = 0.0001* |
| Aspergillus niger (#3) | | | 57.2 | 0.5 | p = 0.0002* |

Both Cellulolytic Enzyme Composition #3 and #4 produced an increased glucose concentration compared to Cellulolytic Enzyme Composition #1.

Example 7: Mannanases

Softwood chips were pretreated in accordance with the BALI™ concept described by Borregaard in US 2011/0250638. This concept comprises a sulfite cook of the softwood chips.

Hydrolysis was performed on a 20 g scale under the following conditions: 10% total solids (TS), 50 mM citrate buffer, 0.25% (w/w) of TS PEG6000, pH 5, 50° C. for 72 hours at 20 rpm in a FINEPCR Combi-D24 hybridization incubator.

The total enzyme dose was divided between 3 components, in the percentages shown below:

| Condition | Enzyme dose (mg) | Cellulase composition #1 | Beta-mannosidase (BM) | Endo-mannanase (EM) |
|---|---|---|---|---|
| 1 | 6 | 100% | — | — |
| 2 | 6.12 | 93.1% | 2.45% (A. niger SEQ ID NO: 12) | 4.4% (A. niger SEQ ID NO: 26) |
| 3 | 6 | 95% | 2.5% (A. niger SEQ ID NO: 12) | 2.5% (T. reesei SEQ ID NO: 27) |
| 4 | 6 | 95% | 2.5% (A. niger SEQ ID NO: 12) | 2.5% (T. leycettanus SEQ ID NO: 34) |

All experiments were performed in triplicate. Samples were taken after 72 hours of hydrolysis. The samples were deactivated at 100° C. for 10 minutes and subsequently diluted 5 times (weight/weight) in 0.005 M $H_2SO_4$. The diluted samples were centrifuged and HPLC samples were taken from the supernatant. The samples were analyzed for glucose by HPLC using a 300×7.8 mm AMINEX® HPX-87H column. Elution was isocratic using 0.005 M $H_2SO_4$ at a column temperature of 65° C. The flow rate was 0.6 mL/minute. Quantification was performed by integration of the glucose signal, using a Waters 2414 Refractive index detector (50° C. in flow cell). HPLC chromatogram processing was performed using Waters Empower software. HPLC data processing was performed using Microsoft Excel. Measured glucose concentrations were adjusted for appropriate dilution.

Table 10 shows the glucose concentration (g glucose/kg hydrolysis slurry) for the 4 different conditions.

TABLE 10

Glucose concentration (g/kg) after 72 hours hydrolysis

| Condition | Glucose concentration (g/kg) | Standard deviation | Comparison with condition 2 |
|---|---|---|---|
| 1 (Comp.#1) | 51.7 | 0.5 | p = 0.0002* |
| 2 (A. niger EM) | 57.2 | 0.5 | — |
| 3 (T. reesei EM) | 62.1 | 0.5 | p = 0.0003* |
| 4 (T. leycettanus EM) | 64.1 | 0.2 | p < 0.0001* |

T. leycettanus and T. reesei endo-mannanases gives significantly higher glucose concentrations compared to A. niger endo-mannanase.

Example 8: Mannanases on PKC—Thermo Stability and Conversion Efficiency

Hydrolysis of Palm Kernel Cake (PKC) was performed on a 20 g scale under the following conditions: 25% total solids (TS), 50 mM citrate buffer, 0.2% (w/w) Proxel, pH 5, 55-60-65° C. for 72 hours at 20 rpm in a FINEPCR Combi-D24 hybridization incubator.

The total enzyme dose was 0.5 mg enzyme per g TS. The total enzyme dose was divided between 3 components, in the percentages shown below:

| Condition | Temp ° C. | Cellulase composition #1 | Beta-mannosidase (BM) | Endo-mannanase (EM) |
|---|---|---|---|---|
| 1 | 55 | 12% Cellulase | 36% (*A. niger* SEQ ID NO: 12) | 52% (*A. niger* SEQ ID NO: 26) |
| 2 | 55 | 10% Cellulase | 45% (*A. niger* SEQ ID NO: 12) | 45% (*T. leycettanus* SEQ ID NO: 34) |
| 3 | 60 | 12% Cellulase | 36% (*A. niger* SEQ ID NO: 12) | 52% (*A. niger* SEQ ID NO: 26) |
| 4 | 60 | 10% Cellulase | 45% (*A. niger* SEQ ID NO: 12) | 45% (*T. leycettanus* SEQ ID NO: 34) |
| 5 | 65 | 12% Cellulase | 36% (*A. niger* SEQ ID NO: 12) | 52% (*A. niger* SEQ ID NO: 26) |
| 6 | 65 | 10% Cellulase | 45% (*A. niger* SEQ ID NO: 12) | 45% (*T. leycettanus* SEQ ID NO: 34) |

Prior to the trials in this example, optimal ratios between the cellulase, beta-mannosidase, *A. niger/T. leycettanus* endo-mannanase were determined.

All experiments were performed in duplicates. Samples were taken after 72 hours of hydrolysis. The samples were diluted 10 times (weight/weight) in 0.005 M $H_2SO_4$. The diluted samples were centrifuged and HPLC samples were taken from the supernatant. The samples were analyzed for glucose and mannose by HPLC using a 300×7.8 mm AMINEX® HPX-87H column. Elution was isocratic using 0.005 M $H_2SO_4$ at a column temperature of 65° C. The flow rate was 0.6 mL/minute. Quantification was performed by integration of the glucose signal, using a Waters 2414 Refractive index detector (50° C. in flow cell). HPLC chromatogram processing was performed using Waters Empower software. HPLC data processing was performed using Microsoft Excel. Measured glucose and mannose concentrations were adjusted for appropriate dilution.

Table 11 shows the glucose, mannose and average C6 sugar conversion of theoretical possible in PKC (Conversion %) for the 6 different conditions.

TABLE 11

Theoretical Conversion % (average) after 72 hours hydrolysis.

| Condition | Temp ° C. | Conversion % AVG | | | Standard deviation | | |
|---|---|---|---|---|---|---|---|
| | | Glucose | Mannose | C6 | Glucose | Mannose | C6 |
| 1 | 55° C. | 52.8% | 70.4% | 67.8% | 0.55% | 0.19% | 0.25% |
| 2 | 55° C. | 59.2% | 79.8% | 76.8% | 0.19% | 0.74% | 0.66% |
| 3 | 60° C. | 55.6% | 76.2% | 73.2% | 2.13% | 0.46% | 0.71% |
| 4 | 60° C. | 65.2% | 88.4% | 85.0% | 1.05% | 0.58% | 0.34% |
| 5 | 65° C. | 27.7% | 80.3% | 72.6% | 2.00% | 0.46% | 0.68% |
| 6 | 65° C. | 32.3% | 84.8% | 77.1% | 4.04% | 4.02% | 4.02% |

*T. leycettanus* endo-mannanase gives significantly higher average glucose, mannose and total C6 sugar conversion compared to *A. niger* endo-mannanase. Furthermore, *T. leycettanus* endo-mannanase shows significantly higher thermo stability compared to *A. niger* endo-mannanase.

Example 9: Mannanases on PKC—Enzyme Dosage Efficiency

Hydrolysis of Palm Kernel Cake (PKC) was performed on a 20 g scale under the following conditions: 25% total solids (TS), 50 mM citrate buffer, 0.2% (w/w) Proxel, pH 5, 60° C. for 72 hours at 20 rpm in a FINEPCR Combi-D24 hybridization incubator.

The total enzyme dose was 0.3-0.4-0.5 mg enzyme per g TS. The total enzyme dose was divided between 3 components, in the percentages shown below:

| Condition | Enzyme dosage | Cellulase composition #1 | Beta-mannosidase (BM) | Endo-mannanase (EM) |
|---|---|---|---|---|
| 1 | 0.3 | 12% | 36% (*A. niger* SEQ ID NO: 12) | 52% (*A niger* SEQ ID NO: 26) |
| 2 | 0.3 | 10% | 45% (*A. niger* SEQ ID NO: 12) | 45% (*T. leycettanus* SEQ ID NO: 34) |
| 3 | 0.4 | 12% | 36% (*A. niger* SEQ ID NO: 12) | 52% (*A niger* SEQ ID NO: 26) |
| 4 | 0.4 | 10% | 45% (*A. niger* SEQ ID NO: 12) | 45% (*T. leycettanus* SEQ ID NO: 34) |
| 5 | 0.5 | 12% | 36% (*A. niger* SEQ ID NO: 12) | 52% (*A niger* SEQ ID NO: 26) |
| 6 | 0.5 | 10% | 45% (*A. niger* SEQ ID NO: 12) | 45% (*T. leycettanus* SEQ ID NO: 34) |

Prior to the trials in this example, optimal ratios between the cellulase, beta-mannosidase, *A. niger/T. leycettanus* endo-mannanase were determined.

All experiments were performed in duplicates. Samples were taken after 72 hours of hydrolysis. The samples were diluted 10 times (weight/weight) in 0.005 M $H_2SO_4$. The diluted samples were centrifuged and HPLC samples were taken from the supernatant. The samples were analyzed for glucose and mannose by HPLC using a 300×7.8 mm AMINEX® HPX-87H column. Elution was isocratic using 0.005 M $H_2SO_4$ at a column temperature of 65° C. The flow rate was 0.6 mL/minute. Quantification was performed by integration of the glucose signal, using a Waters 2414 Refractive index detector (50° C. in flow cell). HPLC chromatogram processing was performed using Waters Empower software. HPLC data processing was performed using Microsoft Excel. Measured glucose and mannose concentrations were adjusted for appropriate dilution.

Table 12 shows the glucose, mannose and average C6 sugar conversion of theoretical possible in PKC (Conversion %) for the 6 different conditions.

TABLE 12

Theoretical Conversion % (average) after 72 hours hydrolysis.

| Condition | Enzyme dosage | Conversion % AVG | | | Standard deviation | | |
|---|---|---|---|---|---|---|---|
| | | Glucose | Mannose | C6 | Glucose | Mannose | C6 |
| 1 | 0.3 | 43.2% | 68.4% | 64.7% | 0.22% | 0.11% | 0.06% |
| 2 | 0.3 | 49.1% | 79.4% | 75.0% | 0.99% | 0.74% | 0.78% |
| 3 | 0.4 | 50.6% | 73.1% | 69.8% | 0.89% | 1.00% | 0.99% |
| 4 | 0.4 | 57.4% | 84.0% | 80.1% | 0.50% | 0.19% | 0.23% |
| 5 | 0.5 | 55.6% | 76.2% | 73.2% | 2.13% | 0.46% | 0.71% |
| 6 | 0.5 | 65.2% | 88.4% | 85.0% | 1.05% | 0.58% | 0.34% |

*T. leycettanus* endo-mannanase gives almost same performance at 0.3 mg enzyme per g TS as *A. niger* endo-mannanase does at 0.5 mg enzyme per g TS. This shows that *T. leycettanus* endo-mannanase is significantly more efficient than *A. niger* endo-mannanase at lower dosage.

Example 10: Mannanases

Softwood chips were pretreated in accordance with the BALI™ concept described by Borregaard in US 2011/0250638 A1. This concept comprises a sulfite cook of the softwood chips.

Hydrolysis was performed on a 20 g scale under the following conditions: 10% total solids (TS), 50 mM citrate buffer, 0.25% (w/w) of TS PEG6000, pH 5, 50° C. for 72 hours at 20 rpm in a FINEPCR Combi-D24 hybridization incubator.

The total enzyme dose was divided between 3 components, in the percentages shown below:

| Condition | Enzyme dose (mg) | Cellulase composition #1 | Beta-mannosidase (BM) | Endo-mannanase (EM) |
|---|---|---|---|---|
| 1 | 6.12 | 93.14% | 2.5% (*A. niger* SEQ ID NO: 12) | 4.4% (*A. niger* SEQ ID NO: 26) |
| 2 | 6 | 95% | 2.5% (*A. niger* SEQ ID NO: 12) | 2.5% (*C. maritima* SEQ ID NO: 35) |

All experiments were performed in triplicate. Samples were taken after 72 hours of hydrolysis. The samples were deactivated at 100° C. for 10 minutes and subsequently diluted 5 times (weight/weight) in 0.005 M $H_2SO_4$. The diluted samples were centrifuged and HPLC samples were taken from the supernatant. The samples were analyzed for glucose by HPLC using a 300×7.8 mm AMINEX® HPX-87H column. Elution was isocratic using 0.005 M $H_2SO_4$ at a column temperature of 65° C. The flow rate was 0.6 mL/minute. Quantification was performed by integration of the glucose signal, using a Waters 2414 Refractive index detector (50° C. in flow cell). HPLC chromatogram processing was performed using Waters Empower software. HPLC data processing was performed using Microsoft Excel. Measured glucose concentrations were adjusted for appropriate dilution.

Table 13 shows the glucose concentration (g glucose/kg hydrolysis slurry) for the 4 different conditions.

TABLE 13

Glucose concentration (g/kg) after 72 hours hydrolysis

| Condition | Glucose concentration (g/kg) | Standard deviation | Comparison with condition 1 |
|---|---|---|---|
| 1 (*A. niger* EM) | 52.9 | 1.1 | — |
| 2 (*C. maritima* EM) | 55.7 | 0.6 | p = 0.0176* |

*C. maritima* endo-mannanase give significantly higher glucose concentration compared to *A. niger* endo-mannanase.

Example 11: Addition of *T. leycettanus* Endo-Mannanase to Commercial Cellulase Blend, Celluclast™, Boost Glucose and Hemicellulose Yields Softwood chips were pretreated in accordance with the BALI™ concept described by Borregaard in US 2011/0250638. This concept comprises a sulfite cook of the softwood chips. The cellulase composition used is a commercial whole cellulase blend, Celluclast™ (available from Novozymes A/S). Celluclast is a liquid cellulase preparation made by submerged fermentation of a selected strain of the fungus *Trichoderma reesei*.

Hydrolysis was performed on a 20 g scale under the following conditions: 15% total solids (TS), 100 mM citrate buffer, 50° C., pH 5, at 20 rpm in a FINEPCR Combi-D24 hybridization incubator.

The total enzyme dose was 8.0 mg enzyme per g TS. The total enzyme dose was divided between 3 components, in the percentages shown below:

| Condition | Cellulase blend (Celluclast ™) | *T. leycettanus* endo-mannanase (EM) | *A. niger* beta-mannosidase (BM) |
|---|---|---|---|
| 1 | 100% | | |
| 2 | 95% | 2.5% | 2.5% |

All experiments were performed in quadruplicate. Samples were taken after 72 and 96 hours of hydrolysis. The samples were deactivated at 100° C. for 10 minutes and subsequently diluted 8 times (weight/weight) in HPLC eluent. The diluted samples were centrifuged and supernatants filtered through 0.22 μm syringe filters. The samples were analyzed for sugars by HPLC using a 300×7.8 mm AMINEX® HPX-87H column. Elution was isocratic using 0.005 M $H_2SO_4$ at a column temperature of 65° C. The flow rate was 0.6 mL/minute. Quantification was performed by integration of the sugar signals, using a Waters 2414 Refractive index detector (50° C. in flow cell). HPLC chromatogram processing was performed using Waters Empower software. HPLC data processing was performed using Microsoft Excel. Measured sugar concentrations were adjusted for appropriate dilution. Hemicellulose is a measure of both mannose and xylose, quantified using xylose standards, as these two sugars co-elute on the HPX-87H column.

Table 14 shows the glucose and hemicellulose (xylose and mannose) concentration (g sugar/kg hydrolysis slurry) followed by standard deviations in brackets for the two different conditions after different hydrolysis times. P-values are obtained by comparison of condition 1 and 2 using Student's t-test.

TABLE 14

| Condition | Glucose (g/kg), 72 h | Glucose (g/kg), 96 h | Hemicellulose (g/kg), 72 h | Hemicellulose (g/kg), 96 h |
|---|---|---|---|---|
| 1 | 36.35 (0.59) | 41.41 (0.50) | 2.36 (0.03) | 2.64 (0.03) |
| 2 | 38.67 (0.09) | 43.79 (0.38) | 4.38 (0.05) | 4.91 (0.03) |
|   | $p < 0.001$* | $p < 0.001$* | $p < 0.0001$* | $p < 0.0001$* |

Conclusion: Addition of *T. leycettanus* endo-mannanase and *A. niger* beta-mannosidase to Celluclast results in significantly higher glucose and hemicellulose yields from softwood compared to Celluclast alone.

Example 12: *A. niger* Endo-Mannanase in Combination with Cellulase Composition #5, 20 g Scale, 5% TS at 50° C.

Wood chips from Norway spruce (*Picea abies*) were pretreated with steam in a two stage process. The first stage was performed at 175° C. for 30 minutes, followed by separation of the solid and liquid fraction by pressing of the wood material. The solid fraction from the first stage was treated in the second stage at 210° C. for 5 minutes. For the hydrolysis experiments described here, only the material from the second stage was used. This material was mechanically refined in a PFI mill according to the standard TAPPI method T248 to a severity of 20K revolutions.

Hydrolysis was performed on a 20 g scale under the following conditions: 5% total solids (TS), 50 mM citrate buffer, pH 5, 50° C. for 72 hours at 20 rpm in a FINEPCR Combi-D24 hybridization incubator.

The total enzyme dose was either 10 or 20 mg Cellulase composition #5 enzyme per g TS or 10.4 and 20.8 mg Cellulase composition #5/endo-mannanase/beta-mannosidase enzyme blend per g TS. The total enzyme dose was divided between 3 components, in the percentages shown below:

| Condition | Cellulase composition #5 | Beta-mannosidase (BM) SEQ ID NO: 12 | Endo-mannanase (EM) SEQ ID NO: 26 |
|---|---|---|---|
| 1 | 100% | 0% | 0% |
| 2 | 86.54% | 4.81% *A. niger* | 8.65% *A. niger* |

All experiments were performed in triplicate. Samples were taken after 72 hours of hydrolysis. The samples were deactivated at 100° C. for 10 minutes and subsequently diluted 10 times (weight/weight) in 0.005 M $H_2SO_4$. The diluted samples were centrifuged and supernatants filtered through 0.22 μm syringe filters. The samples were analyzed for glucose by HPLC using a 300×7.8 mm AMINEX® HPX-87H column. Elution was isocratic using 0.005 M $H_2SO_4$ at a column temperature of 65° C. The flow rate was 0.6 mL/minute. Quantification was performed by integration of the glucose signal, using a Waters 2414 Refractive index detector (50° C. in flow cell). HPLC chromatogram processing was performed using Waters Empower software. HPLC data processing was performed using Microsoft Excel. Measured glucose concentrations were adjusted for appropriate dilution.

Table 15 shows the glucose concentration (g glucose/kg hydrolysis slurry) for the 4 different conditions.

TABLE 15

Glucose concentration (g/kg) after 72 hours hydrolysis. P-values are obtained by comparison of condition 1 and 2 using Student's t-test.

| Condition | Total enzyme dose (mg/g TS) | Glucose concentration (g/kg) | Standard deviation | Comparison with condition 1 |
|---|---|---|---|---|
| 1 Cellulase composition #5 | 10 | 12.17 | 0.05 | — |
| 2 Cellulase composition #5 + EM + BM | 10.4 | 13.17 | 0.09 | $p < 0.0001$* |
| 1 Cellulase composition #5 | 20 | 16.93 | 0.10 | — |
| 2 Cellulase composition #5 + EM + BM | 20.8 | 17.79 | 0.11 | $p < 0.001$* |

Addition of *A. niger* endo-mannanase and beta-mannosidase to Cellulase composition #5 results in significantly higher glucose yields compared to Cellulase composition #5 alone.

Example 13: Mannanases Boost Hydrolysis of MSW

Experiments were performed using different batches of Municipal Solid Waste (MSW). By supplementing cellulase composition #1 with either *A. niger*, *T. leycettanus* or *T. reesei* mannanase, improvements in hydrolysis were observed.

Experiment 1:

The substrate used in this experiment was MSW substrate which was cooked and then refined in a PFI mill. Solids content was 10% and hydrolysis assays were carried out in 20 g scale at 50° C. for 72 hours. Enzyme blends and their corresponding dosage are described in table 16 as well as the resulting glucan conversion:

TABLE 16

| Mg EP/g TS Cellulase comp. #1. | Mg EP/g TS *A. niger* mannanase | % glucan conversion |
|---|---|---|
| 3.6 | 0 | 75.6 |
| 3.42 | 0.32 | 80.1 |
| 3.24 | 0.65 | 80.2 |
| 2.88 | 1.30 | 80.4 |

Conclusion: Addition of *A. niger* mannanase (SEQ ID NO: 26) to Cellulase comp. #1 boost glucan conversion of MSW.

Experiment 2:

The MSW substrate used in this experiment was cooked but not refined. Solids content was 5% and hydrolysis assays were carried out in 24-wells plates at 50° C. for 72 hours. A total protein loading of 3.6 mg enzyme protein per gram total solids were used. Enzyme blends are described in table 17 below as well as the resulting glucan conversion:

TABLE 17

| Cellulase composition # 1 | T. leycettanus mannanase | T. reesei mannanase | % glucan conversion |
|---|---|---|---|
| 100% | 0% | 0% | 31.5 |
| 95% | 5% | 0% | 36.8 |
| 90% | 0% | 10% | 35.8 |

Conclusion: Supplementing Cellulase composition #1 enzyme protein with either 5% *T. leycettanus* mannanase (SEQ ID NO: 34) or 10% *T. reesei* mannanase (SEQ ID NO: 27) boost glucan conversion of MSW.

---

The invention claimed is:

1. A process for degrading a mannan-containing cellulosic material, comprising: treating the mannan-containing cellulosic material with an enzyme composition comprising one or more cellulases and at least one mannanase at a temperature in the range from 30° C. to 65° C., wherein the mannanase comprises SEQ ID NO: 34 or the mannanase comprises an amino acid sequence having at least 90% sequence identity to SEQ ID NO: 34.

2. The process of claim 1, wherein the enzyme composition further comprises one or more of an AA9 polypeptide, a beta-glucosidase, a beta-mannosidase, a beta-xylosidase, a cellobiohydrolase I, a cellobiohydrolase II, an endoglucanase, and a xylanase.

3. The process of claim 1, further comprising pretreating the mannan-containing cellulosic material prior to treatment of the mannan-containing cellulosic material.

4. The process of claim 1, wherein the mannan-containing cellulosic material is municipal solid waste.

5. The process of claim 1, further comprising recovering the degraded mannan-containing cellulosic material.

6. The process of claim 5, wherein the degraded mannan-containing cellulosic material is a sugar.

7. A process for producing a fermentation product, comprising:
(a) saccharifying a mannan-containing cellulosic material with an enzyme composition comprising one or more cellulases and at least one mannanase at a temperature in the range from 30° C. to 65° C., wherein the mannanase comprises SEQ ID NO: 34 or the mannanase comprises an amino acid sequence having at least 90% sequence identity to SEQ ID NO: 34;
(b) fermenting the saccharified mannan-containing cellulosic material with a fermenting microorganism to produce the fermentation product; and
(c) recovering the fermentation product from the fermentation.

8. The process of claim 7, wherein the enzyme composition further comprises one or more of an AA9 polypeptide, a beta-glucosidase, a beta-mannosidase, a beta-xylosidase, a cellobiohydrolase I, a cellobiohydrolase II, an endoglucanase, and a xylanase.

9. The process of claim 7, further comprising pretreating the mannan-containing cellulosic material prior to saccharification.

10. The process of claim 7, wherein the fermentation product is an alcohol, an alkane, a cycloalkane, an alkene, an amino acid, a gas, isoprene, a ketone, an organic acid, or polyketide.

11. A process for producing a fermentation product, the process comprising (a) contacting an aqueous slurry of a mannan-containing cellulosic material with an enzyme composition to produce a soluble hydrolyzate, wherein the enzyme composition comprises one or more cellulases and at least one mannanase at a temperature in the range from 30° C. to 65° C., wherein the mannanase comprises SEQ ID NO: 34 or the mannanase comprises an amino acid sequence having at least 90% sequence identity to SEQ ID NO: 34; and (b) contacting the soluble hydrolyzate with a fermenting organism to produce a fermentation product.

12. The process of claim 11, wherein the enzyme composition further comprises one or more of an AA9 polypeptide, a beta-glucosidase, a beta-mannosidase, a beta-xylosidase, a cellobiohydrolase I, a cellobiohydrolase II, an endoglucanase, and a xylanase.

* * * * *